United States Patent
Shin et al.

(10) Patent No.: US 11,393,991 B2
(45) Date of Patent: Jul. 19, 2022

(54) HETEROCYCLIC COMPOUND AND ORGANIC ELECTROLUMINESCENCE DEVICE INCLUDING THE SAME

(71) Applicants: Samsung Display Co., Ltd., Yongin-Si (KR); INDUSTRY-ACADEMIC COOPERATION FOUNDATION GYEONGSANG NATIONAL UNIVERSITY, Jinju-si (KR)

(72) Inventors: Daeyup Shin, Suwon-si (KR); Seulong Kim, Cheonan-si (KR); Taekyung Kim, Yongin-si (KR); Jungsub Lee, Hwaseong-si (KR); Soon-ki Kwon, Jinju-si (KR); Yun-hi Kim, Jinju-si (KR); Yeonhee Ha, Jinju-si (KR); Jaeyoung Hwang, Jinju-si (KR)

(73) Assignees: SAMSUNG DISPLAY CO., LTD., Yongin-si (KR); INDUSTRY-ACADEMIC COOPERATION FOUNDATION GYEONGSANG NATIONAL UNIVERSITY, Jinju-si (KR)

( * ) Notice: Subject to any disclaimer, the term of this patent is extended or adjusted under 35 U.S.C. 154(b) by 393 days.

(21) Appl. No.: 16/037,937

(22) Filed: Jul. 17, 2018

(65) Prior Publication Data
US 2019/0044076 A1 Feb. 7, 2019

(30) Foreign Application Priority Data
Aug. 1, 2017 (KR) .................. 10-2017-0097829

(51) Int. Cl.
*H01L 51/50* (2006.01)
*H01L 51/00* (2006.01)
(Continued)

(52) U.S. Cl.
CPC ........ *H01L 51/0094* (2013.01); *C07D 209/86* (2013.01); *C07D 209/88* (2013.01);
(Continued)

(58) Field of Classification Search
None
See application file for complete search history.

(56) References Cited

U.S. PATENT DOCUMENTS

| 8,367,224 B2 | 2/2013 | Katakura et al. |
| 9,166,175 B2 | 10/2015 | Xia et al. |

(Continued)

FOREIGN PATENT DOCUMENTS

| CN | 101126020 | 2/2008 |
| CN | 102775432 A | 11/2012 |

(Continued)

OTHER PUBLICATIONS

E. Varathan et al., "Quantum chemical design of carbazole- and pyridoindole-based ambipolar host materials for blue phosphorescent OLEDs", RSC Advances, Aug. 1, 2016, pp. 74769-74784, vol. 6.

(Continued)

*Primary Examiner* — Gregory D Clark
(74) *Attorney, Agent, or Firm* — Kile Park Reed & Houtteman PLLC

(57) ABSTRACT

Provided are a heterocyclic compound represented by Formula 1 below, and an organic electroluminescence device including the same in an emission layer.

(Continued)

US 11,393,991 B2
Page 2

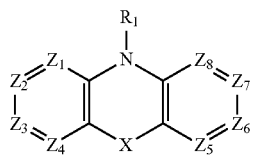

[Formula 1]

In Formula 1, X is a direct linkage or $CR_2R_3$, $Z_1$ to $Z_8$ are each independently $CR_4$ or N, at least two of $Z_1$, $Z_3$, $Z_6$ and $Z_8$ are each independently $CR_5$, and $R_5$ is represented by Formula 2 or Formula 3 below.

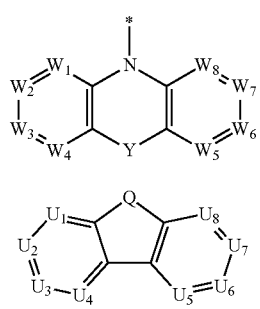

[Formula 2]

[Formula 3]

19 Claims, 3 Drawing Sheets

(51) Int. Cl.
| C07D 401/14 | (2006.01) |
| C07F 7/08 | (2006.01) |
| C07D 471/14 | (2006.01) |
| C09K 11/06 | (2006.01) |
| C07D 209/88 | (2006.01) |
| C07D 405/14 | (2006.01) |
| C07D 209/86 | (2006.01) |
| C07D 487/14 | (2006.01) |
| C07D 413/14 | (2006.01) |
| C07D 403/14 | (2006.01) |
| C07D 409/14 | (2006.01) |
| C07F 7/10 | (2006.01) |
| C07D 519/00 | (2006.01) |
| C07D 417/14 | (2006.01) |

(52) U.S. Cl.
CPC ......... *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 471/14* (2013.01); *C07D 487/14* (2013.01); *C07D 519/00* (2013.01); *C07F 7/0812* (2013.01); *C07F 7/10* (2013.01); *C09K 11/06* (2013.01); *H01L 51/0067* (2013.01); *H01L 51/0072* (2013.01); *C09K 2211/1007* (2013.01); *C09K 2211/1014* (2013.01); *C09K 2211/1018* (2013.01); *H01L 51/5016* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| 9,382,206 | B2 | 7/2016 | Kato et al. |
| 10,109,801 | B2 | 10/2018 | Lee et al. |
| 10,418,564 | B2 | 9/2019 | Parham et al. |
| 2008/0269461 | A1 | 10/2008 | Van Dijken et al. |
| 2009/0236974 | A1* | 9/2009 | Tamaru ........... H05B 33/14 313/504 |
| 2012/0181524 | A1* | 7/2012 | Kato ............... C07D 401/14 257/40 |
| 2012/0205636 | A1* | 8/2012 | Kim ................ H01L 51/0072 257/40 |
| 2012/0256169 | A1 | 10/2012 | Dyatkin et al. |
| 2016/0248023 | A1 | 8/2016 | Parham et al. |
| 2017/0033296 | A1 | 2/2017 | Parham et al. |
| 2017/0062730 | A1 | 3/2017 | Ahn et al. |
| 2017/0271597 | A1 | 9/2017 | Miyata et al. |
| 2017/0301868 | A1 | 10/2017 | Lee |
| 2017/0309829 | A1 | 10/2017 | Jung et al. |

FOREIGN PATENT DOCUMENTS

| JP | 2009-524703 | 7/2009 |
| JP | 2009-224763 | 10/2009 |
| JP | 2014-511861 | 5/2014 |
| JP | 5983648 B | 9/2016 |
| JP | 2017-519809 | 7/2017 |
| JP | 2017-520904 | 7/2017 |
| KR | 10-2011-0043342 | 4/2011 |
| KR | 10-2013-0135039 | 12/2013 |
| KR | 10-2014-0078397 | 6/2014 |
| KR | 10-2015-0061174 | 6/2015 |
| KR | 10-2015-0127548 | 11/2015 |
| KR | 10-2016-0065207 A | 6/2016 |
| KR | 10-2016-0076336 A | 6/2016 |
| KR | 10-2016-0076882 | 7/2016 |
| KR | 2016-080420 * | 7/2016 | ............ H01L 51/50 |
| KR | 10-2016-0119240 | 10/2016 |
| KR | 10-2017-0001398 A | 1/2017 |
| KR | 10-2017-0021300 A | 2/2017 |
| WO | 2012/029253 | 3/2012 |
| WO | 2015154843 A1 | 10/2015 |
| WO | 2015170882 A1 | 11/2015 |
| WO | 2016056757 A2 | 4/2016 |
| WO | 2016/105161 | 6/2016 |
| WO | WO 2016/089165 A2 * | 6/2016 | ............ H01L 51/50 |
| WO | 2017/115608 | 7/2017 |

OTHER PUBLICATIONS

Rajendra Kumar Konidena et al., "Star-Shaped Asymmetrically Substituted Blue Emitting Carbazoles: Synthesis, Photophyscial, Electrochemical and Theoretical Investigations", ChemistrySelect, 2017, pp. 7514-7524, vol. 2.

Wen-Liang Gong et al., "Carbazole oligomers revisited: new additions at the carbazole 1- and 8-positions", RSC Advances, Sep. 17, 2012, pp. 10821-10828, vol. 2.

\* cited by examiner

HETEROCYCLIC COMPOUND AND ORGANIC ELECTROLUMINESCENCE DEVICE INCLUDING THE SAME

CROSS-REFERENCE TO RELATED APPLICATIONS

This application claims priority under 35 U.S.C. § 119 of Korean Patent Application No. 10-2017-0097829 filed on Aug. 1, 2017, the entire content of which is hereby incorporated by reference.

BACKGROUND

The present disclosure herein relates to a heterocyclic compound and an organic electroluminescence device including the same.

The development of an organic electroluminescence display as an image display is being actively conducted. The organic electroluminescence display is different from a liquid crystal display and is a self-luminescent display accomplishing displays via recombination of holes and electrons injected from a first electrode and a second electrode in an emission layer and via light emission from a luminescent material including an organic compound in the emission layer.

As an organic electroluminescence device, an organic device including, for example, a first electrode, a hole transport layer disposed on the first electrode, an emission layer disposed on the hole transport layer, an electron transport layer disposed on the emission layer, and a second electrode disposed on the electron transport layer is well known. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light using light generated by the transition of the excitons to a ground state. In addition, an embodiment of the configuration of the organic electroluminescence device is not limited thereto, but various modifications may be possible.

SUMMARY

The present disclosure provides a heterocyclic compound and an organic electroluminescence device including the same.

An embodiment of the present disclosure provides a heterocyclic compound represented by the following Formula 1:

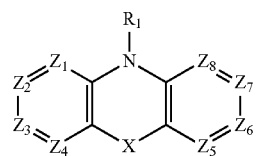

[Formula 1]

In Formula 1, X is a direct linkage, or $CR_2R_3$, $Z_1$ to $Z_8$ are each independently $CR_4$ or N, $R_1$ to $R_4$ are each independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring, at least two of $Z_1$, $Z_3$, $Z_6$ and $Z_8$ are each independently $CR_5$, and $R_5$ is represented by the following Formula 2 or Formula 3:

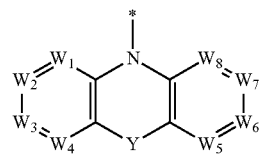

[Formula 2]

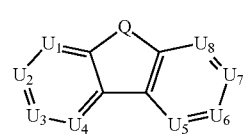

[Formula 3]

In Formula 2, Y is a direct linkage, $CR_6R_7$, $SiR_8R_9$, $NR_{10}$, O, S or $SO_2$, each of $W_1$ to $W_8$ is independently $CR_{11}$ or N, and each of $R_6$ to $R_{11}$ is independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring.

In Formula 3, Q is $NR_{12}$, O, or S, each of $U_1$ to $U_8$ is independently $CR_{13}$ or N, one of $U_1$ to $U_8$ is a connecting part, and each of $R_{12}$ and $R_{13}$ is independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring.

In an embodiment, each of $Z_1$ and $Z_3$ may independently be represented by $CR_5$.

In an embodiment, each of $Z_1$ and $Z_3$ may independently be represented by $CR_5$, and each of $Z_6$ and $Z_8$ is independently $CR_4$ wherein $R_4$ is a hydrogen atom, or represented by $CR_5$ or one of the following structures:

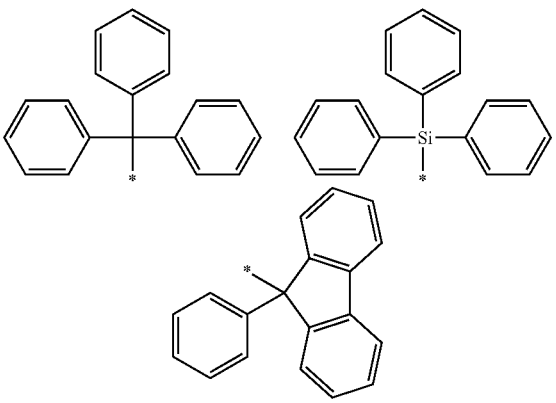

In an embodiment, R₁ may be a substituted or unsubstituted phenyl group, a substituted or unsubstituted pyridine group, or a substituted or unsubstituted carbazole group.

In an embodiment, R₁ may be represented by one of the following structures:

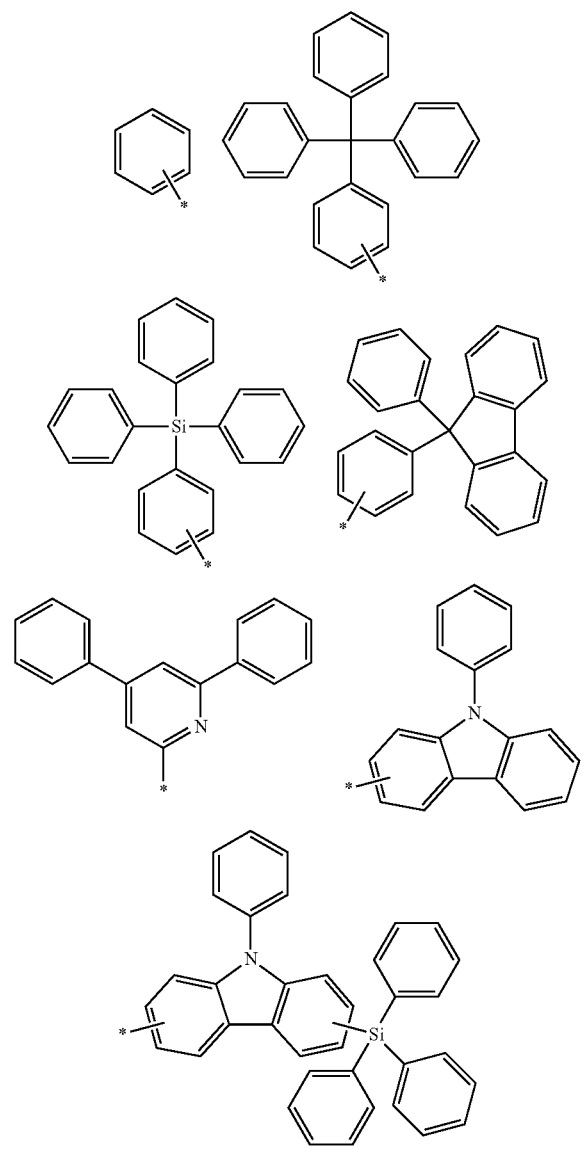

In an embodiment, either $Z_1$ and $Z_8$, or $Z_3$ and $Z_6$, may be $CR_5$, where $R_5$ may be represented by Formula 3, and if $Z_1$ and $Z_8$ are $CR_5$, at least one of $Z_3$ and $Z_6$ may be N, and if $Z_3$ and $Z_6$ are $CR_5$, at least one of $Z_1$ and $Z_8$ may be N. In this case, in Formula 3, Q may be O, and at least one of $U_2$ and $U_7$ may be N.

In Formula 2, Y may be a direct linkage, and all $W_1$ to $W_8$ may be $CR_{11}$ or at least one of $W_1$, $W_3$, $W_6$ or $W_8$ may be N.

In Formula 2, Y may be a direct linkage, and either $W_1$ and $W_3$, or $W_6$ and $W_8$, may be N.

In an embodiment, Formula 1 may be represented by the following Formula 5:

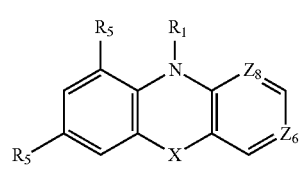

[Formula 5]

In Formula 5, each $R_5$ is independently represented by Formula 2 or Formula 3, $R_1$ is a substituted or unsubstituted phenyl group, a substituted or unsubstituted pyridine group, or a substituted or unsubstituted carbazole group, and X, $Z_6$ and $Z_8$ are the same as described above.

In an embodiment, X may be a direct linkage, and a torsional angle of a single bond connecting Formula 1 with Formula 2 or Formula 3 may be about 50 degrees or more.

In an embodiment, X may be $CR_2R_3$, and a torsional angle of a single bond connecting Formula 1 with Formula 2 or Formula 3 may be about 70 degrees or more.

In an embodiment of the present disclosure, an organic electroluminescence device includes a first electrode, a hole transport region provided on the first electrode, an emission layer provided on the hole transport region, an electron transport region provided on the emission layer, and a second electrode provided on the electron transport region, wherein the emission layer includes the heterocyclic compound according to an embodiment of the present disclosure.

In an embodiment, the emission layer may include a host and a dopant, and the host may include the heterocyclic compound according to an embodiment of the present disclosure.

In an embodiment, the host may be a phosphorescence host or a thermally activated delayed fluorescence host.

In an embodiment of the present disclosure, there is provided a heterocyclic compound represented by the following Formula A:

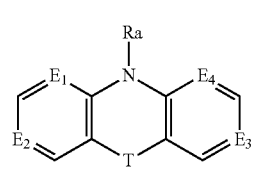

[Formula A]

In Formula A, Ra is a substituted or unsubstituted phenyl group, or a substituted or unsubstituted heterocyclic group including at least one N as a heteroatom, T is a direct linkage or CRbRc, each of $E_1$ to $E_4$ is independently CRd or N, each of Rb to Rd is independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring, "m" is an integer of 0 to 5, if "m" is 2 or more, a plurality of Ra are the same or different, and at least two of $E_1$ to $E_4$ are each independently CRe, where Re is a substituted or unsubstituted heterocyclic ring group having at least three rings.

In an embodiment, $E_1$ and $E_2$ may be CRe.

BRIEF DESCRIPTION OF THE FIGURES

The accompanying drawings are included to provide a further understanding of the present disclosure, and are incorporated in and constitute a part of this specification. The drawings illustrate exemplary embodiments of the present disclosure and, together with the description, serve to explain principles of the present disclosure. In the drawings.

DETAILED DESCRIPTION

Figure 1:
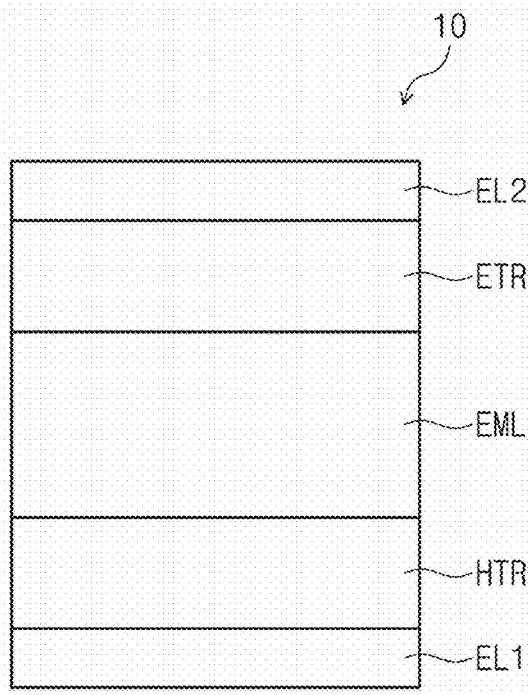
FIG. 1 is a cross-sectional view schematically illustrating an organic electroluminescence device according to an embodiment of the present disclosure.

The above objects, other objects, features and advantages of the present disclosure will be easily understood from preferred exemplary embodiments with reference to the accompanying drawings. The present disclosure may, however, be embodied in different forms and should not be construed as limited to the embodiments set forth herein.

Like reference numerals refer to like elements for explaining each drawing. In the drawings, the sizes of elements may be enlarged for clarity of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening layers may also be present. On the contrary, when a layer, a film, a region, a plate, etc. is referred to as being "under" another part, it can be "directly under" the other part, or intervening layers may also be present.

In the present disclosure, ----* means a connecting part.

In the present disclosure, "substituted or unsubstituted" may mean unsubstituted or substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heteroaryl group. In addition, each of the substituent illustrated above may be substituted or unsubstituted. For example, biphenyl may be interpreted as aryl, or phenyl substituted with phenyl.

In the present disclosure, the term "forming a ring via combination from each other" may mean forming a substituted or unsubstituted cyclic hydrocarbon ring, or a substituted or unsubstituted heterocycle via combination from each other. In addition, a ring formed via combination of adjacent groups may be connected with another ring to form a spiro structure.

In the present disclosure, a hydrocarbon ring includes an aliphatic hydrocarbon ring and an aromatic hydrocarbon ring (aryl group). The heterocycle includes an aliphatic heterocycle and an aromatic heterocycle (heteroaryl group). The hydrocarbon ring and the heterocycle may be a monocycle or polycycle.

In the present disclosure, examples of a halogen atom include a fluorine atom, a chlorine atom, a bromine atom, or an iodine atom.

In the present disclosure, the alkyl group may have a linear or branched chain or a cycle shape. The carbon number of the alkyl group may be 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the alkenyl group may be linear or branched. The carbon number of the alkenyl group is not specifically limited, but may be 2 to 30, 2 to 20, or 2 to 10. Examples of the alkenyl group may include vinyl, 1-butenyl, 1-pentenyl, 1,3-butadienyl aryl, styrenyl, styrylvinyl, etc., without limitation.

In the present disclosure, the aryl group means an optional functional group or a substituent derived from aromatic cyclic hydrocarbon ring. The aryl group may be monocyclic aryl group or polycyclic aryl group. The carbon number of the aryl group for forming a ring may be 6 to 60, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without limitation.

In the present disclosure, fluorenyl may be substituted, or two substituents may be combined with each other to form a spiro structure. Examples of the substituted fluorenyl are as follows. However, an embodiment of the present disclosure is not limited thereto.

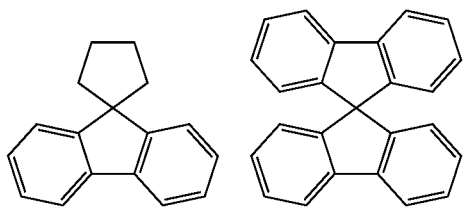

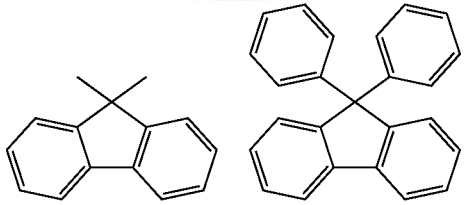

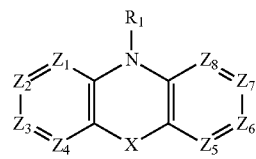

In the present disclosure, the heteroaryl group may be heteroaryl including at least one of O, N, P Si, or S as a heteroatom. If the heteroaryl includes two heteroatoms, two heteroatoms may be the same or different. The carbon number of the heteroaryl group for forming a ring may be 2 to 60, 2 to 30, or 2 to 20. The heteroaryl group may be monocyclic heteroaryl or polycyclic heteroaryl. The polycyclic heteroaryl may have a two-ring structure or a three-ring structure. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, dihydrophenazinyl, phenoxazyl, phenothiazinyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophenyl, thienothiophene, benzofuranyl, phenanthroline, thiazolyl, isooxazolyl, oxadiazolyl, thiadiazolyl, benzothiazolyl, phenothiazinyl, dibenzosilole, dibenzofuranyl, etc., without limitation.

In the present disclosure, the aliphatic heterocyclic group may include at least one of O, N, P, Si and S as a heteroatom. The carbon number for forming a ring of the aliphatic heterocyclic group may be 2 to 30, or 2 to 20. The aliphatic heterocyclic group may have a monocyclic structure or a polycyclic structure. For example, the aliphatic heterocyclic group may include phenothiazine 5,5-dioxide, etc., without limitation.

In the present disclosure, the silyl group may include alkylsilyl group and arylsilyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc., without limitation.

In the present disclosure, the boron group may include alkyl boron group and aryl boron group. Examples of the boron group may include trimethylboron, triethylboron, t-butyldimethylboron, triphenylboron, diphenylboron, phenylboron, etc., without limitation.

In the present disclosure, the carbon number of the amino group is not specifically limited, but may be 1 to 30. The amino group may include an alkyl amino group and aryl amino group. Examples of the amino group may include methylamino, dimethylamino, phenylamino, diphenylamino, naphthylamino, 9-methyl-anthracenylamino, triphenylamino, etc., without limitation.

In the present disclosure, a phosphine oxide group may be substituted with at least one of an alkyl group or an aryl group. Examples of the phosphine oxide group may include a phenyl phosphine oxide group and a diphenyl phosphine oxide group, without limitation.

First, the heterocyclic compound according to an embodiment of the present disclosure will be explained.

The heterocyclic compound according to an embodiment of the present disclosure is represented by Formula 1 below.

[Formula 1]

In Formula 1, X is a direct linkage, or $CR_2R_3$, $Z_1$ to $Z_8$ are each independently $CR_4$ or N, $R_1$ to $R_4$ are each independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring.

In Formula 1, at least two of $Z_1$, $Z_3$, $Z_6$ and $Z_8$ are each independently $CR_5$, and $R_5$ is represented by Formula 2 or Formula 3 below.

[Formula 2]

[Formula 3]

In Formula 2, Y is a direct linkage, $CR_6R_7$, $SiR_8R_9$, $NR_{10}$, O, S or $SO_2$, $W_1$ to $W_8$ are each independently $CR_{11}$ or N, and $R_6$ to $R_{11}$ are each independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring.

In Formula 3, Q is $NR_{12}$, O, or S, $U_1$ to $U_8$ are each independently $CR_{13}$ or N, one of $U_1$ to $U_8$ is a connecting part, and $R_{12}$ and $R_{13}$ are each independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring.

The heterocyclic compound according to an embodiment of the present disclosure is a compound forming a basic skeleton via the combination of at least three heterocyclic groups having three rings. More particularly, the heterocyclic compound according to an embodiment of the present disclosure includes one of the nitrogen-containing tricycle represented by Formula 1 and at least two heterocycles having three rings, represented by Formula 2 or Formula 3.

In the heterocyclic compound according to an embodiment of the present disclosure, the tricycle represented by Formula 2 or Formula 3 is combined at a specific site in the nitrogen-containing tricycle represented by Formula 1. More particularly, the tricycle represented by Formula 2 or Formula 3 is each independently combined with at least two of $Z_1$, $Z_3$, $Z_6$ or $Z_8$ of Formula 1. Due to the structure, a single bond connecting Formula 1 with Formula 2 or Formula 3 is torsioned to have high triplet energy. Accordingly, the heterocyclic compound according to an embodiment of the present disclosure may be efficiently used as a material for emitting phosphorescence or thermally activated delayed fluorescence.

In Formula 1, if X is a direct linkage, Formula 1 may have a carbazole core structure. If X is a direct linkage, a torsional angle of a single bond connecting Formula 1 with Formula 2 or Formula 3 may be about 50 degrees or more. If X is a direct linkage, the torsional angle of a single bond connecting Formula 1 with Formula 2 or Formula 3 may be from about 50 degrees to about 90 degrees, without limitation. If the torsional angle of the single bond satisfies the above numerical range, high triplet energy may be maintained, while attaining the highest occupied molecular orbital (HOMO) energy level which may maintain excellent hole injection/transport properties.

In Formula 1, if X is $CR_2R_3$, Formula 1 may have an acridine core structure. If X is $CR_2R_3$, the torsional angle of a single bond connecting Formula 1 with Formula 2 or Formula 3 may be about 70 degrees or more. If X is $CR_2R_3$, the torsional angle of a single bond connecting Formula 1 with Formula 2 or Formula 3 may be from about 70 degrees to about 90 degrees. For example, the torsional angle of a single bond connecting Formula 1 with Formula 2 or Formula 3 may be from about 80 degrees to about 90 degrees.

Figure 3:
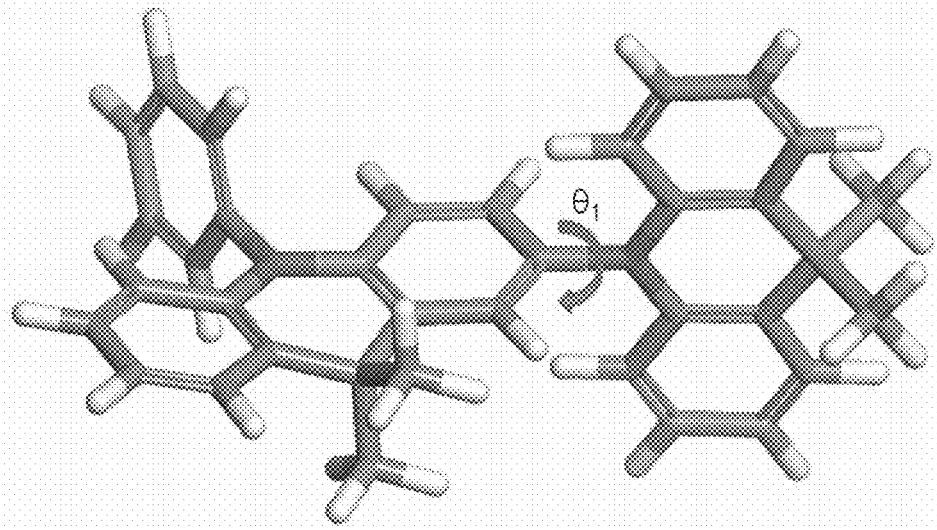
FIG. 3 is an embodiment showing a torsional angle in a compound structure.

FIG. 3 is an embodiment showing a torsional angle in a compound structure. If X of Formula 1 is $CR_2R_3$, FIG. 3 shows a measured angle of a torsional angle (θ1) of a single bond connecting Formula 1 and Formula 3, and θ1 is about 86.6 degrees.

If the torsional angle of the single bond satisfies the above numerical range, high triplet energy may be maintained, and at the same time, the highest occupied molecular orbital (HOMO) energy level which may maintain excellent hole injection/transport properties may be attained.

Figure 4:
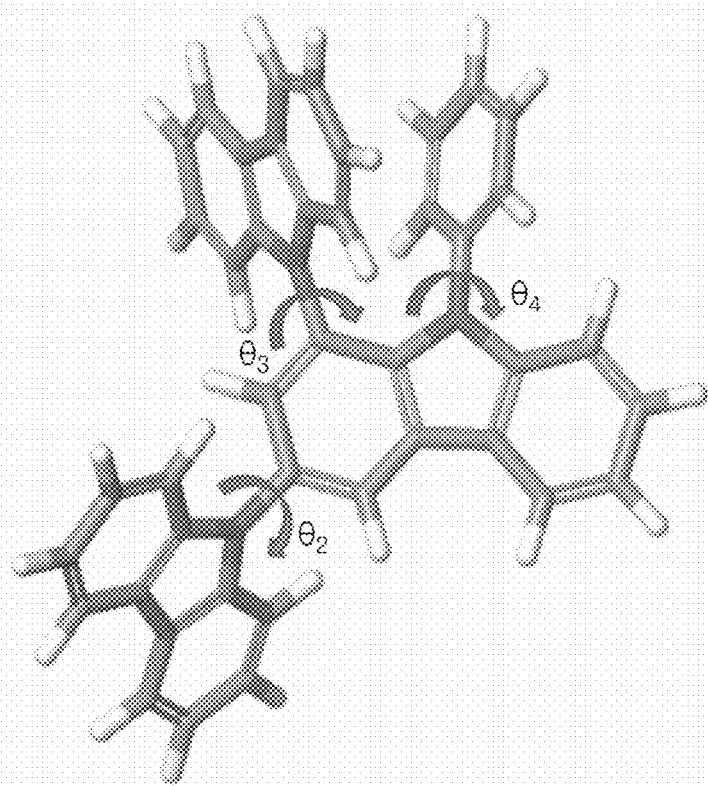
FIG. 4 is an embodiment showing a torsional angle in a compound structure.

The core structure of Formula 1 is a planar structure, and each core structure of Formula 2 or Formula 3 is also a planar structure. Referring to FIG. 4, "torsional angle" may mean the torsioned angle of two cores of in planar structures. For example, in FIG. 4, θ2 is about 52.9 degrees, θ3 is about 71.9 degrees, and θ4 is about 64.9 degrees.

In the present disclosure, "torsional angle" is a value calculated using the known method of Gaussian09 DFT B3LYP/6-31G*.

The heterocyclic compound according to an embodiment of the present disclosure may control the torsional angle by introducing various substituents into a base core structure. For example, in Formula 1, if $Z_2$ is $CR_4$, and $Z_1$ and $Z_3$ are $CR_5$, the torsional angle may be controlled by introducing a substituent other than a hydrogen atom into $R_4$, and introducing a substituent other than a hydrogen atom to an adjacent carbon to $R_4$ in Formula 2 or Formula 3.

In Formula 1, each of $Z_1$ and $Z_3$ may independently be represented by $CR_5$. For example, Formula 1 may be represented by the following Formula 1-1:

[Formula 1-1]

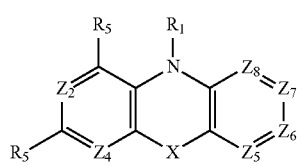

In Formula 1-1, two $R_5$ groups may be the same or different. $R_1$, $R_5$, X, $Z_2$ and $Z_4$ to $Z_8$ are the same as described above.

In Formula 1-1, each of $Z_6$ and $Z_8$ may independently be $CR_4$ wherein $R_4$ is a hydrogen atom or represented by $CR_5$ or one of the following structures:

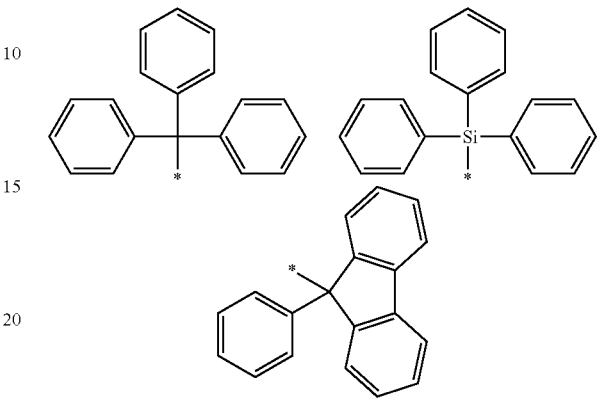

Each of the above structures may be substituted or unsubstituted. Meanwhile, the above structures are embodiments, and an embodiment of the present disclosure is not limited thereto.

In Formula 1, if a bulky substituent having a relatively large volume is introduced into $R_1$ so as to be applied in an emission layer of an organic electroluminescence device, the formation of an excimer due to intramolecular attraction may be prevented, thereby increasing the efficiency of an organic electroluminescence device. For example, $R_1$ may be a substituted or unsubstituted phenyl group, or a substituted or unsubstituted heterocycle including at least one N as a heteroatom. For example, $R_1$ may be a substituted or unsubstituted phenyl group, a substituted or unsubstituted pyridine group, or a substituted or unsubstituted carbazole group. Formula 1 may be represented by the following Formula 4, without limitation:

[Formula 4]

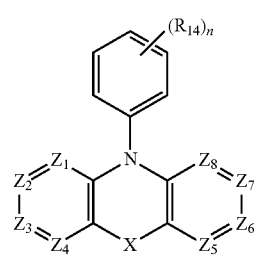

In Formula 4, $R_{14}$ is a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring, "n" is an integer of 0 to 5, and if "n" is 2 or more, a plurality of $R_{14}$ groups may be the same or different, and X and $Z_1$ to $Z_8$ are the same as described above.

In Formula 4, if "n" is 2 or more, a plurality of adjacent $R_{14}$ groups are combined with each other to form a ring. For example, a hydrocarbon ring or a heterocycle may be formed.

In Formula 4, "n" may be 0 or 1, and $R_{14}$ may be a substituted or unsubstituted aryl silyl group, a substituted or unsubstituted alkyl group having 1 or 2 carbon atoms, or a substituted or unsubstituted aryl group having 6 to 30 carbon atoms for forming a ring.

In Formula 1, $R_1$ may be represented by one of the following structures, without limitation:

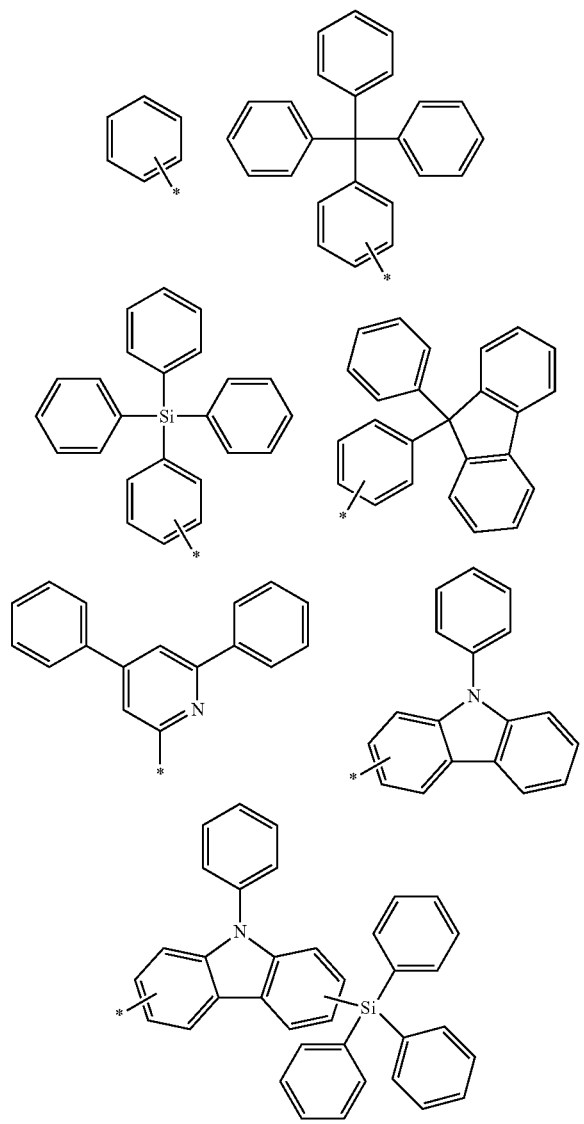

The above structures may be substituted or unsubstituted.

The heterocyclic compound according to an embodiment of the present disclosure may be used as a p-type host material, an n-type host material, or a bipolar host material according to the kind of a substituent, the existence or nonexistence of a heteroatom, etc.

For example, in Formula 2, if Y is $SO_2$, or at least one of $W_1$ to $W_8$ is N, the heterocyclic compound may be used as an n-type host material, without limitation. In another embodiment, in Formula 3, at least one of $U_1$ to $U_8$ may be N.

In Formula 1, $Z_1$ and $Z_8$, or $Z_3$ and $Z_6$ may be $CR_6$, and $R_5$ may be represented by Formula 3 so as to be used as the n-type host material. If $Z_1$ and $Z_8$ are $CR_6$, at least one of $Z_3$ and $Z_6$ may be N, and if $Z_3$ and $Z_6$ are $CR_6$, at least one of $Z_1$ and $Z_8$ may be N. In this case, relatively low energy of the lowest unoccupied molecular orbital (LUMO) may be attained. In Formula 3, Q may be O, and at least one of $U_2$ to $U_7$ may be N, and if the conditions are satisfied, relatively low energy of the LUMO, and relatively high triplet energy may be attained at the same time.

In Formula 2, if Y is a direct linkage, Formula 2 may have a carbazole core structure. In Formula 2, Y may be a direct linkage and all $W_1$ to $W_8$ may be $CR_{11}$. In Formula 2, Y may be a direct linkage, and at least one of $W_1$, $W_3$, $W_6$ and $W_8$ may be N to attain the properties of an n-type host material. However, an embodiment of the present disclosure is not limited thereto. If the above conditions are satisfied, relatively high triplet energy, and relatively low energy the LUMO may be attained.

In another embodiment, in Formula 2, Y may be a direct linkage, and $W_1$ and $W_3$, or $W_6$ and $W_8$ may be N. In this case, triplet energy may be relatively high, and the LUMO energy may be relatively low, too. If the heterocyclic compound according to an embodiment of the present disclosure includes three carbazole moieties or three acridine moieties, it may be used as a p-type host material. However, an embodiment of the present disclosure is not limited thereto.

Formula 1 may be, for example, represented by the following Formula 5:

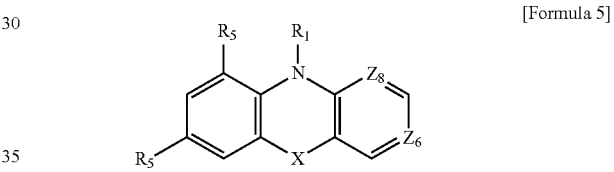

[Formula 5]

In Formula 5, $R_5$ is each independently represented by Formula 2 or Formula 3, $R_1$ is a substituted or unsubstituted phenyl group, a substituted or unsubstituted pyridine group, or a substituted or unsubstituted carbazole group, and X and $Z_6$ and $Z_8$ are the same as described above.

Formula 5 may be, for example, represented by Formula 5-1 below.

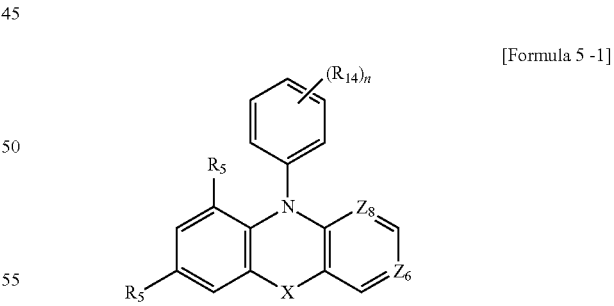

[Formula 5-1]

In Formula 5-1, $R_5$ is each independently represented by Formula 2 or Formula 3, $R_{14}$ is a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring, "n" is an integer of 0 to 5, where if "n" is 2 or more, a plurality of $R_{14}$ groups are the same or different, and X and $Z_6$ and $Z_8$ are the same as described above. If "n" is 2 or more, adjacent $R_{14}$ groups may be combined with each other to form a ring.

In Formula 5, two $R_5$ groups may be the same or different.

In Formula 5, "n" may be 0 or 1, and $R_{14}$ may be a substituted or unsubstituted aryl silyl group, a substituted or unsubstituted alkyl group having 1 or 2 carbon atoms, or a substituted or unsubstituted aryl group having 6 to 30 carbon atoms for forming a ring.

In Formula 5, "n" may be 0 or 1, and $R_{14}$ may be a triphenylsilyl group, a triphenylmethyl group, or a substituted or unsubstituted fluorenyl group.

In Formula 2, if Y is $CR_6R_7$, $R_6$ and $R_7$ are each independently a substituted or unsubstituted alkyl group having 1 to 10 carbon atoms, or a substituted or unsubstituted aryl group (aromatic hydrocarbon ring group) having 6 to 30 carbon atoms for forming a ring. For example, each of $R_6$ and $R_7$ may independently be a substituted or unsubstituted methyl group or a substituted or unsubstituted phenyl group.

In Formula 2, if Y is $NR_{10}$, $R_{10}$ may be a substituted or unsubstituted aryl group having 6 to 30 carbon atoms. For example, $R_{10}$ may be a substituted or unsubstituted phenyl group.

In Formula 3, if Q is $NR_{12}$, $R_{12}$ may be a substituted or unsubstituted aryl group having 6 to 30 carbon atoms. For example, $R_{12}$ may be a substituted or unsubstituted phenyl group.

The heterocyclic compound represented by Formula 1 according to an embodiment of the present disclosure may be one selected from the compounds represented in Compound Group 1 below. However, an embodiment of the present disclosure is not limited thereto.

[Compound Group 1]

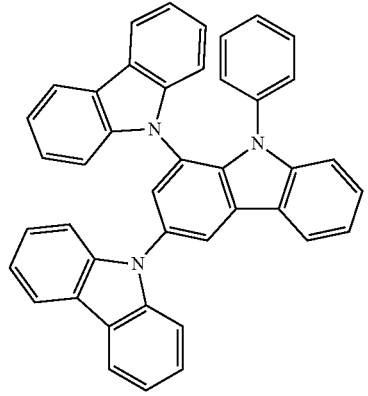

1

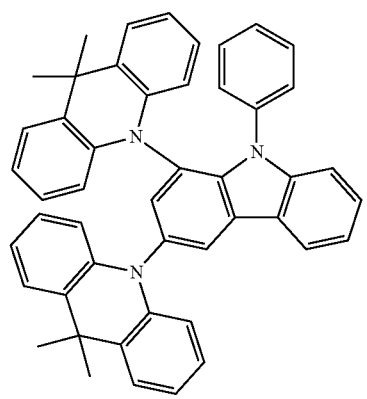

2

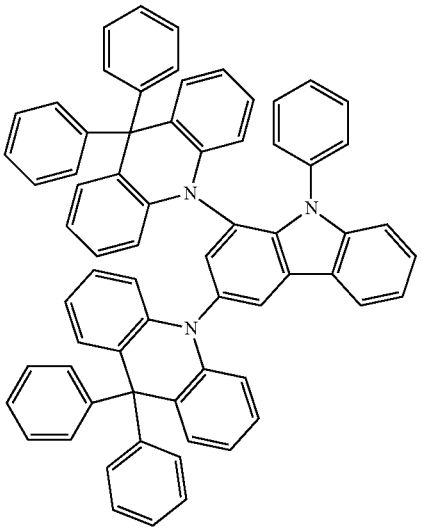

3

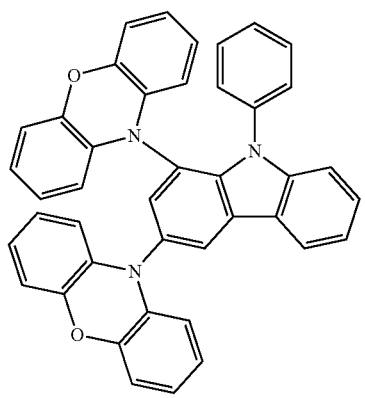

4

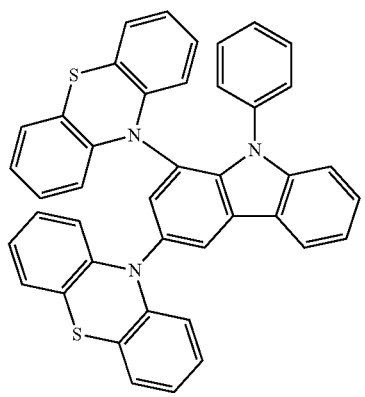

5

6
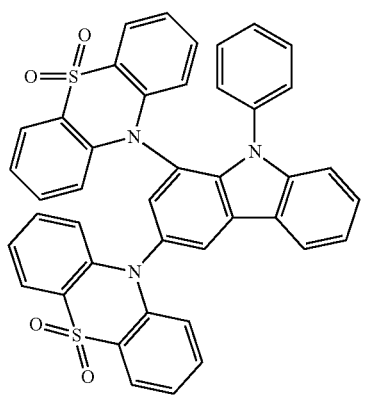
7
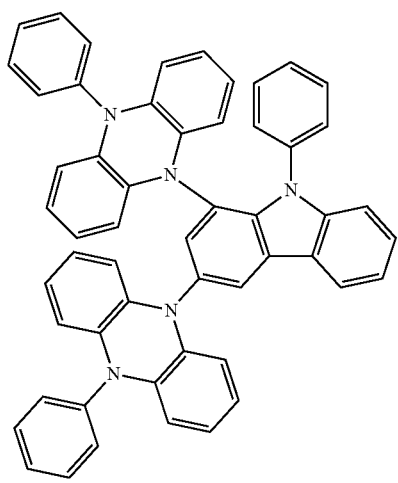
8
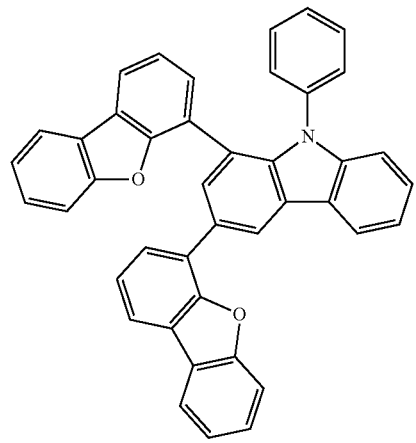
9
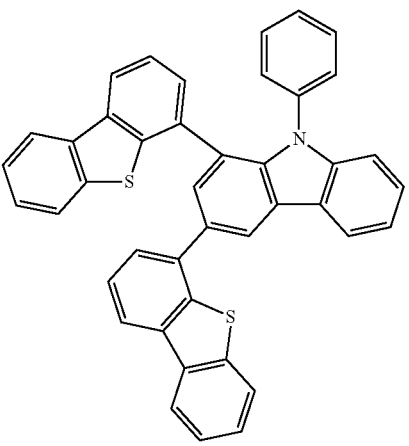
10
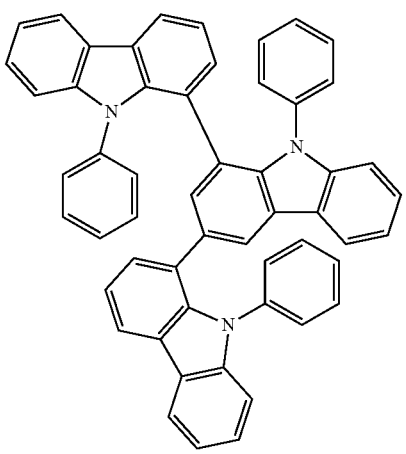
11
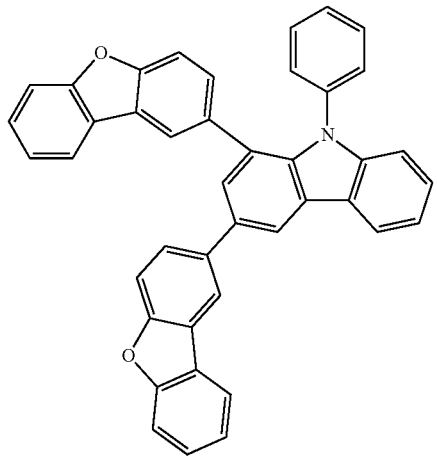

12
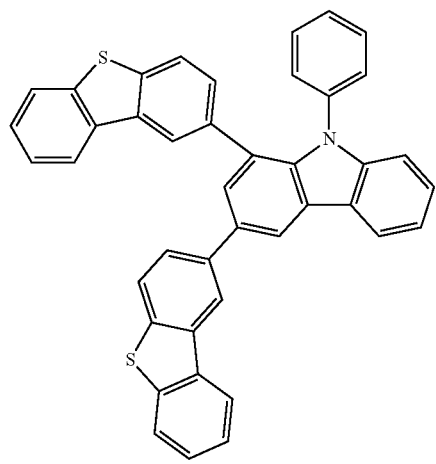
13
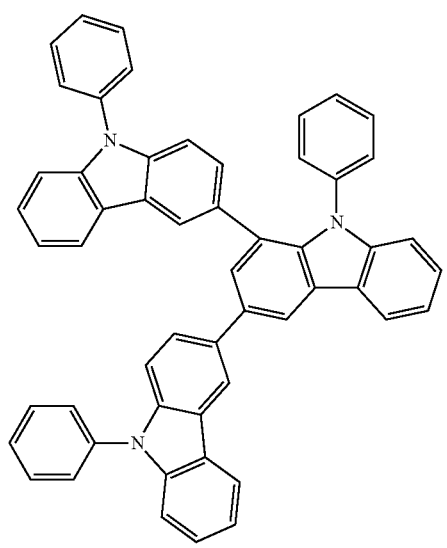
14
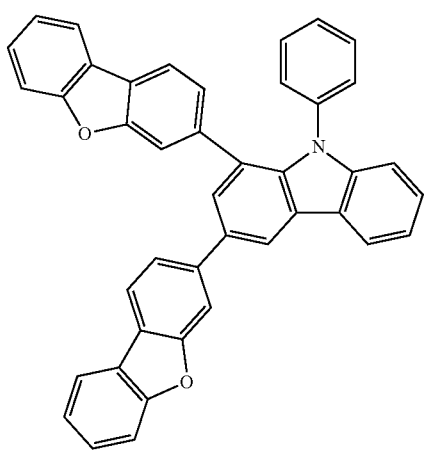
15
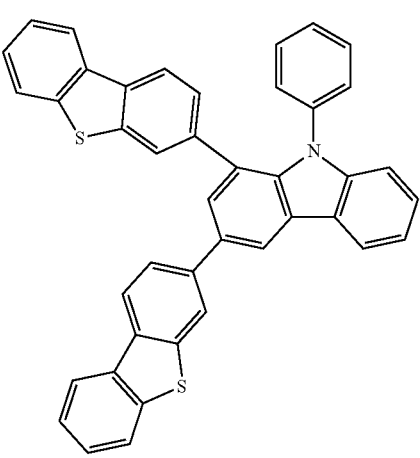
16
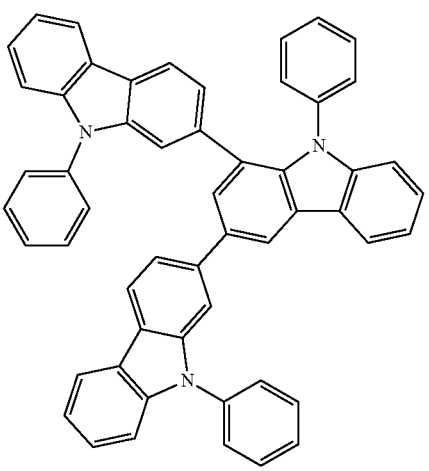
17
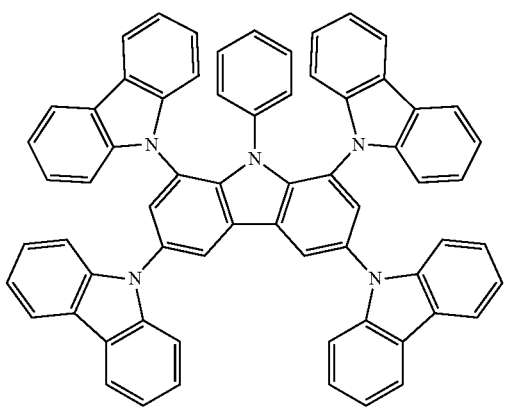

18
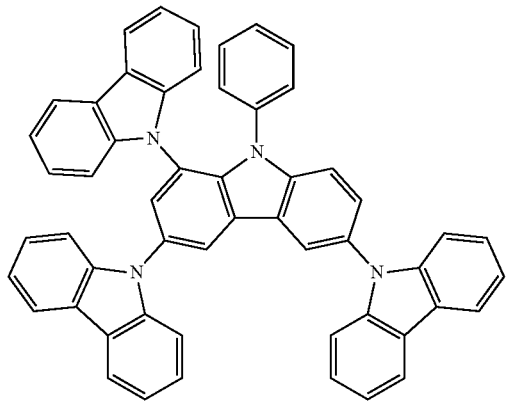
19
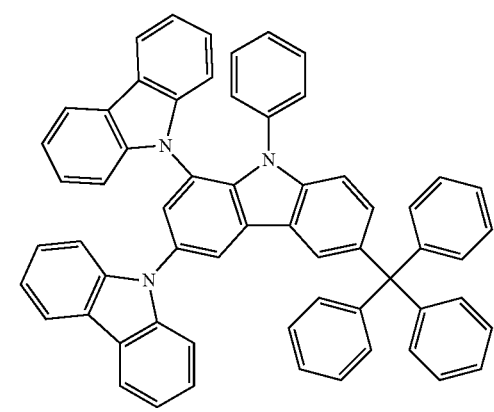
20
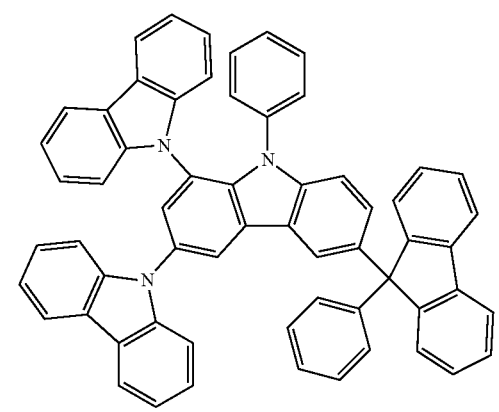
21
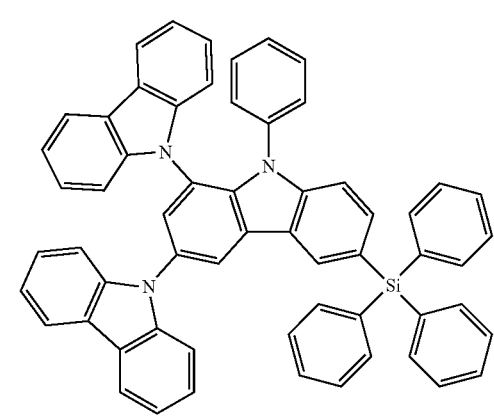
22
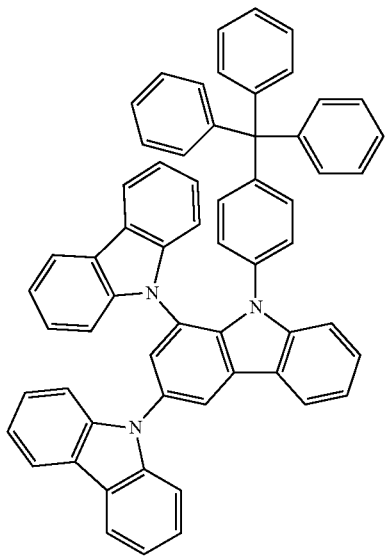
23
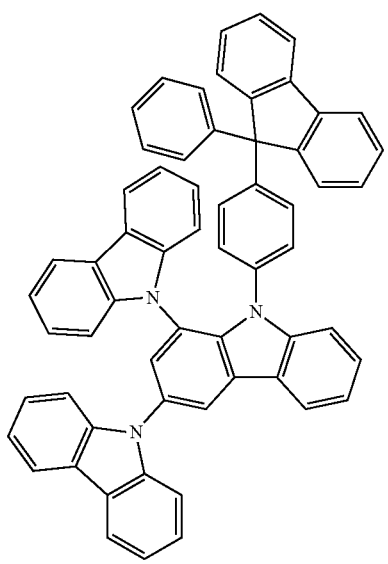
24
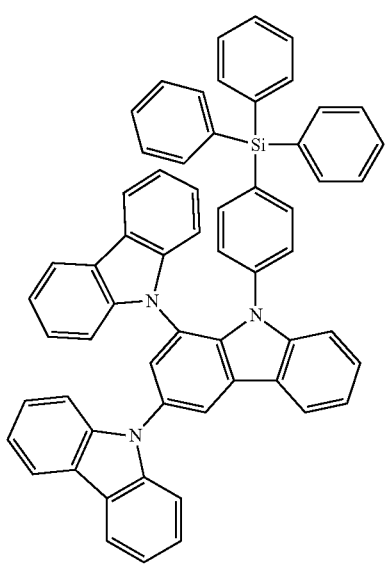

25
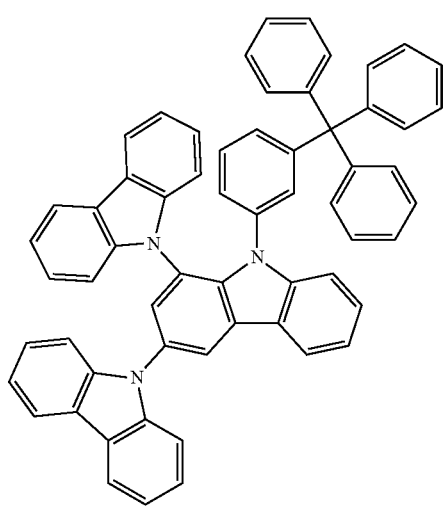
26
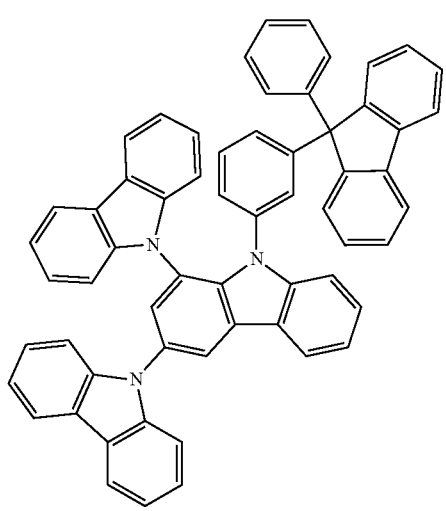
27
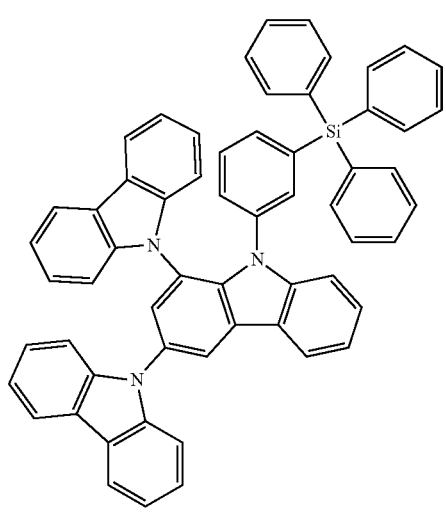
28
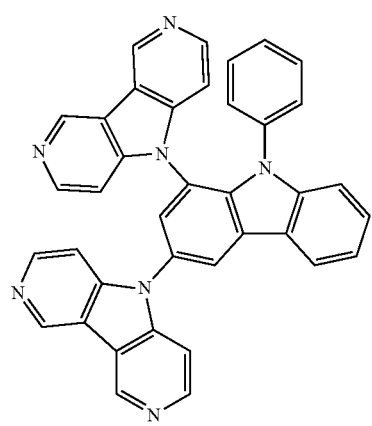
29
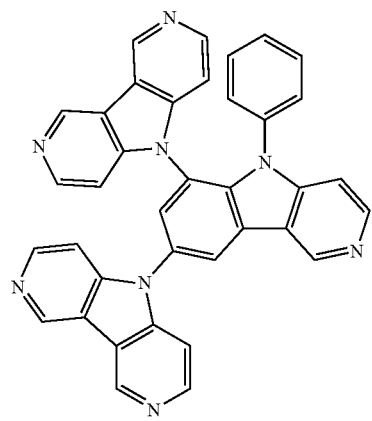
30
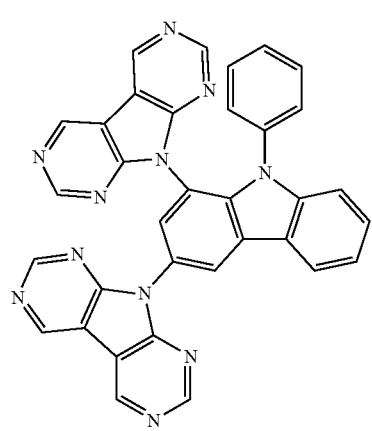

31
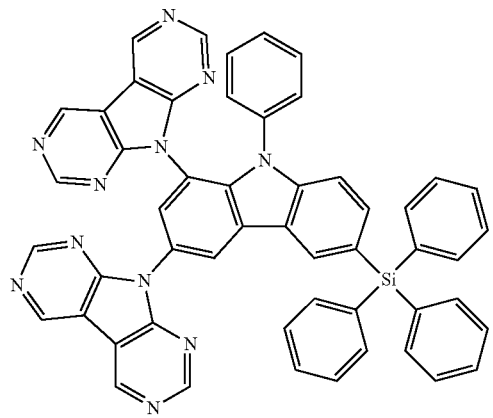
32
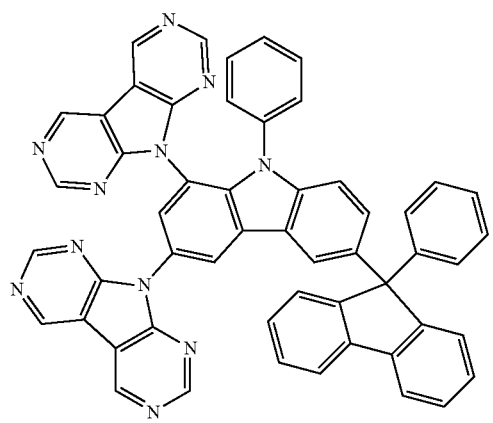
33
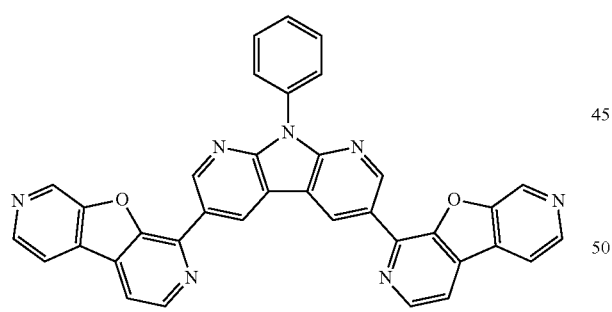
34
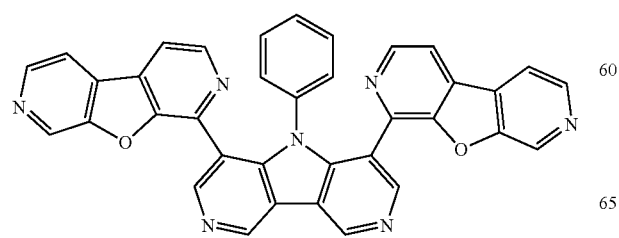
35
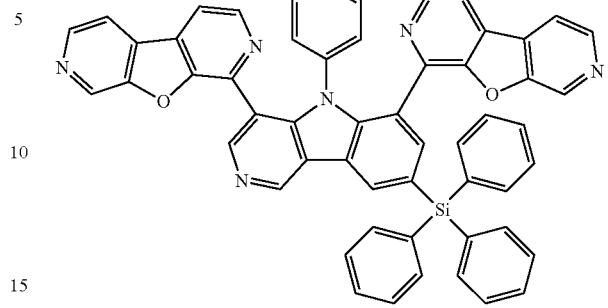
36
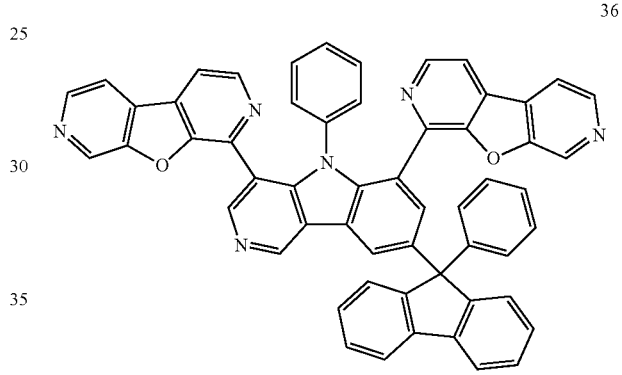
37
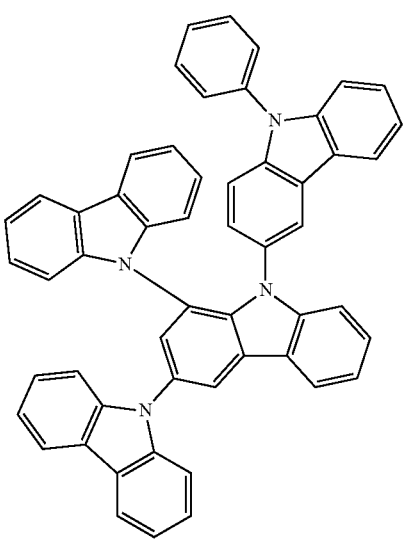

38
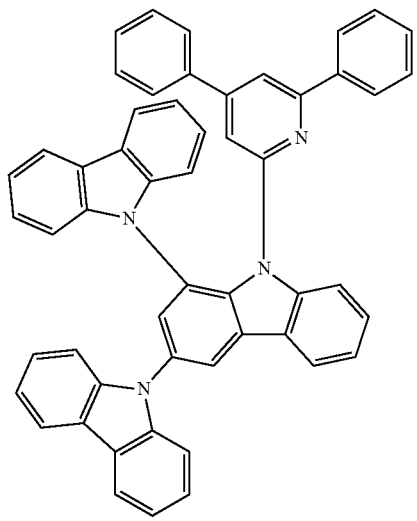
39
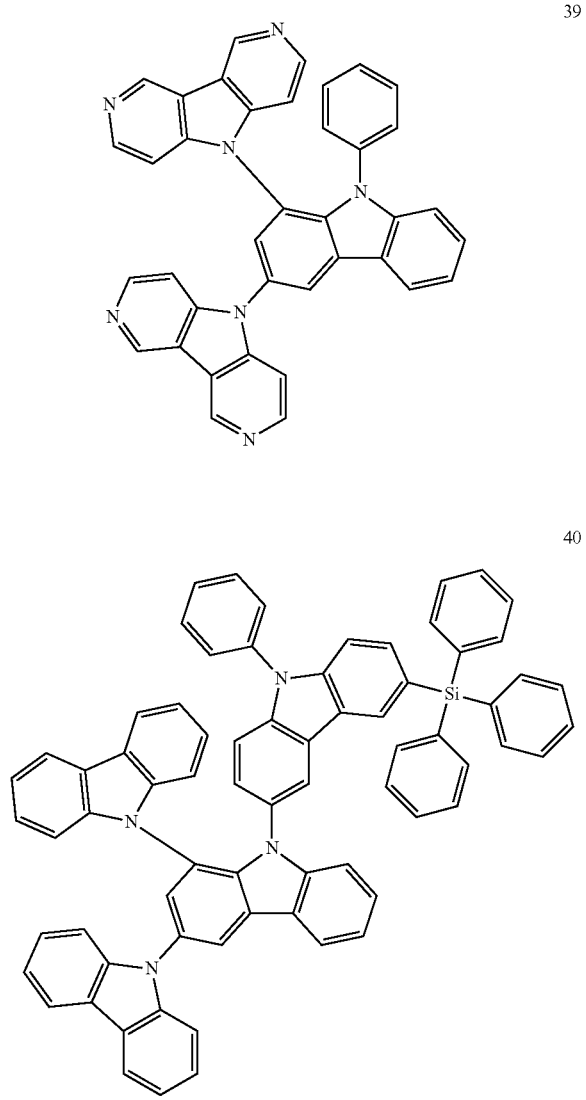
41
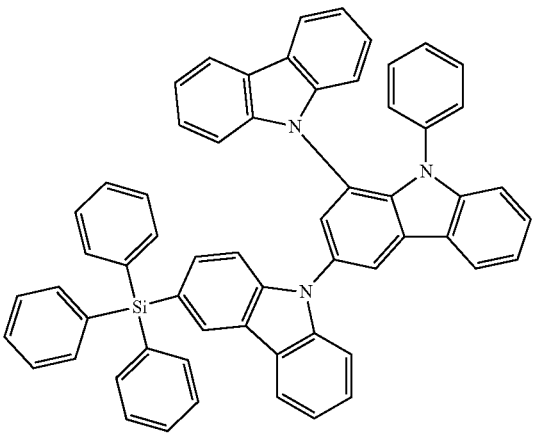
42
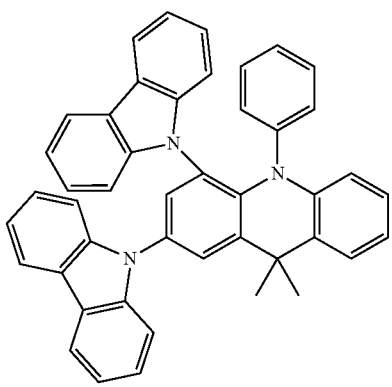
43
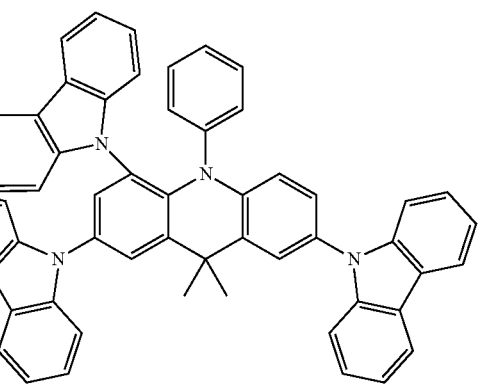
44
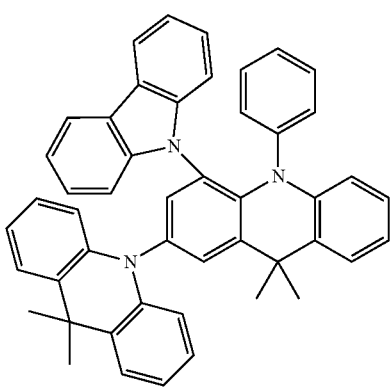

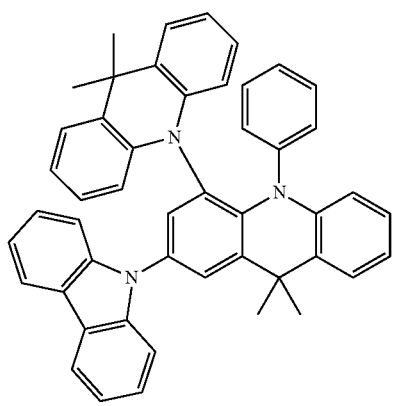

45

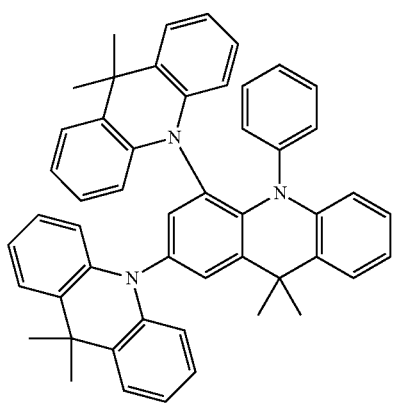

46

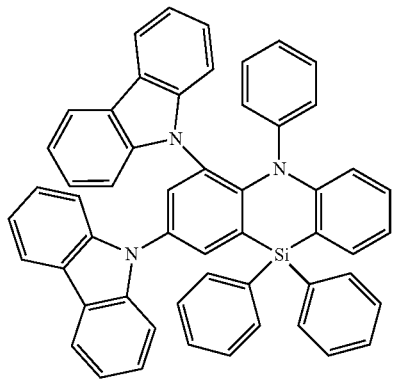

47

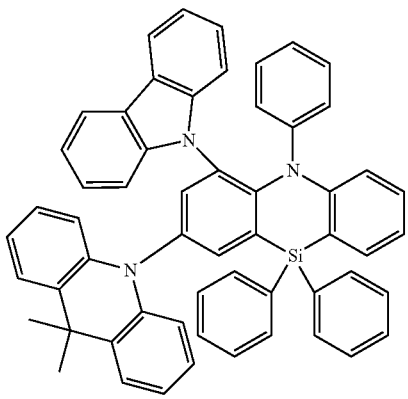

48

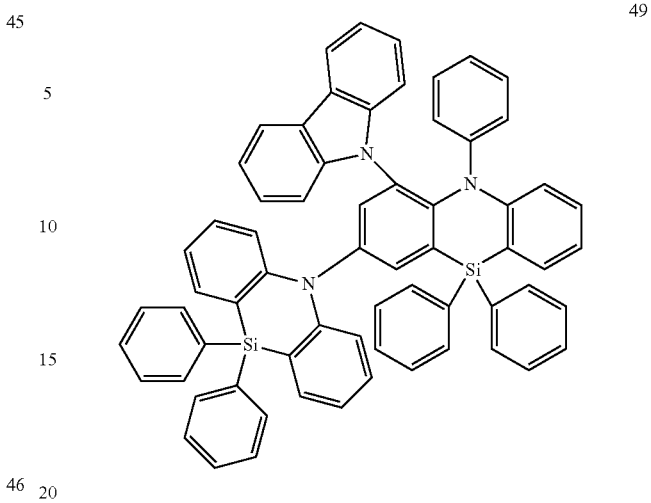

49

In the heterocyclic compound according to an embodiment of the present disclosure, at least three tricyclic structures are connected, and the compound has a torsioned structure by connecting the tricyclic structures at specific positions. Accordingly, the heterocyclic compound according to an embodiment of the present disclosure has sufficiently high triplet energy, and may be appropriately applied to a phosphorescence device. However, an embodiment of the present disclosure is not limited thereto, and the heterocyclic compound according to an embodiment of the present disclosure may be applied as a host in a thermally activated delayed fluorescence device. The heterocyclic compound according to an embodiment of the present disclosure may be applied as a blue emission host, and particularly, as a deep blue emission host.

The heterocyclic compound represented by Formula 1 may be prepared based on the synthetic examples explained below. However, the synthetic process of the heterocyclic compound represented by Formula 1 is not limited to the synthetic examples explained below, but any reaction conditions known in the art may be applied.

An embodiment of the present disclosure provides a heterocyclic compound represented by Formula A below.

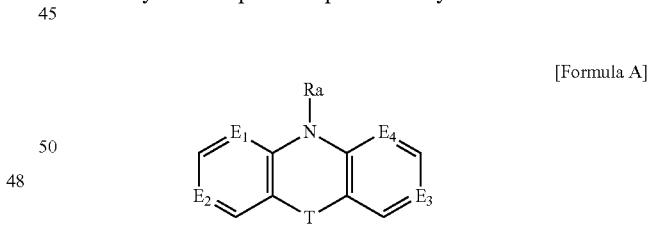

[Formula A]

In Formula A, Ra is a substituted or unsubstituted phenyl group, or a substituted or unsubstituted heterocyclic group including at least one N as a heteroatom, T is a direct linkage or CRbRc, $E_1$ to $E_4$ are each independently CRd or N, Rb to Rd are each independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring, and at least two of $E_1$ to $E_4$ are each independently CRe, and Re is a substituted or unsubstituted heterocyclic group having at least three rings.

Re may be, for example, a tricyclic heterocyclic group or a hexacyclic heterocyclic group.

Re may be, for example, represented by the above Formula 2 or Formula 3.

In Formula A, $E_1$ and $E_2$ may be CRe. In this case, each of $E_3$ and $E_4$ may independently be CRd wherein Rd is a hydrogen atom or represented by CRe, or by one of the following structures:

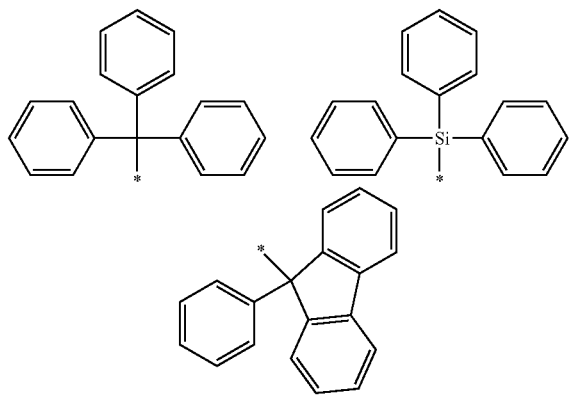

The above structures may be substituted or unsubstituted.

In Formula A, Ra may be a substituted or unsubstituted phenyl group, a substituted or unsubstituted pyridine group, or a substituted or unsubstituted carbazole group. However, an embodiment of the present disclosure is not limited thereto.

Hereinafter, an organic electroluminescence device according to an embodiment of the present disclosure will be explained. The explanation will be mainly with the difference in the heterocyclic compound according to an embodiment of the present disclosure, and unexplained part will follow the above-description on the heterocyclic compound according to an embodiment of the present disclosure.

The organic electroluminescence device according to an embodiment of the present disclosure includes the above-described heterocyclic compound according to an embodiment of the present disclosure. The organic electroluminescence device according to an embodiment of the present disclosure includes a heterocyclic compound represented by Formula 1 or a heterocyclic compound represented by Formula A.

Hereinafter, an organic electroluminescence device according to an embodiment of the present disclosure including the heterocyclic compound represented by Formula 1 will be explained as an illustration, but the heterocyclic compound represented by Formula 1 may be replaced with the heterocyclic compound represented by Formula A.

Figure 2:
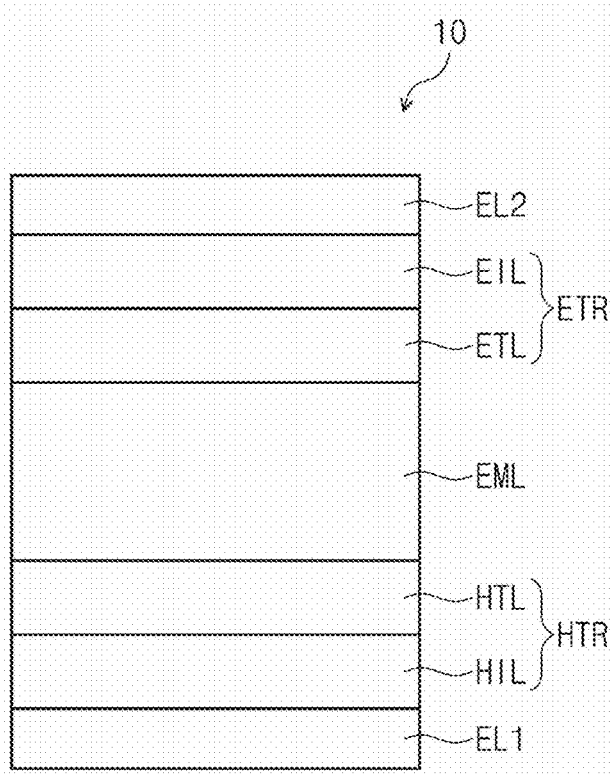
FIG. 2 is a cross-sectional view schematically illustrating an organic electroluminescence device according to an embodiment of the present disclosure.

FIG. 1 is a cross-sectional view schematically illustrating an organic electroluminescence device according to an embodiment of the present disclosure. FIG. 2 is a cross-sectional view schematically illustrating an organic electroluminescence device according to an embodiment of the present disclosure.

Referring to FIGS. 1 and 2, an organic electroluminescence device 10 according to an embodiment of the present disclosure includes a first electrode EL1, a hole transport region HTR, an emission layer EML, an electron transport region ETR, and a second electrode EL2.

The first electrode EL1 and the second electrode EL2 are oppositely disposed, and between the first electrode EL1 and the second electrode EL2, a plurality or organic layers may be disposed. The plurality of organic layers may include a hole transport region HTR, an emission layer EML, and an electron transport region ETR.

The organic electroluminescence device 10 according to an embodiment of the present disclosure may include the heterocyclic compound according to an embodiment of the present disclosure in at least one of the plurality of organic layers disposed between the first electrode EL1 and the second electrode EL2.

Hereinafter, an embodiment of including the heterocyclic compound according to an embodiment of the present disclosure in an emission layer EML will be explained as an illustration. However, an embodiment of the present disclosure is not limited thereto and, for example, a hole transport region HTR may include the heterocyclic compound according to an embodiment of the present disclosure.

The first electrode EL1 has conductivity. The first electrode EL1 may be a pixel electrode or an anode. The first electrode EL1 may be a transmissive electrode, a transflective electrode, or a reflective electrode. If the first electrode EL1 is the transmissive electrode, the first electrode EL1 may include a transparent metal oxide such as indium tin oxide (ITO), indium zinc oxide (IZO), zinc oxide (ZnO), or indium tin zinc oxide (ITZO). If the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a plurality of layers including a reflective layer or a transflective layer formed using the above materials, or a transparent conductive layer formed using ITO, IZO, ZnO, ITZO, etc. For example, the first electrode EL1 may have a three-layer structure of ITO/Ag/ITO, without limitation.

The thickness of the first electrode EL1 may be from about 1,000 Å to about 10,000 Å. In one embodiment, for example, the thickness of the first electrode EL1 may be from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer. The thickness of the hole transport region HTR may be, for example, from about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In addition, the hole transport region HTR may have a single layer structure formed using a plurality of different materials, or a structure laminated one by one from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using various methods such as a vacuum deposition method, a spin coating method, a cast method, a Langmuir-Blodgett (LB)

method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4',4"-tris(N,N-diphenylamino)triphenylamine (TDATA), 4,4',4"-tris {N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL may include, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris (N-carbazolyl)triphenylamine (TCTA), N,N'-di(naphthylene-1-yl)-N,N'-diphenyl-benzidine (NPB), 4,4'-cyclohexylidene bis[N,N-bis(4-methylphenyl)benzenamine](TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å. In one embodiment, the hole transport region HTR may be from about 100 Å to about 1,000 Å. If the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. If the thicknesses of the hole transport region HTR, the hole injection layer HIL, and the hole transport layer HTL satisfy the above-described ranges, satisfactory hole transport properties may be obtained without the substantial increase of a driving voltage.

The hole transport region HTR may further include a charge generating material to improve conductivity in addition to the above-described materials. The charge generating material may be uniformly or non-uniformly dispersed in the hole transport region HTR. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ), and 2,3,5,6-tetrafluoro-tetracyanoquinodimethane (F4-TCNQ), and metal oxides such as tungsten oxide, and molybdenum oxide, without limitation.

As described above, the hole transport region HTR may further include one of a hole buffer layer or an electron blocking layer in addition to the hole injection layer HIL and the hole transport layer HTL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer is a layer preventing electron injection from the electron transport region ETR to the hole transport region HTR.

The emission layer EML is provided on the hole transport region HTR. The emission layer EML may have a thickness of, for example, about 100 Å to about 1,000 Å, or about 100 Å to about 300 Å. The emission layer EML may have a single layer formed using a single material, a single layer formed using a plurality of different materials, or a multilayer structure having a plurality of layers formed using a plurality of different materials.

The emission layer EML may include the heterocyclic compound according to an embodiment of the present disclosure. Particularly, the emission layer EML may include a heterocyclic compound represented by Formula 1 below.

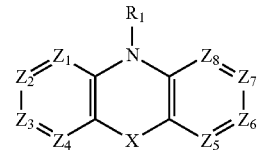

[Formula 1]

In Formula 1, particular explanation on $R_1$, X, and $Z_1$ to $Z_8$ is the same as described above, and will be omitted.

The emission layer EML may include one or two or more kinds of the heterocyclic compounds represented by Formula 1. The emission layer EML may further include a known material in addition to the heterocyclic compound represented by Formula 1. For example, the emission layer EML may further include a fluorescent material including any one selected from the group consisting of spiro-DPVBi, 2,2',7,7'-tetrakis(biphenyl-4-yl)-9,9'-spirobifluorene (spiro-6P, spiro-sexiphenyl), distyryl-benzene (DSB), distyrylarylene (DSA), a polyfluorene (PFO)-based polymer, and a poly(p-phenylene vinylene) (PPV)-based polymer. For example, the emission layer EML may include an anthracene-based compound, an arylamine-based compound, or a styryl-based compound. In addition, the emission layer EML may include a known phosphorescence material.

The emission layer EML may include a host or a dopant. The host may include the heterocyclic compound according to an embodiment of the present disclosure. The host may be a phosphorescence host or a thermally activated delayed fluorescence host. That is, the heterocyclic compound according to an embodiment of the present disclosure may be used as a fluorescence host or a thermally activated delayed fluorescence host.

The emission layer EML may be a blue emission layer which emits blue light, for example, a deep blue emission layer. That is, the heterocyclic compound according to an embodiment of the present disclosure may emit blue light having a wavelength region less than about 470 nm, for example, from about 440 nm to about 460 nm, or from about 440 nm to about 450 nm.

The emission layer EML may further include a host in addition to the heterocyclic compound according to an embodiment of the present disclosure. Here, the host may include commonly used materials without specific limitation, and may include, for example, tris(8-hydroxyquinolino)aluminum (Alq3), 4,4'-bis(N-carbazolyl)-1,1'-biphenyl (CBP), poly(n-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl) benzene (TPBi), 3-tert-butyl-9,10-di(naphth-2-yl) anthracene (TBADN), distyrylarylene (DSA), 4,4'-bis(9-carbazolyl)-2,2'-dimethyl-biphenyl (CDBP), 2-methyl-9,10- bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetra siloxane (DPSiO$_4$), 2,8-bis(diphenylphosphoryl)dibenzofuran (PPF), etc.

The dopant may include an organometal complex including a transition metal (for example, iridium (Ir), platinum (Pt), osmium (Os), rhodium (Rh), etc.). The dopant may include, for example, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), bis-(1-phenylisoquinolyl)iridium(III) acetylacetonate (Ir(ppy)$_3$), Ir(dpbic)$_3$, etc.

The electron transport region ETR is provided on the emission layer EML. The electron transport region ETR may include at least one of a hole blocking layer, an electron transport layer ETL, or an electron injection layer EIL, without limitation.

The electron transport region ETR may have a single layer formed using a single material, a single layer formed using a plurality of different materials, or a multilayer structure including a plurality of layers formed using a plurality of different materials.

For example, the electron transport region ETR may have a single layer structure of an electron injection layer EIL or an electron transport layer ETL, or a single layer structure formed using an electron injection material and an electron transport material. In addition, the electron transport region ETR may have a single layer structure formed using a plurality of different materials, or a structure laminated one by one from the first electrode EL1 of electron transport layer ETL/electron injection layer EIL, or hole blocking layer/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes the electron transport layer ETL, the electron transport region ETR may include an anthracene-based compound. The electron transport region ETR may include, for example, tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq2), 9,10-di(naphthalene-2-yl)anthracene (ADN), or a mixture thereof, without limitation. The thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without the substantial increase of a driving voltage.

If the electron transport region ETR includes the electron injection layer EIL, the electron transport region ETR may include LiF, lithium quinolate (LiQ), Li$_2$O, BaO, NaCl, CsF, a metal in lanthanoides such as Yb, or a metal halide such as RbCl and RbI, without limitation. The electron injection layer EIL may be also formed using a mixture material of an electron transport material and an insulating organo metal salt. The organo metal salt may be a material having an energy band gap of about 4 eV or more. Particularly, the organo metal salt may include, for example, a metal acetate, a metal benzoate, a metal acetoacetate, a metal acetylacetonate, or a metal stearate. The thickness of the electron injection layer EIL may be from about 1 Å to about 100 Å, and from about 3 Å to about 90 Å. If the thickness of the electron injection layer EIL satisfies the above described range, satisfactory electron injection properties may be obtained without inducing the substantial increase of a driving voltage.

The electron transport region ETR may include a hole blocking layer, as described above. The hole blocking layer may include, for example, at least one of 2,9-dimethyl-4,7-diphenyl-1,10-phenanthroline (BCP), or 4,7-diphenyl-1,10-phenanthroline (Bphen), without limitation.

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may be formed using a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials, and a transparent conductive layer formed using ITO, IZO, ZnO, ITZO, etc.

Even not shown, the second electrode EL2 may be connected with an auxiliary electrode. If the second electrode EL2 is connected with the auxiliary electrode, the resistance of the second electrode EL2 may be decreased.

In the organic electroluminescence device 10, according to the application of voltages to each of the first electrode EL1 and the second electrode EL2, holes injected from the first electrode EL1 move via the hole transport region HTR to the emission layer EML, and electrons injected from the second electrode EL2 move via the electron transport region ETR to the emission layer EML. The electrons and holes are recombined in the emission layer EML to generate excitons, and the excitons may emit light via transition from an excited state to a ground state.

If the organic electroluminescence device 10 is a top emission type, the first electrode EL1 may be a reflective electrode, and the second electrode EL2 may be a transmissive electrode or a transflective electrode. If the organic electroluminescence device 10 is a bottom emission type, the first electrode EL1 may be a transmissive electrode or a transflective electrode, and the second electrode EL2 may be a reflective electrode.

The organic electroluminescence device according to an embodiment of the present disclosure is characterized by including the heterocyclic compound represented by Formula 1 or the heterocyclic compound represented by Formula A and may achieve high efficiency, long life and a low driving voltage.

Hereinafter, the present disclosure will be explained more particularly referring to preferred embodiments and comparative embodiments. The following embodiments are only for illustration to assist the understanding of the present disclosure, but the scope of the present disclosure is not limited thereto.

SYNTHETIC EXAMPLES

The heterocyclic compound according to an embodiment of the present disclosure may be synthesized, for example, as follows. However, the synthetic method of the heterocyclic compound according to an embodiment of the present disclosure is not limited thereto.

1. Synthesis of Compound 37

Compound 37 may be synthesized, for example, by the method described below.

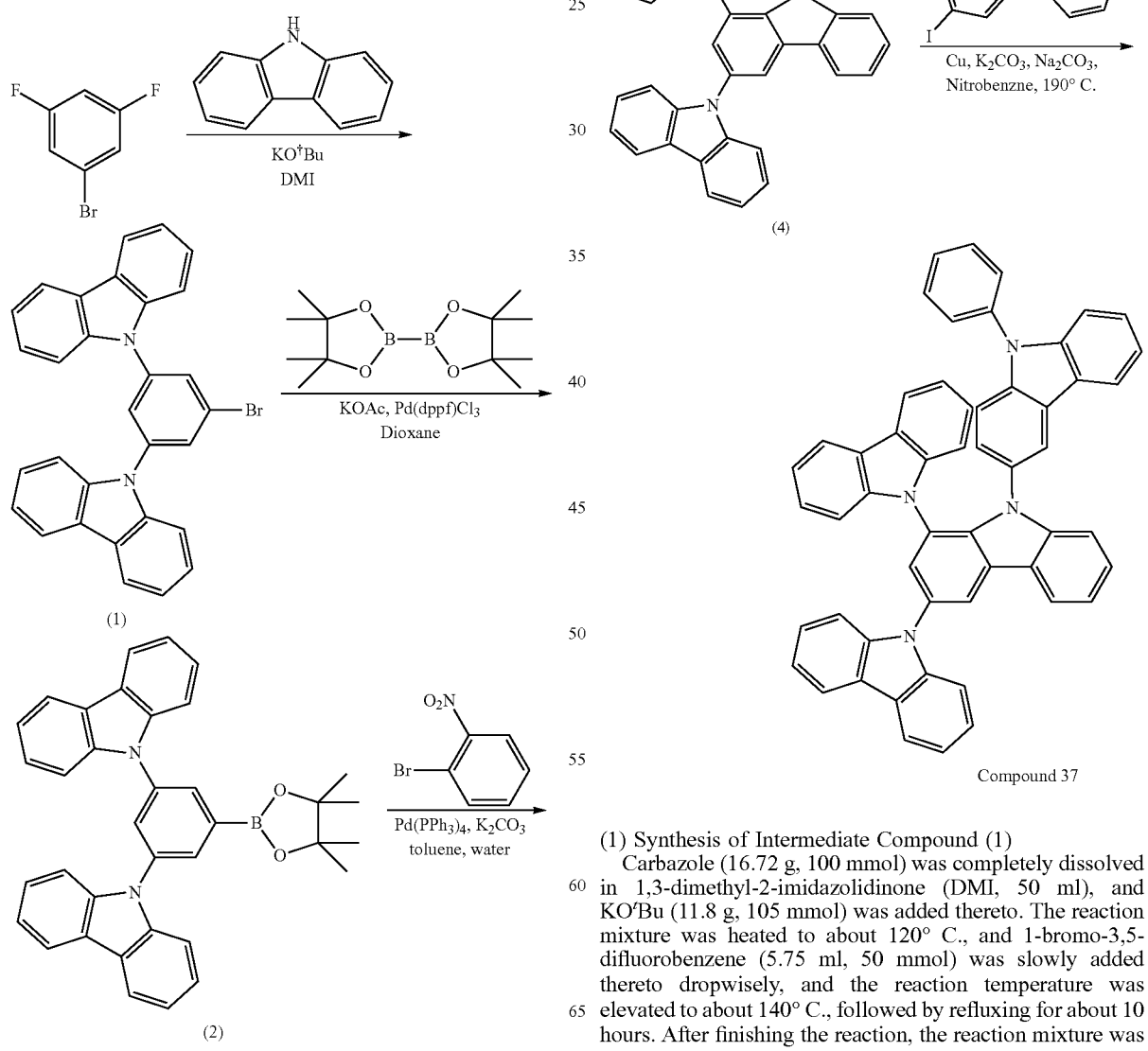

(1) Synthesis of Intermediate Compound (1)

Carbazole (16.72 g, 100 mmol) was completely dissolved in 1,3-dimethyl-2-imidazolidinone (DMI, 50 ml), and KO$^t$Bu (11.8 g, 105 mmol) was added thereto. The reaction mixture was heated to about 120° C., and 1-bromo-3,5-difluorobenzene (5.75 ml, 50 mmol) was slowly added thereto dropwisely, and the reaction temperature was elevated to about 140° C., followed by refluxing for about 10 hours. After finishing the reaction, the reaction mixture was cooled to room temperature, and the reaction mixture was poured into ice water (500 ml), followed by stirring for about 30 minutes. The solid thus formed was filtered using a glass filter and washed with distilled water many times and then, with EtOH (500 ml). The solid thus obtained was dried in vacuum to obtain Intermediate Compound (1) (21.3 g, 87%). $^1$H NMR (300 MHz, CDCl$_3$): δ ppm 8.13 (d, 4H), 7.84 (s, 2H), 7.77 (s, 1H), 7.53 (d, 4H), 7.44 (t, 4H), 7.32 (t, 4H).

(2) Synthesis of Intermediate Compound (2)

Intermediate Compound (1) (16.4 g, 33.6 mmol), bis(pinacolato)diboron (17.1 g, 67.2 mmol), and potassium acetate (32.97 g, 336 mmol) were dissolved in 1,4-dioxane (200 ml), followed by stirring under a nitrogen atmosphere at about 60° C. for about 15 minutes. To the reaction mixture, Pd(dppf)CH$_2$Cl$_2$ (0.82 g, 1.0 mmol) was added and stirred at about 80° C. for about 14 hours. The reaction mixture was cooled to room temperature, extracted with toluene, dried with MgSO$_4$ to remove water, and separated by column chromatography (n-hexane:dichloromethane (MC)=1:3, v/v) to obtain Intermediate Compound (2) (11.76 g, yield: 65%). $^1$H NMR (300 MHz, CDCl$_3$): δ ppm 8.17-8.11 (m, 6H), 7.87 (s, 1H), 7.54-7.40 (m, 9H), 7.34-7.30 (m, 3H), 1.36 (s, 12H).

(3) Synthesis of Intermediate Compound (3)

Intermediate Compound (2) (11.76 g, 22 mmol) and 1-bromo-2-nitrobenzene (3.68 g, 18.2 mmol) were dissolved in dioxane/toluene (30 ml/30 ml), and to the reaction mixture, K$_2$CO$_3$ (7.6 g, 55 mmol) and distilled water (10 ml) were added, followed by stirring in a nitrogen atmosphere for about 20 minutes. Then, Pd(PPh$_3$)$_4$(O) (0.8 g, 0.69 mmol) was added thereto, and the reaction mixture was stirred at about 80° C. for about 12 hours. After finishing the reaction, the reaction temperature was decreased to room temperature, and the reaction product was extracted with ethyl acetate (EA) (100 ml), dried with MgSO$_4$ to remove water, and separated by column chromatography (n-hexane:EA=10:1, v/v) to obtain Intermediate Compound (3) (8.02 g, yield 69%). $^1$H NMR (300 MHz, DMSO-d$_6$): ppm 8.77 (d, 1H), 8.42 (d, 1H), 8.33 (d, 2H), 8.26 (d, 2H), 7.65 (d, 1H), 7.59-7.55 (m, 2H), 7.52-7.43 (m, 6H), 7.37-7.25 (m, 7H).

(4) Synthesis of Intermediate Compound (4)

Under a nitrogen atmosphere, Intermediate Compound (3) (9.9 g, 37.8 mmol), PPh$_3$ (7.92 g, 30.2 mmol) and o-dichlorobenzene (80 ml) were mixed, followed by stirring at about 185° C. for about 12 hours. Then, reaction solvents were removed via distillation, and the reaction product was extracted with EA (100 ml), dried with MgSO$_4$ to remove water, separated by column chromatography (n-hexane:EA=10:1, v/v), and washed with MeOH to obtain Intermediate Compound (4) (5.04 g, yield 67%). $^1$H NMR (300 MHz, DMSO-d$_6$): ppm 11.33 (s, 1H), 8.65 (d, 1H), 8.45-8.18 (m, 5H), 7.69 (d, 1H), 7.52-7.43 (m, 8H), 7.36-7.23 (m, 7H).

(5) Synthesis of Compound 37

Under a nitrogen atmosphere, Intermediate Compound (4) (3.0 g, 6.03 mmol), 3-iodo-9-phenyl-9H-carbazole (3.3 g, 9.04 mmol), Cu (0.038 g, 0.603 mmol), K$_2$CO$_3$ (0.83 g, 6.03 mmol), Na$_2$CO$_3$ (0.64 g, 6.03 mmol) and nitrobenzene (20 ml) were mixed, followed by stirring at about 195° C. for about 18 hours. Then, reaction solvents were removed via distillation, and an organic layer was separated using EA (100 ml), dried with MgSO$_4$ to remove water, and separated by column chromatography (n-hexane:dichloromethane=10:1, v/v) to finally obtain Compound 37 (2.29 g, yield 51%). $^1$H NMR (300 MHz, DMSO-d$_6$): ppm 8.88 (d, 1H), 8.50 (d, 1H), 8.29 (d, 2H), 7.77-7.66 (m, 4H), 7.61-7.41 (m, 10H), 7.39-7.22 (m, 9H), 7.20-7.05 (m, 4H), 6.63 (dd, 1H), 6.56 (t, 1H), 6.33 (d, 1H), HRMS (EI, m/z): calcd for C$_{54}$H$_{34}$N$_3$ 738.2783, found 738.2784.

The physical properties of Compound 37 are as follows.

TABLE 1

| Compound 37 | | |
|---|---|---|
| HOMO (eV) | LUMO (eV) | T$_1$ (eV) |
| −5.60 | −2.34 | 3.30 |

2. Synthesis of Compound 38

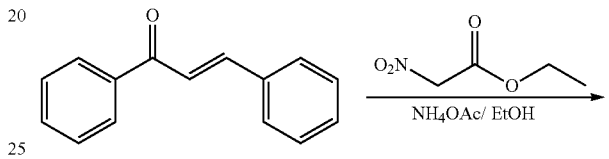

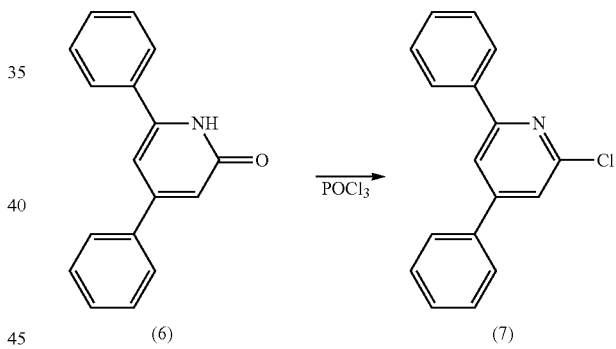

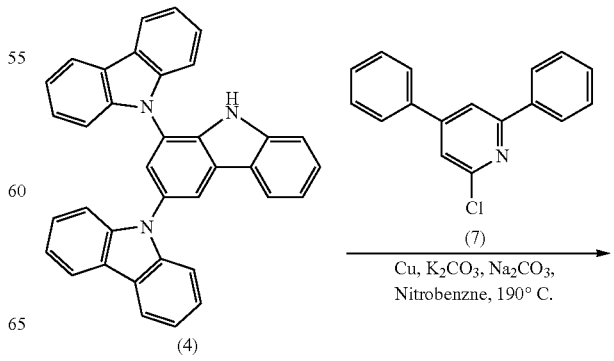

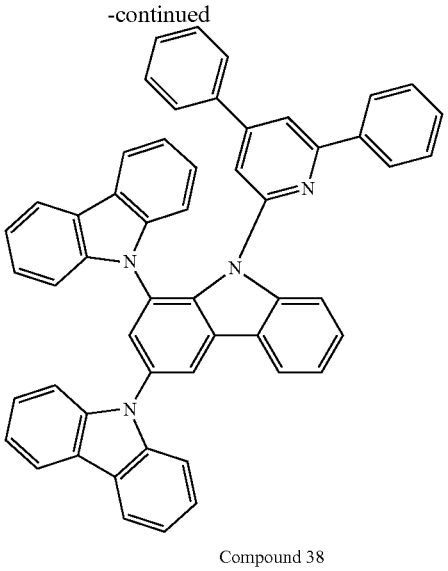

Compound 38

(1) Synthesis of Intermediate (6)

Under a nitrogen atmosphere, chalcone (15.65 g, 75.14 mmol), ethyl-2-nitroacetate (10.0 g, 75.13 mmol), NH$_4$OAc (34.75 g, 451 mmol) and EtOH (375 ml) were mixed, followed by stirring at about 100° C. for about 20 hours. After finishing the reaction, an organic layer was separated using dichloromethane (MC) (500 ml), dried with MgSO$_4$ to remove water, and separated by column chromatography (n-hexane:MC=1:2, v/v) to obtain Intermediate Compound (6) (7.04 g, yield 38%). $^1$H NMR (300 MHz, DMSO-d$_6$): ppm 11.69 (s, 1H), 7.90 (dd, 2H), 7.82 (dd, 2H), 7.50 (m, 6H), 7.00 (s, 1H), 6.66 (s, 1H).

(2) Synthesis of Intermediate Compound (7)

Under a nitrogen atmosphere, Intermediate Compound (6) (7.51 g, 30.37 mmol) and POCl$_3$ (60 ml) were mixed, followed by stirring at about 140° C. for about 12 hours. POCl$_3$ was removed via distillation, and an organic layer was separated using EA (100 ml). The organic layer was dried with MgSO$_4$ to remove water and separated by column chromatography (n-hexane:MC=10:1, v/v) to obtain Intermediate Compound (7) (3.02 g, yield 37%). $^1$H NMR (300 MHz, CDCl$_3$): ppm 7.98 (dd, 2H), 7.77 (s, 1H), 7.60 (m, 2H), 7.42 (m, 7H). HRMS (EI, m/z): calcd for C$_{17}$H$_{12}$ClN 256.0658, found 256.0658.

(3) Synthesis of Compound 38

Under a nitrogen atmosphere, Intermediate Compound (4) (2.87 g, 6.03 mmol), Intermediate Compound (7) (2.38 g, 8.96 mmol), Cu (0.037 g, 0.582 mmol), K$_2$CO$_3$ (0.80 g, 5.77 mmol), Na$_2$CO$_3$ (0.61 g, 5.77 mmol) and nitrobenzene (13 ml) were mixed, followed by stirring at about 195° C. for about 27 hours. Reaction solvents were removed via distillation, and an organic layer was separated using EA (100 ml). The organic layer was dried with MgSO$_4$ to remove water and separated by column chromatography (n-hexane:MC=10:1, v/v) to finally obtain Compound 38 (2.62 g, yield 60%). $^1$H NMR (300 MHz, DMSO-d$_6$): ppm 8.91 (s, 1H), 8.55 (d, 1H), 8.30 (d, 2H), 7.79 (s, 1H), 7.73 (d, 2H), 7.67 (m, 2H), 7.60 (t, 3H), 7.51 (m, 3H), 7.44-7.30 (m, 13H), 7.20 (d, 3H), 7.08 (s, 1H), 6.86 (s, 2H), HRMS (EI, m/z): calcd for C$_{53}$H$_{34}$N$_4$ 726.2783, found 726.2783.

The physical properties of Compound 38 are as follows.

TABLE 2

| Compound 38 | | |
| --- | --- | --- |
| HOMO (eV) | LUMO (eV) | T$_1$ (eV) |
| −5.51 | −2.20 | 3.14 |

3. Synthesis of Compound 40

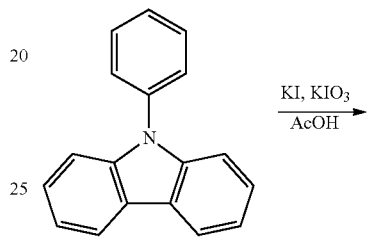

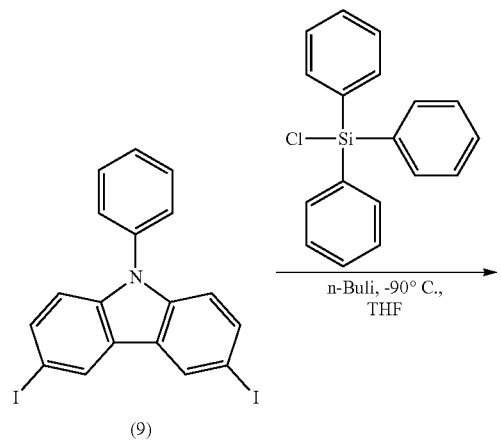

(9)

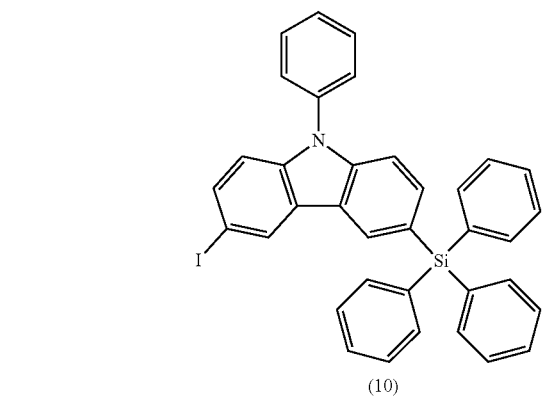

(10)

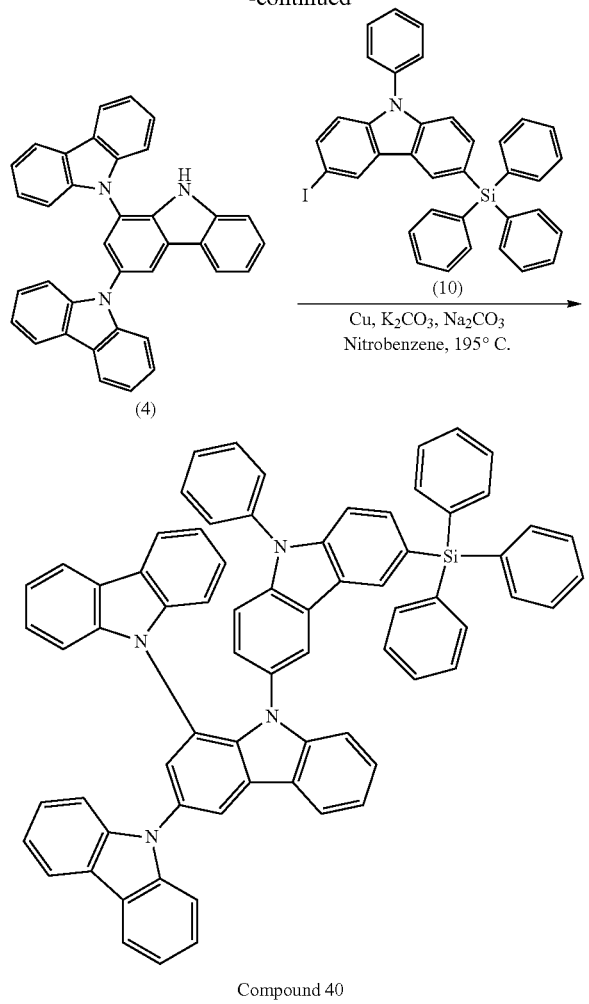

Compound 40

(1) Synthesis of Intermediate Compound (9)

Under a nitrogen atmosphere, 9-phenyl-9H-carbazole (4.0 g, 16.4 mmol), KI (3.57 g, 21.5 mmol), KIO$_3$ (4.6 g, 21.5 mmol) and AcOH (80 ml) were mixed, followed by stirring at about 80° C. for about 12 hours. After finishing the reaction, the solid thus formed was filtered with a glass filter, washed with water (200 ml), washed with 1 M NaHCO$_3$ (100 ml), and washed with 1 M Na$_2$S$_2$O$_3$ (100 ml). The solid thus formed was dissolved in EA and washed with water. An organic layer was separated, dried with MgSO$_4$ to remove water, and separated by column chromatography (n-hexane) to obtain Intermediate Compound (9) (7.62 g, yield 94%). $^1$H NMR (300 MHz, CDCl3): ppm 8.38 (s, 2H), 7.59 (m, 4H), 7.43 (m, 3H), 7.17 (d, 2H).

(2) Synthesis of Intermediate Compound (10)

Under a nitrogen atmosphere, Intermediate Compound (9) (5.0 g, 10.1 mmol) was dissolved in THF (80 ml), and the reaction temperature was decreased to about −80° C. To the reaction mixture, n-BuLi (2.5 M in hexane, 4 ml, 10.1 mmol) was slowly added dropwise, followed by stirring at the same temperature for about 1 hour. To the reaction mixture, a triphenyl silyl chloride solution (4.5 g, 15.2 mmol, THF (30 ml)) was slowly added dropwise and was stirred at about −80° C. for about 30 minutes, and then, the reaction mixture was stirred at room temperature for about 18 hours. To the reaction mixture, a 20% NH$_4$Cl solution was added to terminate the reaction. The reaction mixture was extracted with dichloromethane. An organic layer was separated, dried with MgSO$_4$ to remove water, and separated by column chromatography (n-hexane:MC=10:1, v/v) to obtain Intermediate Compound (10) (2.82 g, yield 47%). $^1$H NMR (300 MHz, CD$_2$Cl$_2$): ppm 8.41 (s, 1H), 7.8.40 (s, 1H), 7.71-7.42 (m, 24H). HRMS (EI, m/z): calcd for C36H26SiI 627.0879, found 627.0880.

(3) Synthesis of Compound 40

Under a nitrogen atmosphere, Intermediate Compound (4) (1.32 g, 2.65 mmol), Intermediate Compound (10) (2.50 g, 3.98 mmol), Cu (0.017 g, 0.265 mmol), K$_2$CO$_3$ (0.366 g, 2.65 mmol), Na$_2$CO$_3$ (0.281 g, 2.65 mmol) and nitrobenzene (10 ml) were mixed, followed by stirring at about 195° C. for about 27 hours. Reaction solvents were removed via distillation, and the reaction mixture was extracted with EtOAc (100 ml), dried with MgSO$_4$ to remove water and separated by column chromatography (n-hexane:dichloromethane=10:1, v/v) to finally obtain Compound 40 (2.14 g, yield 81%). $^1$H NMR (300 MHz, CD$_2$Cl$_2$): ppm 8.61 (s, 1H), 8.28 (d, 1H), 8.24 (d, 2H), 7.67 (s, 1H), 7.66-7.62 (m, 7H), 7.61-7.57 (m, 6H), 7.55-7.39 (m, 6H), 7.22 (m, 2H), 7.29-7.05 (m, 4H), 6.91 (t, 1H), 6.65 (dd, 1H), 6.49 (d, 1H), 6.40 (t, 1H), HRMS (FAB, m/z): calcd for C72H48N4Si, 996.3648, found 996.3676.

The physical properties of Compound 40 are as follows.

TABLE 3

| Compound 40 | | |
| --- | --- | --- |
| HOMO (eV) | LUMO (eV) | T$_1$ (eV) |
| −5.72 | −2.41 | 3.26 |

4. Synthesis of Compound 41

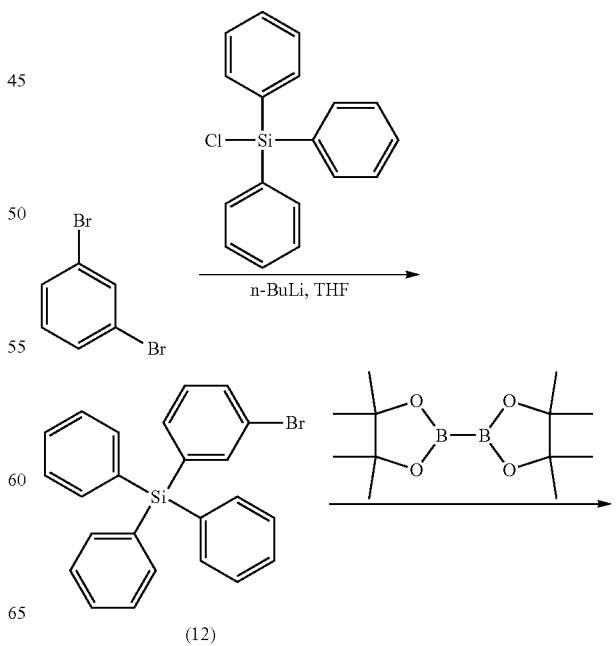

-continued
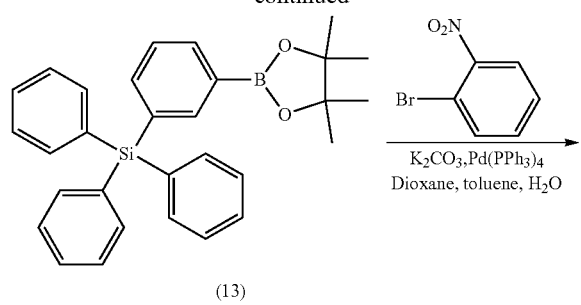
(13)
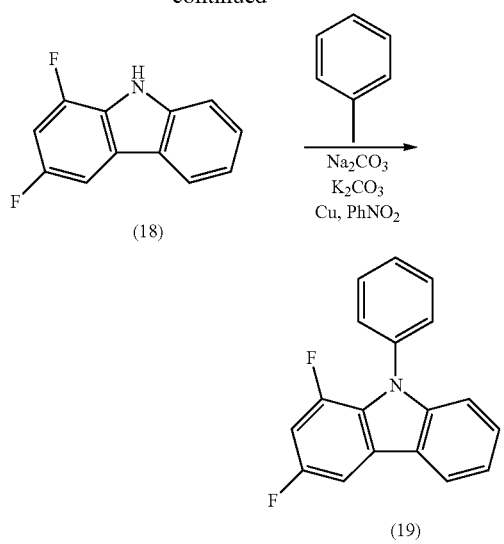
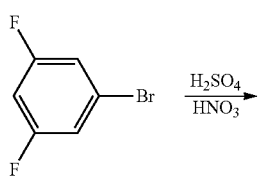
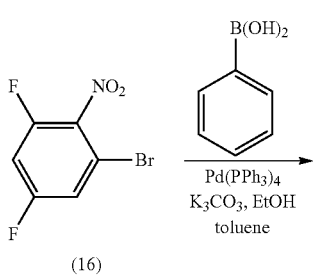
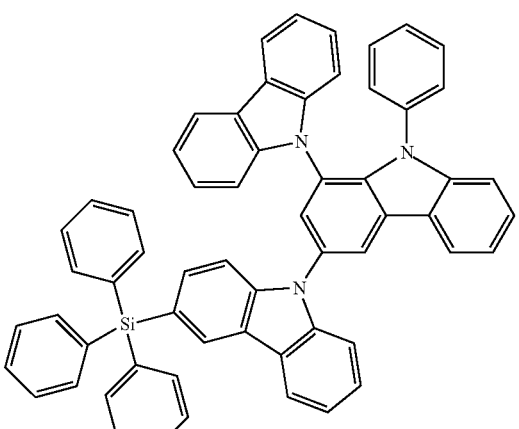
Compound 41

(1) Synthesis of Intermediate Compound (12)

Under a nitrogen atmosphere, 1,3-dibromobenzene (5.12 ml, 42.39 mmol) was dissolved in THF (200 ml), and the reaction temperature was decreased to about −78° C. To the reaction mixture, n-BuLi (2.5 M in hexane, 17 ml, 42.5 mmol) was slowly added dropwise, followed by stirring at the same temperature for about 1 hour. To the reaction mixture, a triphenyl silyl chloride solution (15 g, 50.87 mmol, THF (50 ml)) was slowly added dropwise and was stirred at about −78° C. for about 1 hour, and then, the reaction mixture was stirred at room temperature for about 12 hours. To the reaction mixture, a 20% NH₄Cl solution was added to terminate the reaction. The reaction mixture was extracted with EA. An organic layer was separated, dried with MgSO₄ to remove water, and separated by column chromatography (n-hexane) to obtain Intermediate Compound (12) (10.57 g, yield 60%). $^1$H NMR (300 MHz, CDCl₃): ppm 7.62 (t, 1H), 7.57-7.51 (m, 7H), 7.45-7.40 (m, 4H), 7.38-7.35 (m, 6H), 7.21 (d, 1H).

(2) Synthesis of Intermediate Compound (13)

Under a nitrogen atmosphere, Intermediate Compound (12) (6.85 g, 16.5 mmol), bis(pinacolato)diboron (6.28 g, 16.5 mmol), potassium acetate (3.56 g, 36.27 mmol) and 1,4-dioxane (40 ml) were mixed, followed by stirring at about 60° C. for about 15 minutes. To the reaction mixture, Pd(dppf)CH₂Cl₂ (0.18 g, 0.25 mmol) was added, followed by stirring at about 80° C. for about 14 hours. The reaction mixture was cooled to room temperature, extracted with toluene, dried with MgSO₄ to remove water, and separated by column chromatography (n-hexane:EA=5:1, v/v) to obtain Intermediate Compound (13) (6.34 g, yield: 81%). $^1$H NMR (300 MHz, CD₂Cl₂): δ ppm 8.00 (s, 1H), 7.89 (d, 2H), 7.68 (d, 1H), 7.64-7.58 (m, 6H), 7.49-7.40 (m, 10H), 1.34 (s, 12H).

(3) Synthesis of Intermediate Compound (14)

Under a nitrogen atmosphere, 1-bromo-2-nitrobenzene (2.18 g, 10.8 mmol), Intermediate Compound (13) (6.0 g, 13 mmol), K₂CO₃ (4.5 g, 32.6 mmol), dioxane (30 ml), toluene (30 ml) and distilled water (10 ml) were mixed, followed by stirring for about 20 minutes. Then, Pd(PPh₃)₄ (0.47 g, 0.41 mmol) was added thereto, followed by stirring at about 90° C. for about 12 hours. The reaction mixture was cooled to room temperature, extracted with EA, dried with MgSO₄ to remove water, and separated by column chromatography (n-hexane:MC=10:1, v/v) to obtain Intermediate Compound (14) (6.34 g, yield: 81%). $^1$H NMR (300 MHz, DMSO-d₆): δ ppm 7.86 (d, 1H), 7.84-7.59 (m, 8H), 7.55-7.40 (m, 14H).

(4) Synthesis of Intermediate Compound (15)

Under a nitrogen atmosphere, Intermediate Compound (14) (2.6 g, 5.68 mmol), P(OEt)₃ (30 ml), and dichlorobenzene (15 ml) were mixed, followed by stirring at about 150° C. for about 20 hours. Reaction solvents were removed via distillation. The reaction mixture was extracted with EA, dried with MgSO₄ to remove water, and separated by column chromatography (n-hexane:EA=6:1, v/v) to obtain Intermediate Compound (15) (1.52 g, yield 62%). $^1$H NMR (300 MHz, DMSO-d₆): δ ppm 8.33 (s, 1H), 8.01 (d, 1H), 7.66 (m, 7H), 7.55-7.44 (m, 13H), 7.23 (m, 1H).

(5) Synthesis of Intermediate Compound (16)

1-bromo-3,5-difluorobenzene (10 g, 52.1 mmol) was added to c-H₂SO₄ (10 ml), followed by stirring for about 20 minutes. Then, fuming HNO₃ (2.5 ml) was added dropwise for about 30 minutes. The reaction mixture was stirred for about 2 hours, and the reaction mixture was slowly poured into ice water (500 ml), followed by stirring for about 30 minutes. The solid thus formed was filtered using a glass filter and sufficiently washed with distilled water. The solid thus obtained was dissolved in EA for extraction, dried with MgSO₄ to remove water, and separated by column chromatography (n-hexane:EA=6:1 v/v) to obtain Intermediate Compound (16) (9.25 g, yield 75%). $^1$H NMR (300 MHz, DMSO-d₆): δ ppm 7.90 (ddd, 1H), 7.86 (ddd, 1H).

(6) Synthesis of Intermediate Compound (17)

Under a nitrogen atmosphere, Intermediate Compound (16) (19.5 g, 82 mmol), phenyl boronic acid (11 g, 90.2 mmol), K₂CO₃ (22.2 g, 161 mmol), EtOH (160 ml) and toluene (200 ml) were mixed and stirred for about 20 minutes. Then, Pd(PPh₃)₄ (1.0 g, 0.64 mmol) was added thereto, followed by stirring at about 90° C. for about 10 hours. The reaction mixture was extracted with EA, dried with MgSO₄ to remove water, and separated by column chromatography (n-hexane:EA=6:1, v/v) to obtain Intermediate Compound (17) (15 g, yield: 78%). $^1$H NMR (300 MHz, CD₂Cl₂): δ ppm 7.52-7.42 (m, 3H), 7.13-7.04 (m, 2H), 7.13-7.04 (m, 2H).

(7) Synthesis of Intermediate Compound (18)

Under a nitrogen atmosphere, Intermediate Compound (17) (15 g, 64 mmol), PPh₃ (33.59 g, 128 mmol) and o-dichlorobenzene (130 ml) were mixed, followed by stirring at about 185° C. for about 15 hours. After finishing the reaction, the reaction mixture was cooled to room temperature and filtered using celite. The reaction solvents were removed via distillation under a reduced pressure, and the reaction product was extracted with EA, dried with MgSO₄ to remove water, and separated by column chromatography (n-hexane:EA=10:1, v/v) to obtain Intermediate Compound (18) (7.15 g, yield 55%). $^1$H NMR (300 MHz, CDCl₃): δ ppm 8.15 (s, 1H), 8.13 (d, 1H), 7.44-7.35 (m, 2H), 7.30-7.25 (m, 1H), 6.91 (dd, 1H), 6.72 (m, 1H).

(8) Synthesis of Intermediate Compound (19)

Under a nitrogen atmosphere, Intermediate Compound (18) (7.0 g, 34.4 mmol), iodobenzene (7.0 g, 34.4 mmol), Cu (0.22 g, 3.44 mmol), K₂CO₃ (4.75 g, 34.4 mmol), Na₂CO₃ (3.65 g, 34.4 mmol) and nitrobenzene (50 ml) were mixed, followed by stirring at about 195° C. for about 12 hours. Reaction solvents were removed via distillation, and an organic layer was separated using EtOAc (100 ml), dried with MgSO₄ to remove water and separated by column chromatography (n-hexane) to obtain Intermediate Compound (19) (7.9 g, yield 82%). $^1$H NMR (300 MHz, CD₂Cl₂): ppm 7.72-7.65 (m, 4H), 7.63-7.58 (m, 2H), 7.55-7.49 (m, 5H), MS (EI, m/z): 278.

(9) Synthesis of Intermediate Compound (20)

Intermediate Compound (19) (0.99 g, 3.52 mmol) was dissolved in anhydrous DMF (10 ml), and NaH (0.084 g, 3.52 mmol) was added thereto, followed by stirring for about 30 minutes. Then, a solution of Compound (15) (1.51 g, 3.54 mmol) dissolved in anhydrous DMF (10 ml) was slowly added dropwise to the reaction mixture, followed by stirring at about 100° C. for about 12 hours. The reaction mixture was cooled to room temperature, extracted with MC, dried with MgSO₄ to remove water, and separated by column chromatography (n-hexane:MC=10:1, v/v) to obtain Intermediate Compound (20) (1.86 g, yield 77%). $^1$H NMR (300 MHz, CD₂Cl₂): ppm 8.64 (s, 1H), 7.72-7.60 (m, 15H), 7.55-7.48 (m, 15H), 7.20 (m, 2H).

(10) Synthesis of Compound 41

Intermediate Compound (20) (1.8 g, 2.63 mmol) was dissolved in anhydrous DMF (20 ml). Then, NaH (0.063 g, 2.63 mmol) was added thereto, followed by stirring for about 30 minutes. A solution of carbazole (0.45 g, 2.70 mmol) dissolved in anhydrous DMF (10 ml) was slowly added dropwise to the reaction mixture, followed by stirring at about 120° C. for about 15 hours. The reaction mixture was cooled to room temperature, extracted with EA, dried with MgSO₄ to remove water, and separated by column chromatography (n-hexane:MC=10:1, v/v) to finally obtain Compound 41 (1.99 g, yield 90%). ¹H NMR (300 MHz, CD₂Cl₂): ppm 8.55 (s, 1H), 8.47 (s, 1H), 8.30-8.17 (m, 12H), 7.87 (s, 1H), 7.71 (s, 1H), 7.60-7.57 (m, 5H), 7.53-7.44 (m, 20H), HRMS (FAB, m/z): calcd for C60H41N3Si, 831.3070, found 831.3049.

The physical properties of Compound 41 are as follows.

TABLE 4

| Compound 41 | | |
|---|---|---|
| HOMO (eV) | LUMO (eV) | T₁ (eV) |
| −5.56 | −2.18 | 3.31 |

5. Synthesis of Compound 21

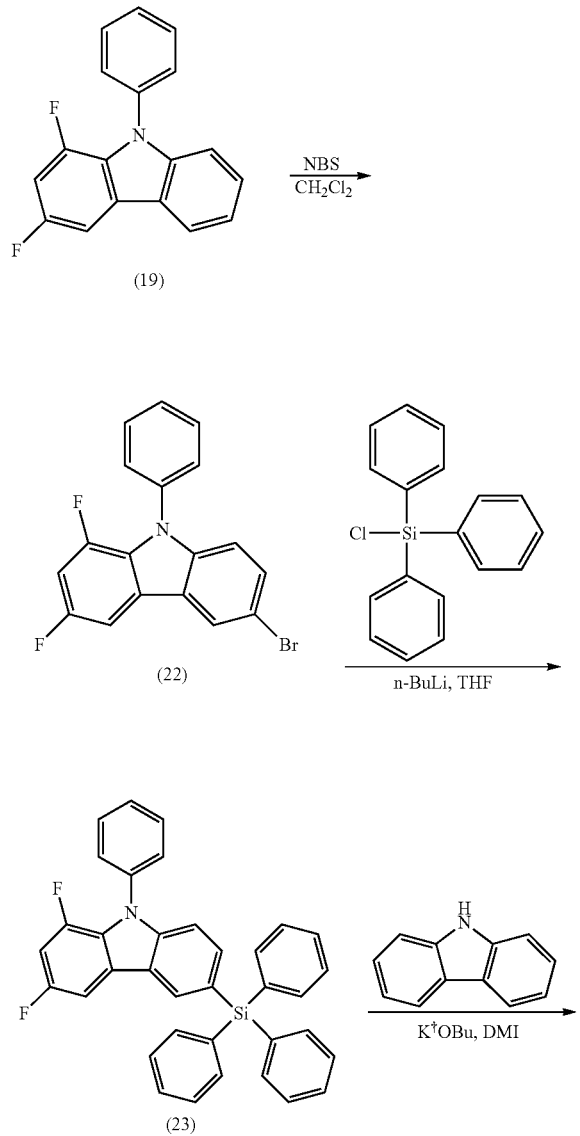

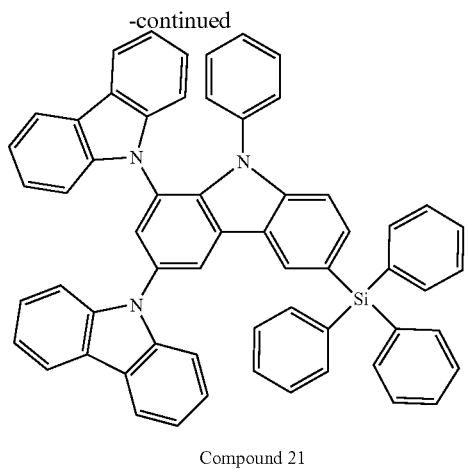

Compound 21

(1) Synthesis of Intermediate Compound (22)

Intermediate Compound (19) (5 g, 17.9 mmol) was dissolved in CH₂Cl₂ (50 ml), and NBS (3.2 g, 18 mmol) was slowly added to the reaction mixture. Then, light was blocked at room temperature, stirring was performed for about 12 hours. Distilled water (100 ml) was added to terminate the reaction, and the reaction product was extracted with MC, dried with MgSO₄ to remove water, and separated by column chromatography (n-hexane) to obtain Intermediate Compound (22) (5.0 g, yield 85%). ¹H NMR (300 MHz, CD₂Cl₂): ppm 8.00 (s, 1H), 7.88 (dt, 1H), 7.66 (dt, 1H), 761-7.58 (m, 7H).

(2) Synthesis of Intermediate Compound (23)

Under a nitrogen atmosphere, Intermediate Compound (22) (3.5 g, 9.77 mmol) was dissolved in THF (50 ml), and the reaction temperature was decreased to about −78° C. To the reaction mixture, n-BuLi (2.5 M in hexane, 4.3 ml, 10.7 mmol) was slowly added dropwise, followed by stirring at the same temperature for about 1 hour. To the reaction mixture, a triphenyl silyl chloride solution (2.89 g, 9.80 mmol, THF (20 ml)) was slowly added dropwise and was stirred at about −78° C. for about 30 minutes, and then, the reaction mixture was stirred at room temperature for about 12 hours. To the reaction mixture, a 20% NH₄Cl solution was added to terminate the reaction. The reaction mixture was extracted with MC. An organic layer was separated, dried with MgSO₄ to remove water, and separated by column chromatography (n-hexane:dichloromethane=15:1, v/v) to obtain Intermediate Compound (23) (3.52 g, yield 67%). ¹H NMR (300 MHz, DMSO-d₆): ppm 8.61 (s, 1H), 8.49 (s, 1H), 7.73-7.62 (m, 6H), 7.51-7.42 (m, 14H), 7.36-7.32 (m, 2H), 7.22 (d, 1H).

(3) Synthesis of Compound 21

Under a nitrogen atmosphere, carbazole (0.96 g, 5.72 mmol), KO^tBu (0.65 g, 5.83 mmol), and 1,3-dimethyl-2-imidazolidinone (DMI, 10 ml) were mixed. The reaction temperature was increased to about 120° C., and a solution of Intermediate (23) (1.5 g, 2.79 mmol) dissolved in DMI (7 ml) was slowly added to the reaction mixture dropwise, and the reaction mixture was stirred at about 180° C. for about 10 hours. After cooling the reaction mixture to room temperature, ice water (50 ml) was added, followed by stirring for about 30 minutes. The solid thus formed was filtered using a glass filter and washed with distilled water many times. The solid thus formed was dissolved in EA for extraction, dried with MgSO₄ to remove water, and separated by column chromatography (n-hexane:MC=10:1, v/v)

to finally obtain Compound 21 (1.51 g, 65%). ¹H NMR (300 MHz, CD₂Cl₂): ppm 8.56 (s, 1H), 8.25-8.20 (m, 3H), 8.02 (d, 1H), 7.77 (dd, 1H), 7.72 (d, 1H), 7.58 (d, 2H), 7.53-7.26 (m, 24H), 7.18 (dd, 1H), 7.10-6.98 (m, 4H), 6.88-6.78 (m, 2H), 6.49 (t, 1H).

Physical properties of Compound 21 are as follows.

TABLE 5

| Compound 21 | | |
|---|---|---|
| HOMO (eV) | LUMO (eV) | T₁ (eV) |
| −5.50 | −2.17 | 3.32 |

6. Synthesis of Compound 28

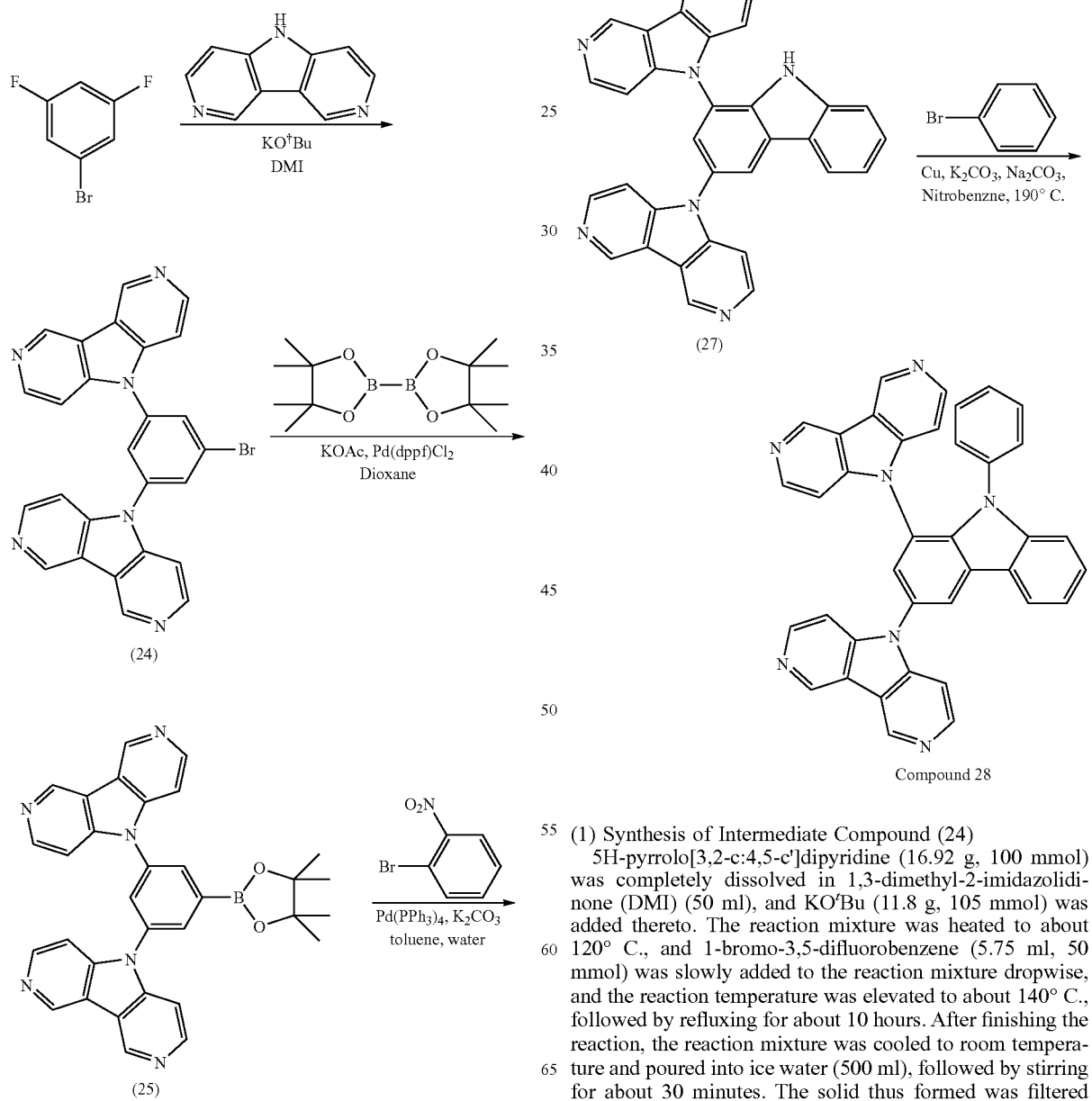

(1) Synthesis of Intermediate Compound (24)

5H-pyrrolo[3,2-c:4,5-c']dipyridine (16.92 g, 100 mmol) was completely dissolved in 1,3-dimethyl-2-imidazolidinone (DMI) (50 ml), and KO^tBu (11.8 g, 105 mmol) was added thereto. The reaction mixture was heated to about 120° C., and 1-bromo-3,5-difluorobenzene (5.75 ml, 50 mmol) was slowly added to the reaction mixture dropwise, and the reaction temperature was elevated to about 140° C., followed by refluxing for about 10 hours. After finishing the reaction, the reaction mixture was cooled to room temperature and poured into ice water (500 ml), followed by stirring for about 30 minutes. The solid thus formed was filtered using a glass filter and washed with distilled water many times and then with EtOH (500 ml), and the solid thus obtained was dried in vacuum to obtain Intermediate Compound (24) (39.3 g, 80%). $^1$H NMR (300 MHz, CDCl$_3$): δ ppm 9.32 (d, 4H), 8.35 (d, 4H), 7.53 (d, 4H), 7.50 (s, 3H).

(2) Synthesis of Intermediate Compound (25)

Intermediate Compound (24) (30.0 g, 61.1 mmol), bis(pinacolato)diboron (18.62 g, 73.3 mmol), and potassium acetate (23.99 g, 244.4 mmol) were dissolved in 1,4-dioxane (200 ml), followed by stirring under a nitrogen atmosphere at about 60° C. for about 15 minutes. To the reaction mixture, Pd(dppf)CH$_2$Cl$_2$ (0.82 g, 1.0 mmol) was added, followed by stirring at about 80° C. for about 14 hours. The reaction mixture was cooled to room temperature, extracted with toluene, dried with MgSO$_4$ to remove water, and separated by column chromatography (n-hexane:dichloromethane (MC)=1:3, v/v) to obtain Intermediate Compound (25) (19.74 g, yield: 60%). $^1$H NMR (300 MHz, CDCl$_3$): δ ppm 9.32 (d, 4H), 8.35 (d, 4H), 7.57-7.53 (m, 5H), 7.41 (s, 2H), 1.21 (s, 12H).

(3) Synthesis of Intermediate Compound (26)

Intermediate Compound (25) (15.0 g, 27.9 mmol) and 1-bromo-2-nitrobenzene (5.64 g, 27.9 mmol) were dissolved in dioxane/toluene (30 ml/30 ml), and to the reaction mixture, K$_2$CO$_3$ (7.7 g, 55.8 mmol) and distilled water (10 ml) were added, followed by stirring in a nitrogen atmosphere for about 20 minutes. Then, Pd(PPh$_3$)$_4$(O) (0.8 g, 0.69 mmol) was added thereto, and the reaction mixture was stirred at about 80° C. for about 12 hours. After finishing the reaction, the reaction temperature was decreased to room temperature, and the reaction product was extracted with ethyl acetate (EA) (100 ml), dried with MgSO$_4$ to remove water, and separated by column chromatography (n-hexane:EA=10:1, v/v) to obtain Intermediate Compound (26) (10.42 g, yield 70%). $^1$H NMR (300 MHz, CDCl$_3$): δ ppm 9.34 (d, 4H), 8.35 (d, 4H), 8.17 (s, 2H), 8.03-8.01 (m, 2H), 7.87-7.80 (m, 2H), 7.61 (s, 1H), 7.51 (d, 4H).

(4) Synthesis of Intermediate Compound (27)

Under a nitrogen atmosphere, Intermediate Compound (26) (10.0 g, 18.7 mmol), PPh$_3$ (7.92 g, 30.2 mmol) and o-dichlorobenzene (80 ml) were mixed, followed by stirring at about 185° C. for about 12 hours. Then, reaction solvents were removed via distillation, and the reaction product was extracted with EA (100 ml), dried with MgSO$_4$ to remove water, separated by column chromatography (n-hexane:EA=10:1, v/v), washed with MeOH, and dried in vacuum to obtain Intermediate Compound (27) (6.11 g, yield 65%). $^1$H NMR (300 MHz, DMSO-d$_6$): ppm 11.33 (s, 1H), 9.34 (d, 4H), 8.35 (d, 4H), 8.17 (m, 1H), 7.63 (m, 2H), 7.55-7.50 (m, 5H), 7.32 (s, 1H), 7.18 (m, 1H).

(5) Synthesis of Compound 28

Under a nitrogen atmosphere, Intermediate Compound (27) (5.0 g, 9.97 mmol), bromobenzene (1.72 g, 10.98 mmol), Cu (0.038 g, 0.603 mmol), K$_2$CO$_3$ (1.38 g, 9.97 mmol), Na$_2$CO$_3$ (1.06 g, 9.97 mmol) and nitrobenzene (20 ml) were mixed, followed by stirring at about 195° C. for about 18 hours. Then, reaction solvents were removed via distillation, and an organic layer was separated using EA (100 ml), dried with MgSO$_4$ to remove water, and separated by column chromatography (n-hexane:dichloromethane=10:1, v/v) to finally obtain Compound 28 (3.46 g, yield 60%). $^1$H NMR (300 MHz, DMSO-d$_6$): ppm 9.34 (d, 4H), 8.55 (d, 1H), 8.35 (d, 4H), 7.94 (d, 1H), 7.63-7.51 (m, 10H), 7.32 (m, 2H), 7.16 (m, 1H).

(Device Manufacturing Examples)

A bottom emission type organic electroluminescence device of Example 1 was manufactured using Compound 37 as a host material in an emission layer.

[Compound of Example 1]

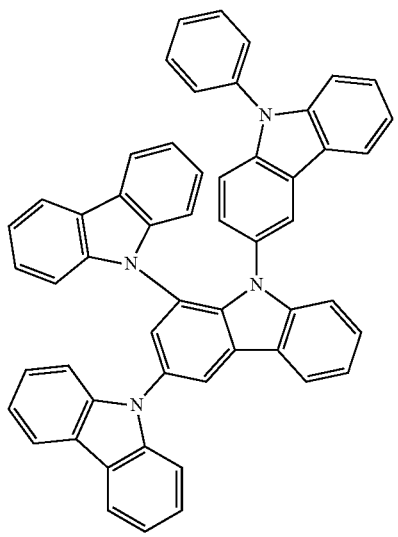

37

A top emission type organic electroluminescence device of Example 2 was manufactured using Compound 37 as a host material in an HT type emission layer and Compound 28 as a host in an ET type emission layer.

[Compound of Example 2]

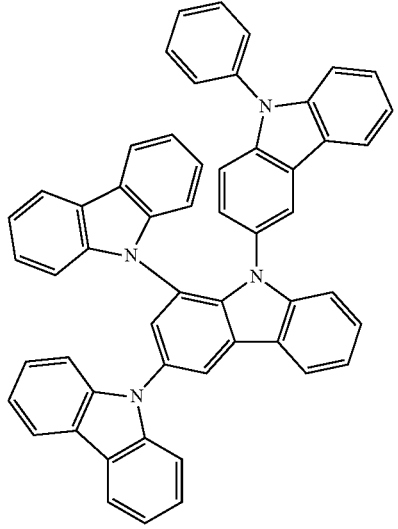

37

-continued

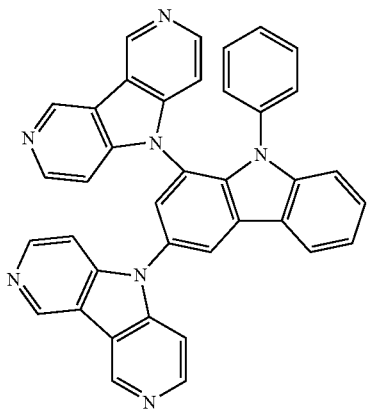

28

A bottom emission type organic electroluminescence device of Comparative Example 1 was manufactured using Comparative Compound X-1 below as a host material in an emission layer.

Compound of Comparative Example 1

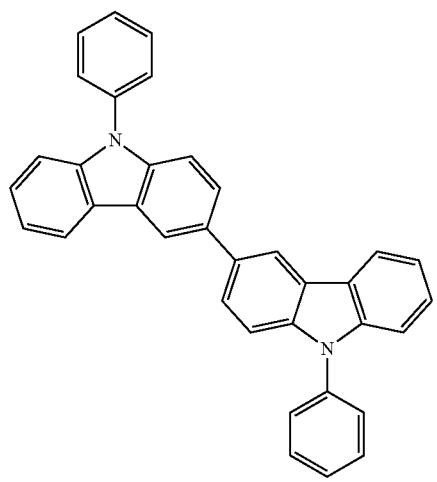

[X-1]

The bottom emission type organic electroluminescence devices of Example 1 and Comparative Example 1 were manufactured as follows.

An ITO glass substrate (product of Corning Co.) on which an ITO layer with a thickness of 15 Ω/cm² (1,200 Å) was formed, was cut to a size of 50 mm×50 mm×0.7 mm, and was washed using isopropyl alcohol and pure water for about 5 minutes, respectively, by ultrasonic wave. Then, the ITO glass substrate was exposed to ultraviolet rays for about 30 minutes, exposed to ozone for washing and installed in a vacuum deposition apparatus. On the ITO glass substrate, NPB was vacuum deposited to form a hole injection layer to a thickness of about 300 Å, and on the hole injection layer, mCP was vacuum deposited to form a hole transport layer to a thickness of about 200 Å. On the hole transport layer, the Example Compound or Comparative Compound host and a dopant of a carbene-based Ir complex were co-deposited in a weight ratio of 90:10 to form an emission layer to a thickness of about 250 Å. On the emission layer, TAZ was deposited to form an electron transport layer to a thickness of about 200 Å, and on the electron transport layer, LiF was deposited to form an electron injection layer to a thickness of about 10 Å. On the electron injection layer, Al was deposited to form a second electrode with a LiF/Al structure to a thickness of about 100 Å.

The top emission type organic electroluminescence device was manufactured by conducting the same method as Example 1 and Comparative Example 1, except for forming a first electrode of an LiF/Al structure, forming a second electrode using ITO, and using a mixed host of Example Compounds 37 and 28 in an emission layer.

TABLE 6

|  | HOMO (eV)[a] | LUMO (eV) | Op.V | Cd/A[b] |
| --- | --- | --- | --- | --- |
| Example 1 | −5.60 | −2.34 | 4.0 | 14.5 |
| Comparative Example 1 | −5.40 | −1.75 | 4.6 | 5.9 |
| Example 2 | −5.60 | −2.34 | 3.7 | 15.0[c] |
|  | −6.07 | −2.41 |  |  |

[a]CV measured value,
[b]bottom emission type TEG required luminance standard, and
[c]top emission type TEG required luminance standard (CIEy = 0.061)

Referring to the results of Table 6, the organic electroluminescence device including the heterocyclic compound according to an embodiment of the present disclosure is found to be advantageous in attaining a low driving voltage and high efficiency.

Experimental Example

Figure 5:
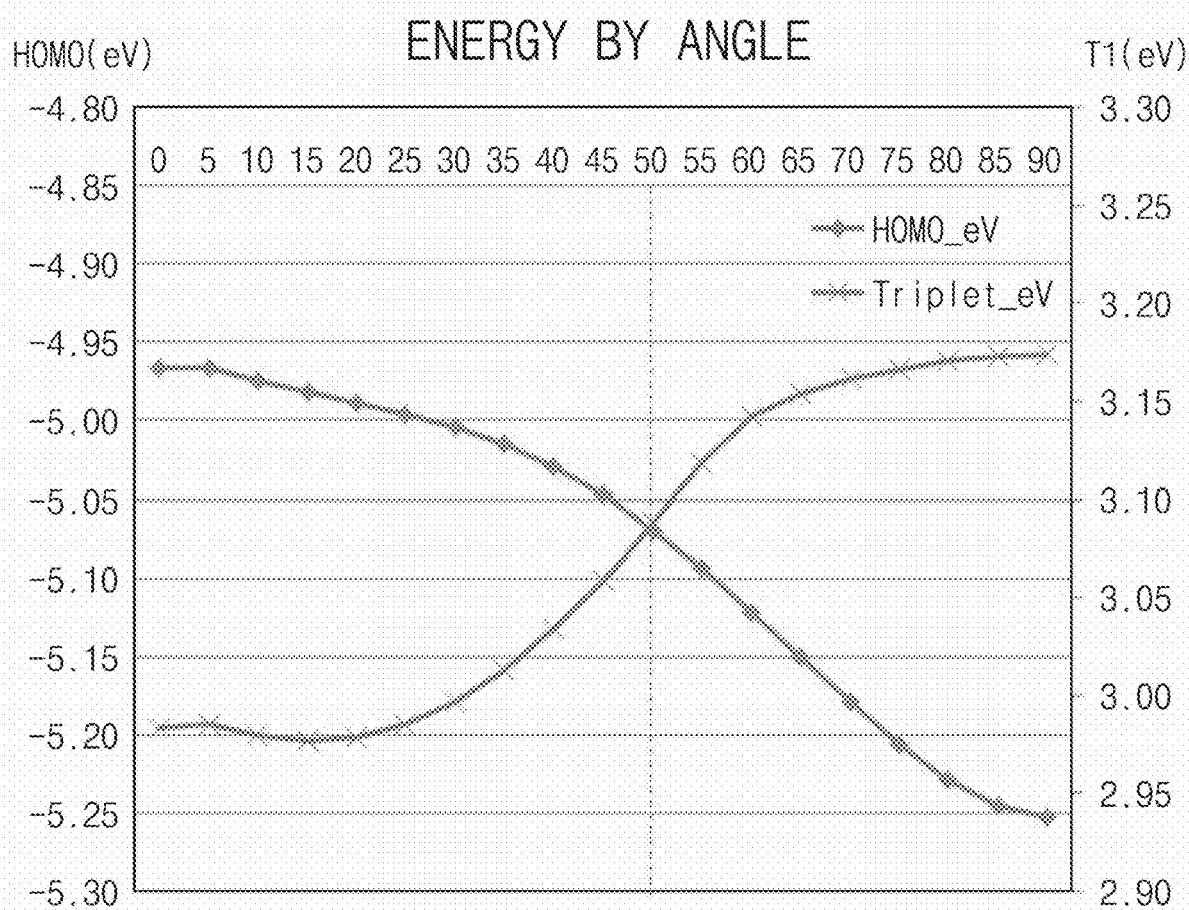
FIG. 5 is a graph on the changes of a HOMO energy level and a triplet energy level in accordance with a torsional angle in Compound 1.

FIG. 5 is a graph on the changes of a HOMO energy level and a triplet energy level in accordance with a torsional angle in Compound 1. Referring to FIG. 5, if X in Formula 1 is a direct linkage and if the torsional angle of a single bond connecting Formula 1 with Formula 2 or Formula 3 is about 50 degrees or more, it is found that a relatively high triplet energy level may be attained.

[Compound 1]

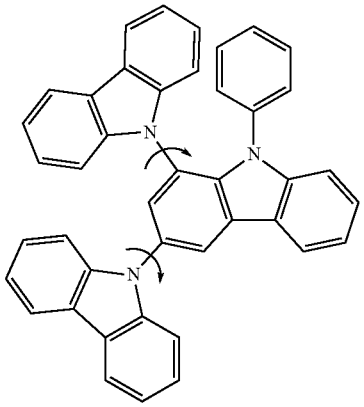

1

The organic electroluminescence device including the compound according to an embodiment of the present disclosure has excellent efficiency and life characteristics.

The organic electroluminescence device including the compound according to an embodiment of the present disclosure is advantageous in decreasing a driving voltage.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A heterocyclic compound represented by the following Formula 1:

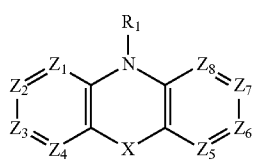

[Formula 1]

wherein in Formula 1,

X is a direct linkage, or $CR_2R_3$, $Z_1$ to $Z_8$ are each independently $CR_4$ or N, each of $R_1$ to $R_4$ is independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring, at least two of $Z_1$, $Z_3$, $Z_6$ and $Z_8$ are independently $CR_5$, and $R_5$ is represented by the following Formula 2 or Formula 3:

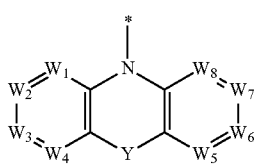

[Formula 2]

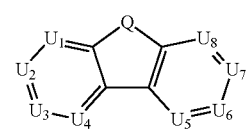

[Formula 3]

wherein in Formula 2,

Y is a direct linkage, $CR_6R_7$, $SiR_8R_9$, $NR_{10}$, O, S or $SO_2$, $W_1$ to $W_8$ are each independently $CR_{11}$ or N, and each of $R_6$ to $R_{11}$ is independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring, except that if $Z_1$ and $Z_3$ in Formula 1 are each independently $CR_5$ wherein $R_5$ is represented by Formula 2 or $Z_6$ and $Z_8$ in Formula 1 are each independently $CR_5$ wherein $R_5$ is represented by Formula 2 or $Z_3$ and $Z_6$ in Formula 1 are each independently $CR_5$ wherein $R_5$ is represented by Formula 2, and if X in Formula 1 is a direct linkage, and if $W_1$ to $W_8$ in Formula 2 are each $CR_{11}$, then Y in Formula 2 is not a direct linkage, and wherein in Formula 3, Q is $NR_{12}$, O, or S, $U_1$ to $U_8$ are each independently $CR_{13}$ or N, one of $U_1$ to $U_8$ is a connecting part, and each of $R_{12}$ and $R_{13}$ is independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring, except that if $Z_3$ and $Z_6$ in Formula 1 are each independently $CR_5$ wherein $R_5$ is represented by Formula 3, and if X in Formula 1 is either a direct linkage or $CR_2R_3$ wherein $R_2$ and $R_3$ are each an alkyl group, then Q in Formula 3 is not $NR_{12}$.

2. The heterocyclic compound of claim 1, wherein $Z_1$ and $Z_3$ are each independently represented by $CR_5$.

3. The heterocyclic compound of claim 2, wherein $Z_6$ and $Z_8$ are each independently $CR_4$ wherein $R_4$ is hydrogen, or represented by $CR_5$ or one of the following structures:

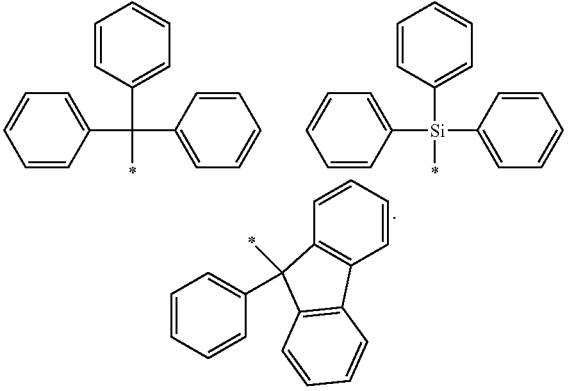

4. The heterocyclic compound of claim 1, wherein $R_1$ is a substituted or unsubstituted phenyl group, a substituted or unsubstituted pyridine group, or a substituted or unsubstituted carbazole group.

5. The heterocyclic compound of claim 1, wherein $R_1$ is represented by one of the following structures:

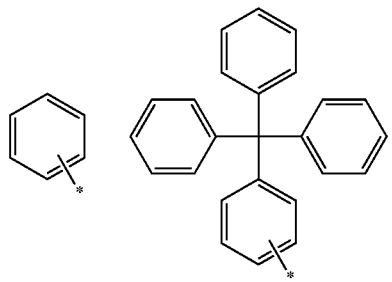

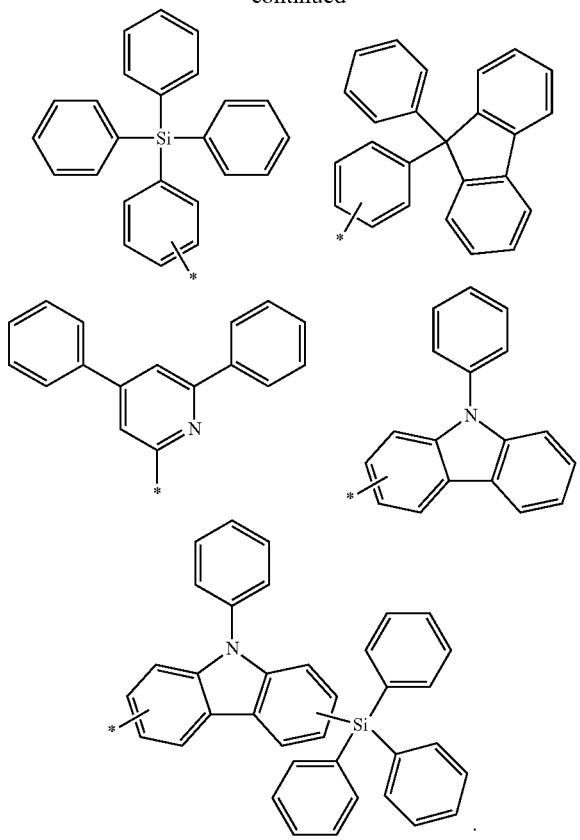

6. The heterocyclic compound of claim 1, wherein
either $Z_1$ and $Z_8$, or $Z_3$ and $Z_6$, are $CR_5$, where $R_5$ is represented by Formula 3, and
if $Z_1$ and $Z_8$ are $CR_5$, at least one of $Z_3$ and $Z_6$ is N, and
if $Z_3$ and $Z_6$ are $CR_5$, at least one of $Z_1$ and $Z_8$ is N.

7. The heterocyclic compound of claim 6, wherein in Formula 3, Q is O, and at least one of $U_2$ and $U_7$ is N.

8. The heterocyclic compound of claim 1, wherein in Formula 2, Y is a direct linkage, and
at least one of $W_1$, $W_3$, $W_6$ or $W_8$ is N.

9. The heterocyclic compound of claim 1, wherein in Formula 2, Y is a direct linkage, and $W_1$ and $W_3$, or $W_6$ and $W_8$ are N.

10. The heterocyclic compound of claim 1, wherein Formula 1 is represented by the following Formula 5:

[Formula 5]

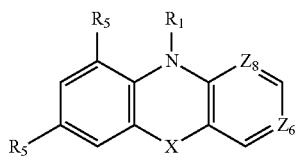

wherein in Formula 5,
each $R_5$ is independently represented by Formula 2 or Formula 3,
$R_1$ is a substituted or unsubstituted phenyl group, a substituted or unsubstituted pyridine group, or a substituted or unsubstituted carbazole group, and
X, $Z_6$ and $Z_8$ are the same as defined in Formula 1,
except that
if each $R_5$ in Formula 5 is represented by Formula 2 or $Z_6$ and $Z_8$ in Formula 5 are each independently $CR_5$ wherein $R_5$ is represented by Formula 2 or $Z_6$ in Formula 5 is $CR_5$ wherein $R_5$ is represented by Formula 2 and the $R_5$ in Formula 5 that is bonded at a para-position to the N in Formula 5 is represented by Formula 2, and
if X in Formula 5 is a direct linkage, and
if $W_1$ to $W_8$ in Formula 2 are each $CR_{11}$,
then Y in Formula 2 is not a direct linkage, and
except that
if $Z_6$ in Formula 5 is $CR_5$ wherein $R_5$ is represented by Formula 3 and the $R_5$ in Formula 5 that is bonded at a para-position to the N in Formula 5 is represented by Formula 3, and
if X in Formula 1 is either a direct linkage or $CR_2R_3$ wherein $R_2$ and $R_3$ are each an alkyl group,
then Q in Formula 3 is not $NR_{12}$.

11. The heterocyclic compound of claim 1, wherein X is a direct linkage, and
a torsional angle of a single bond connecting Formula 1 with Formula 2 or Formula 3 is about 50 degrees or more.

12. The heterocyclic compound of claim 1, wherein X is $CR_2R_3$, and
a torsional angle of a single bond connecting Formula 1 with Formula 2 or Formula 3 is about 70 degrees or more.

13. The heterocyclic compound of claim 1, wherein the heterocyclic compound represented by Formula 1 is one selected from compounds represented in the following Compound Group 1:

[Compound Group 1]

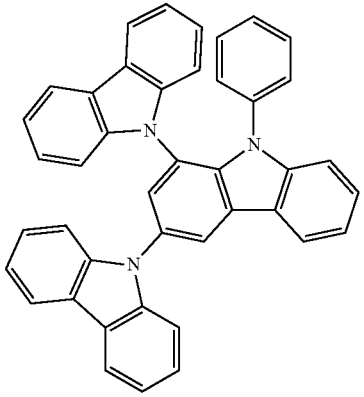

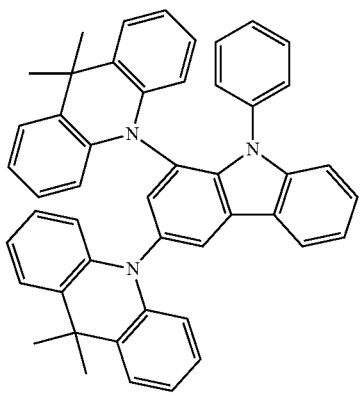

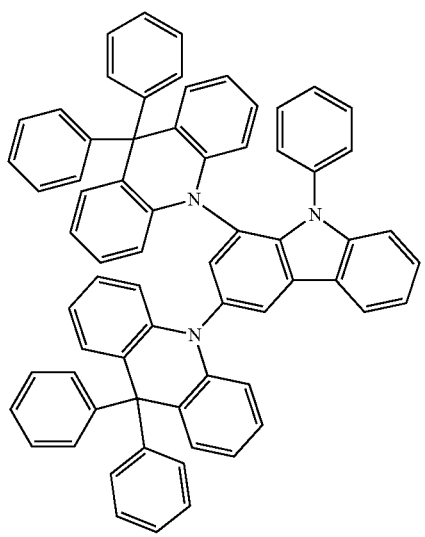
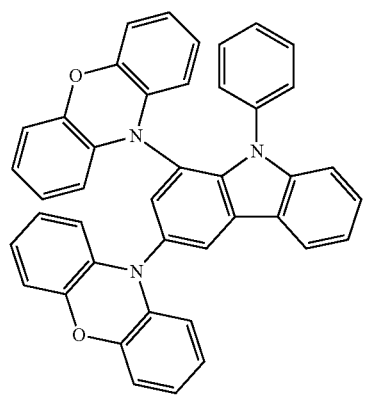
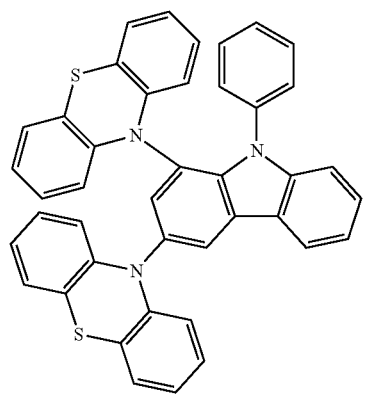
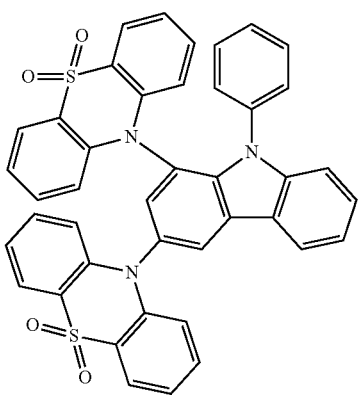
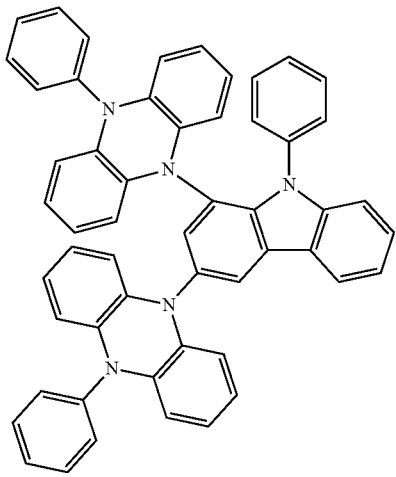
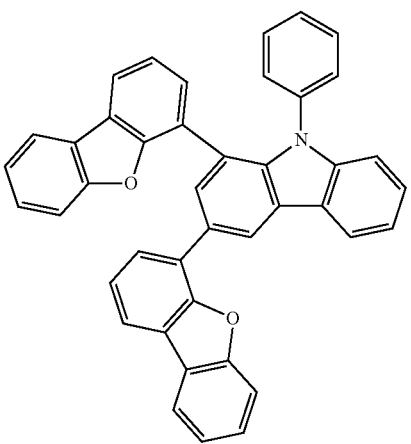

9
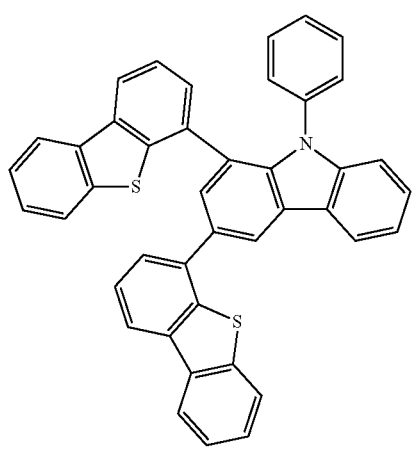
10
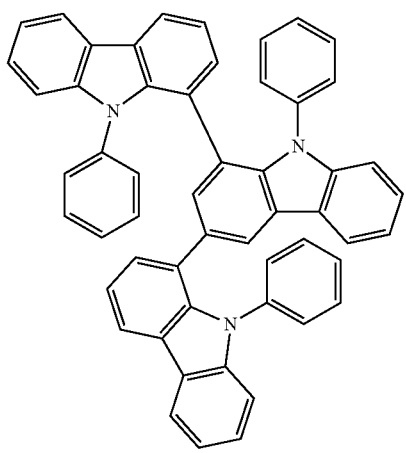
11
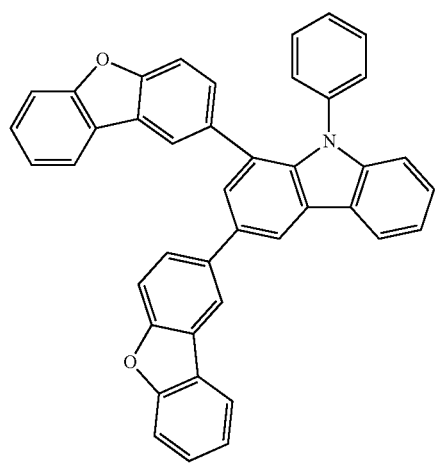
12
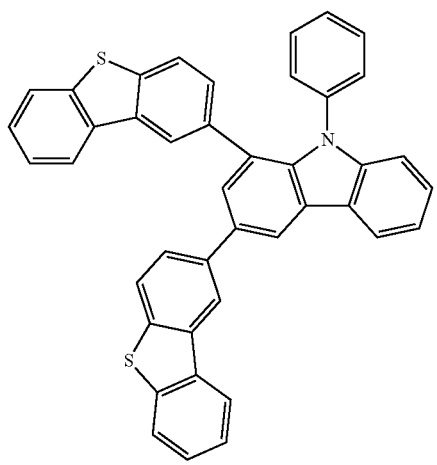
13
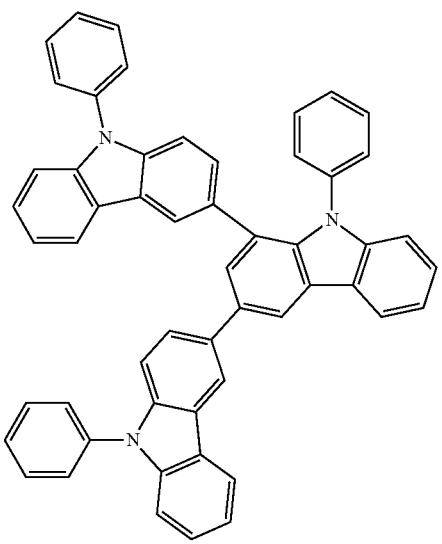
14
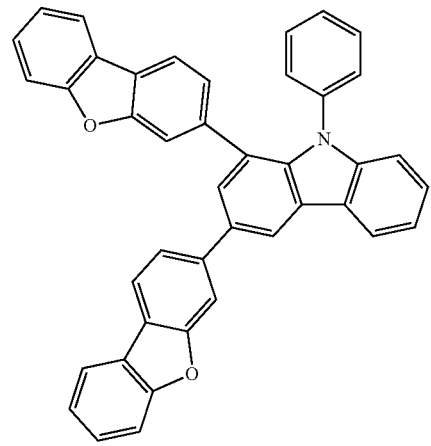

15
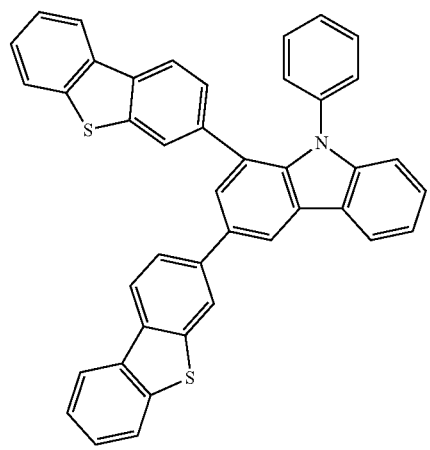
16
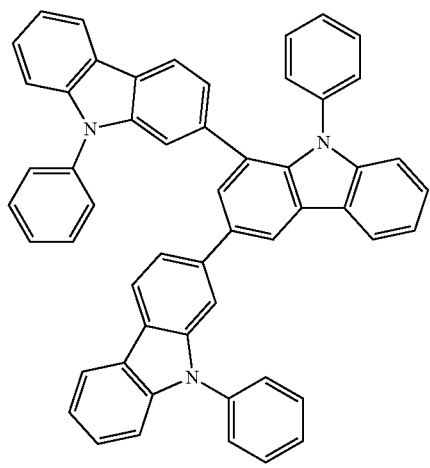
17
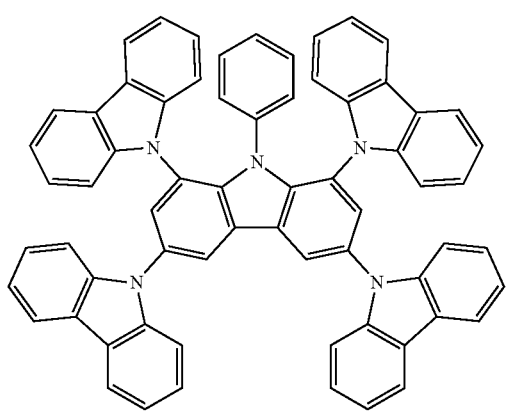
18
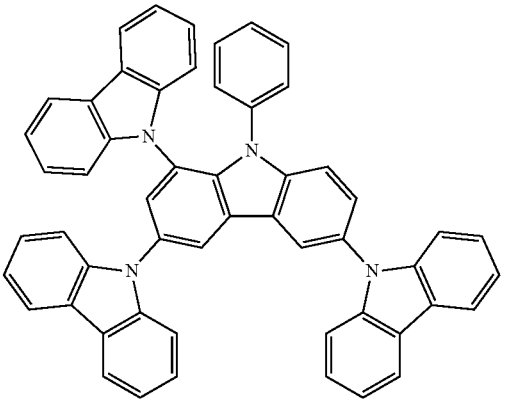
19
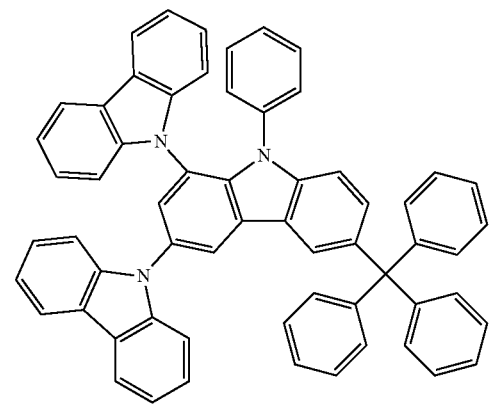
20
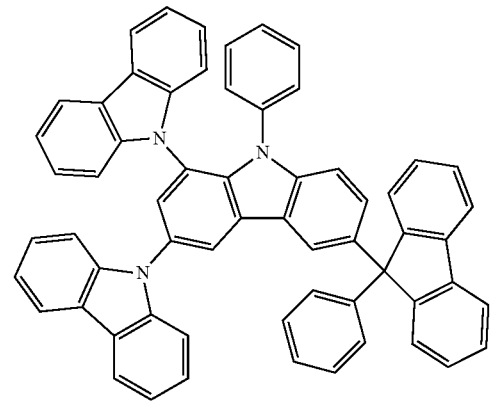
21
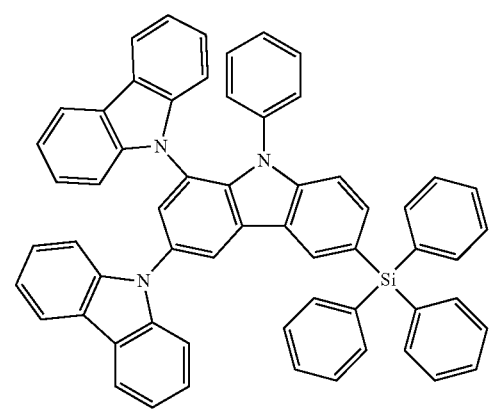

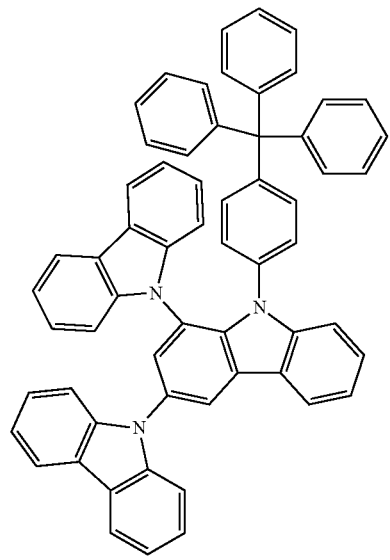
22
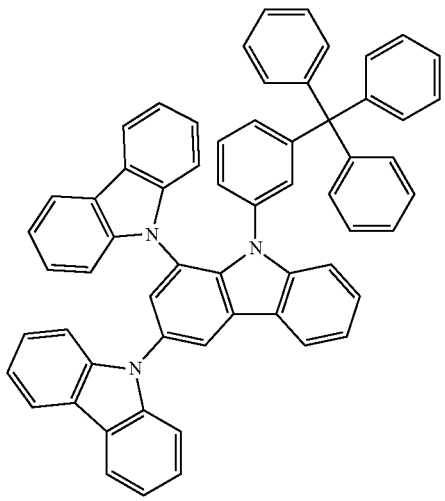
25
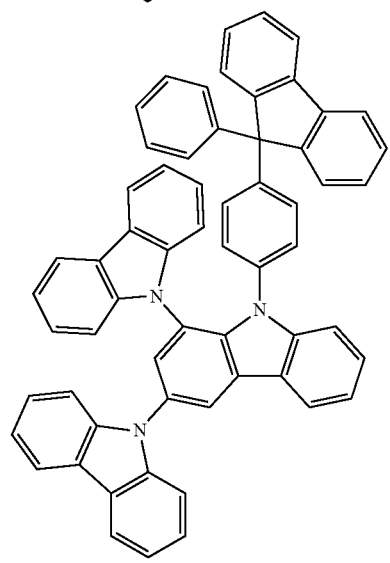
23
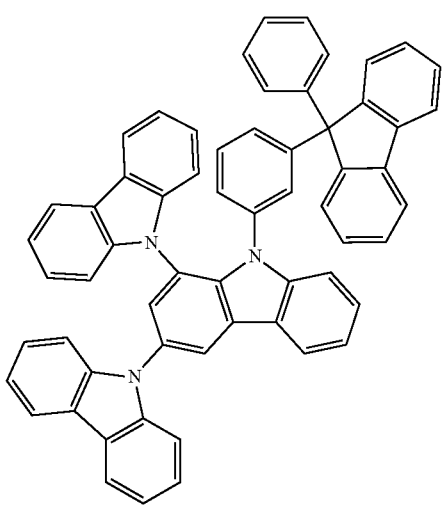
26
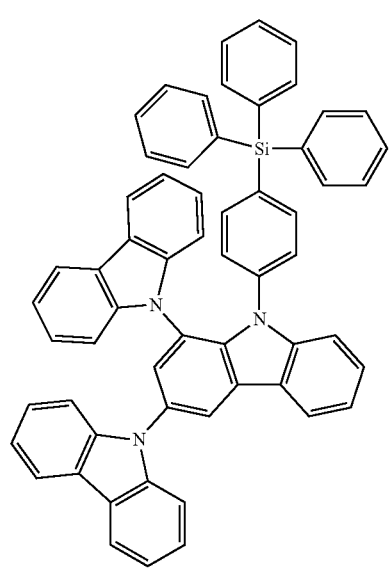
24
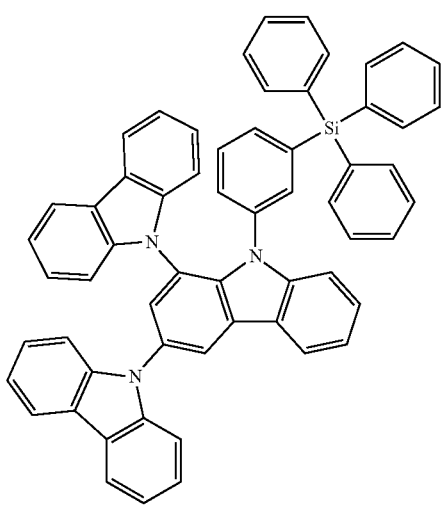
27

28
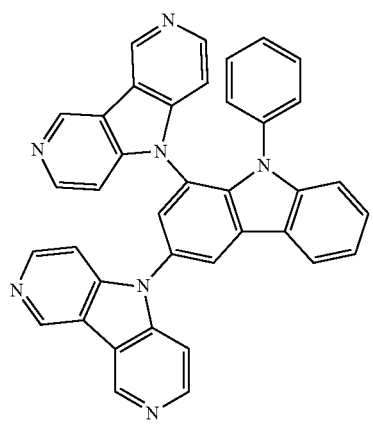
29
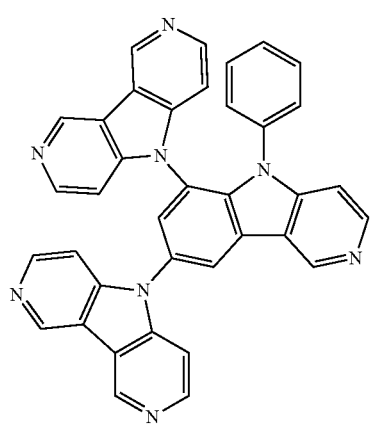
30
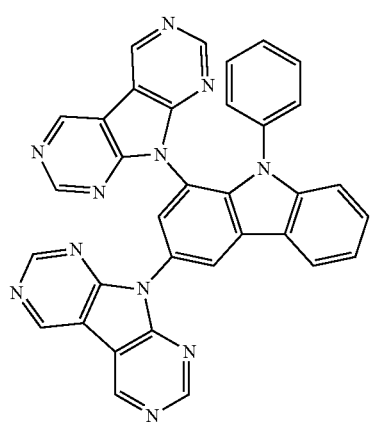
31
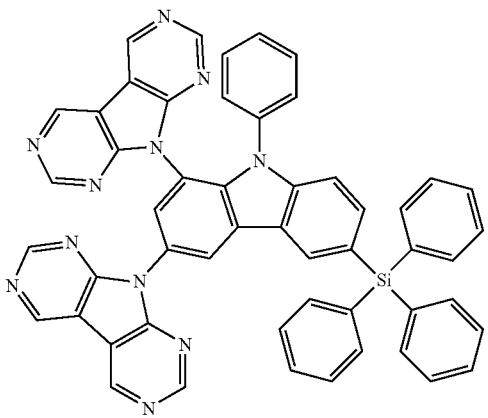
32
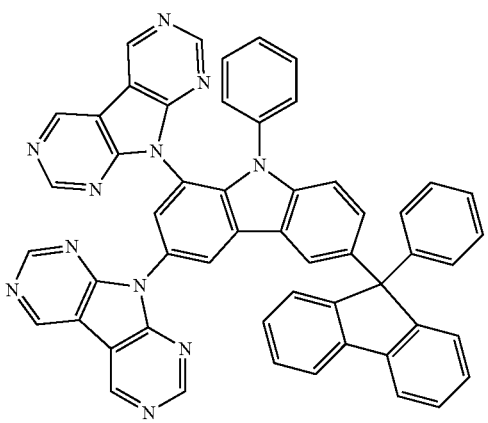
33
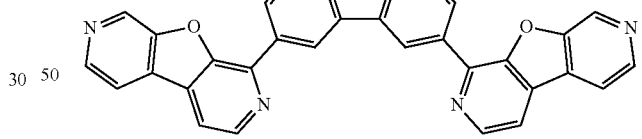
34
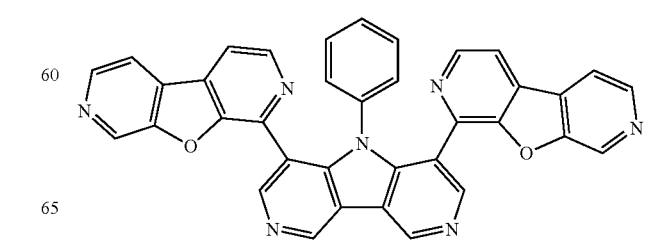

35
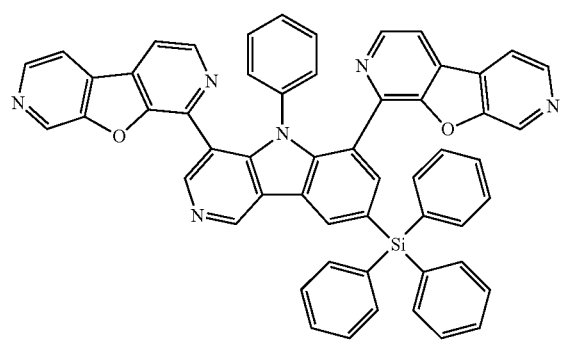
36
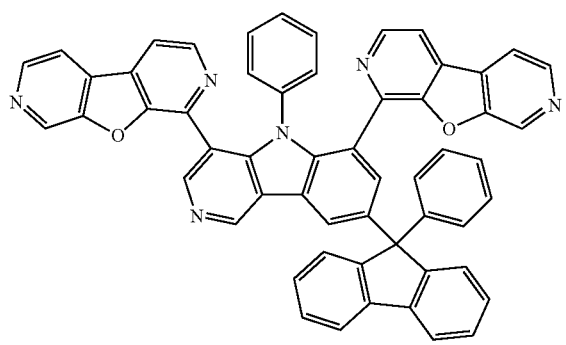
38
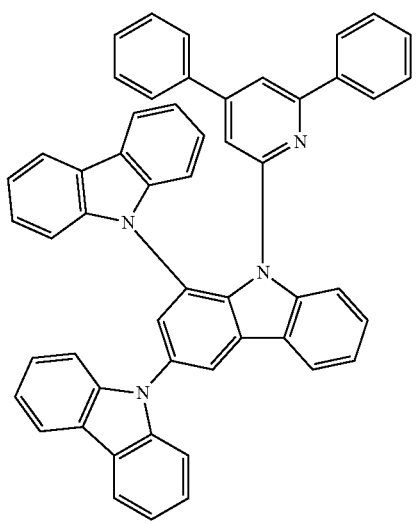
39
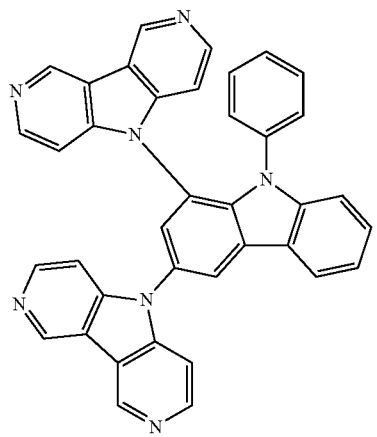
40
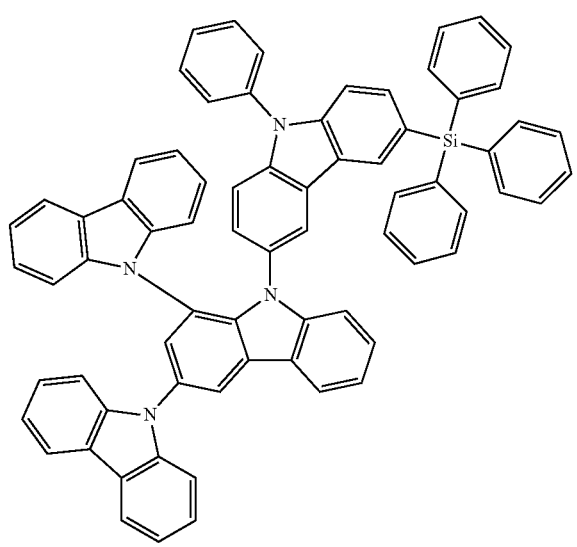
41
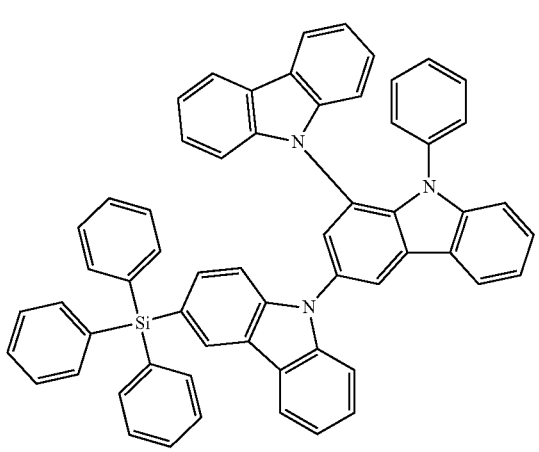

42
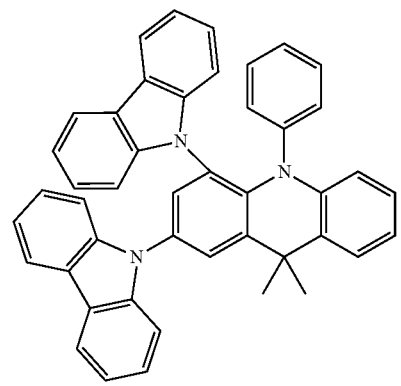
43
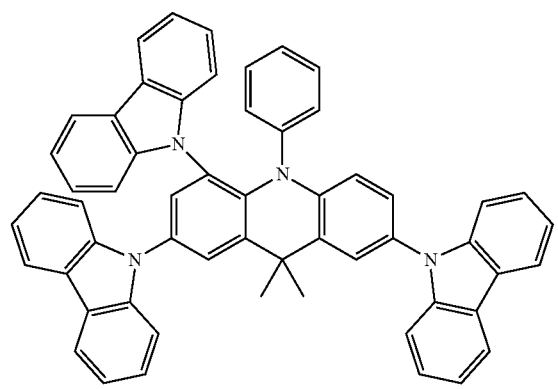
44
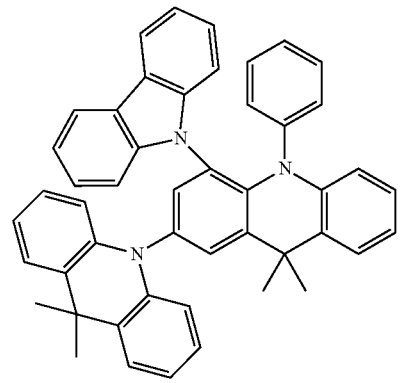
45
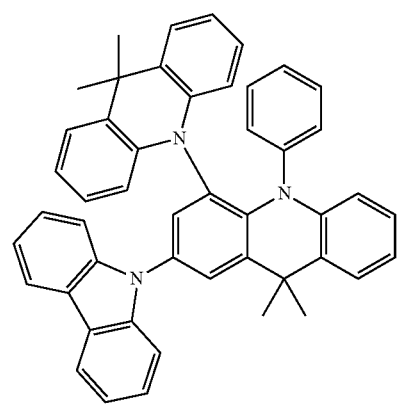
46
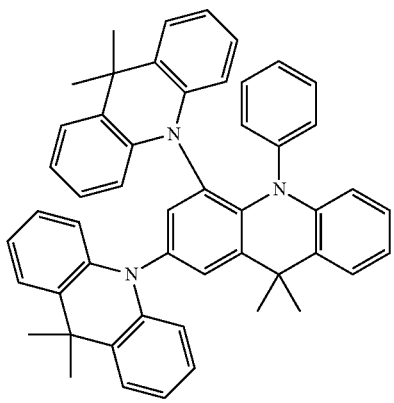
47
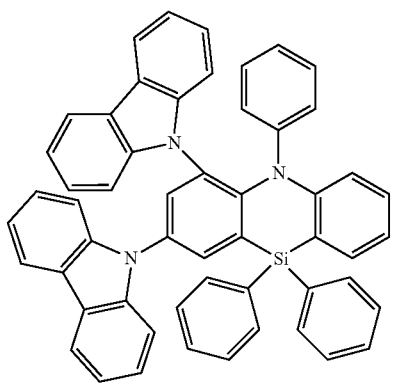
48
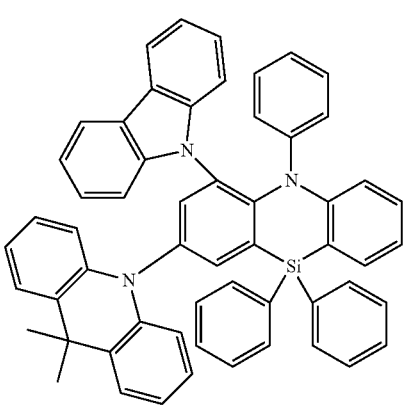

-continued

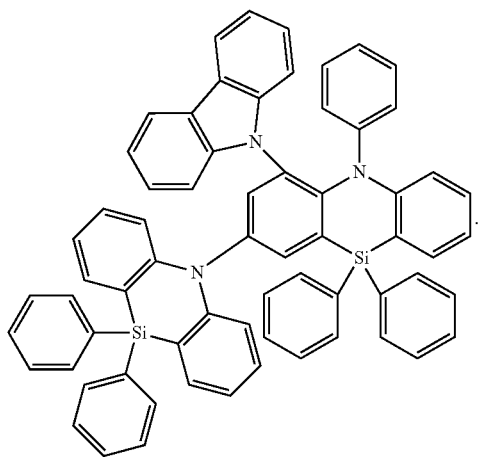

49

14. An organic electroluminescence device, comprising:
a first electrode;
a hole transport region provided on the first electrode;
an emission layer provided on the hole transport region;
an electron transport region provided on the emission layer; and
a second electrode provided on the electron transport region,
wherein the emission layer comprises a heterocyclic compound represented by the following Formula 1:

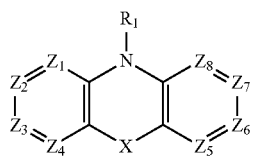

[Formula 1]

wherein in Formula 1,
X is a direct linkage, or $CR_2R_3$,
$Z_1$ to $Z_8$ are each independently $CR_4$ or N,
each of $R_1$ to $R_4$ is independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring,
at least two of $Z_1$, $Z_3$, $Z_6$ and $Z_8$ are $CR_5$, and
$R_5$ is represented by the following Formula 2 or Formula 3:

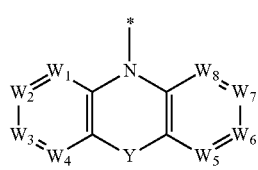

[Formula 2]

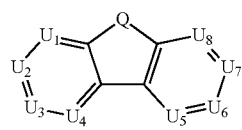

[Formula 3]

wherein in Formula 2,
Y is a direct linkage, $CR_6R_7$, $SiR_8R_9$, $NR_{10}$, O, S or $SO_2$,
each of $W_1$ to $W_8$ is independently $CR_{11}$ or N, and
each of $R_6$ to $R_{11}$ is independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring,
except that
if $Z_1$ and $Z_3$ in Formula 1 are each independently $CR_5$ wherein $R_5$ is represented by Formula 2 or $Z_6$ and $Z_8$ in Formula 1 are each independently $CR_5$ wherein $R_5$ is represented by Formula 2 or $Z_3$ and $Z_6$ in Formula 1 are each independently $CR_5$ wherein $R_5$ is represented by Formula 2, and
if X in Formula 1 is a direct linkage, and
if $W_1$ to $W_8$ in Formula 2 are each $CR_{11}$,
then Y in Formula 2 is not a direct linkage, and
wherein in Formula 3,
Q is $NR_{12}$, O, or S,
$U_1$ to $U_8$ are each independently $CR_{13}$ or N,
one of $U_1$ to $U_8$ is a connecting part, and
each of $R_{12}$ and $R_{13}$ is independently a hydrogen atom, a deuterium atom, a substituted or unsubstituted silyl group, a substituted or unsubstituted alkyl group having 1 to 20 carbon atoms, a substituted or unsubstituted hydrocarbon ring group having 6 to 30 carbon atoms for forming a ring, or a substituted or unsubstituted heterocyclic group having 2 to 30 carbon atoms for forming a ring,
except that
if $Z_3$ and $Z_6$ in Formula 1 are each independently $CR_5$ wherein $R_5$ is represented by Formula 3, and
if X in Formula 1 is either a direct linkage or $CR_2R_3$ wherein $R_2$ and $R_3$ are each an alkyl group,
then Q in Formula 3 is not $NR_{12}$.

15. The organic electroluminescence device of claim 14, wherein each of $Z_1$ and $Z_3$ is independently represented by $CR_5$.

16. The organic electroluminescence device of claim 14, wherein $R_1$ is a substituted or unsubstituted phenyl group, a substituted or unsubstituted pyridine group, or a substituted or unsubstituted carbazole group.

17. The organic electroluminescence device of claim 14, wherein the emission layer comprises a host and a dopant, and
the host comprises the heterocyclic compound represented by Formula 1.

18. The organic electroluminescence device of claim 17, wherein the host is a phosphorescence host or a thermally activated delayed fluorescence host.

19. The organic electroluminescence device of claim 14, wherein the heterocyclic compound represented by Formula 1 is at least one selected from compounds represented in the following Formula Compound Group 1:

[Compound Group 1]
1
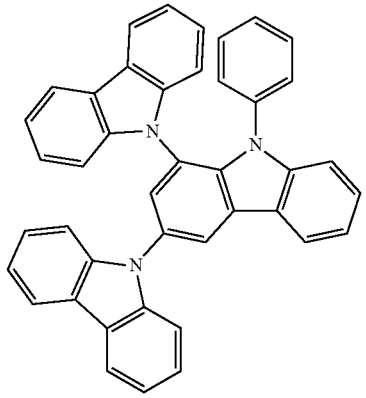
2
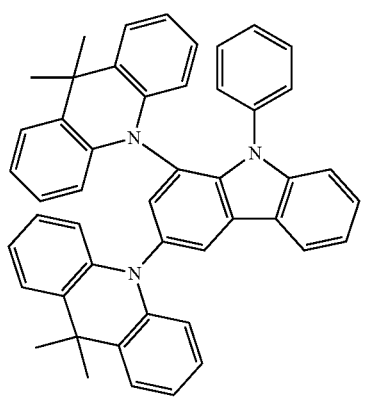
3
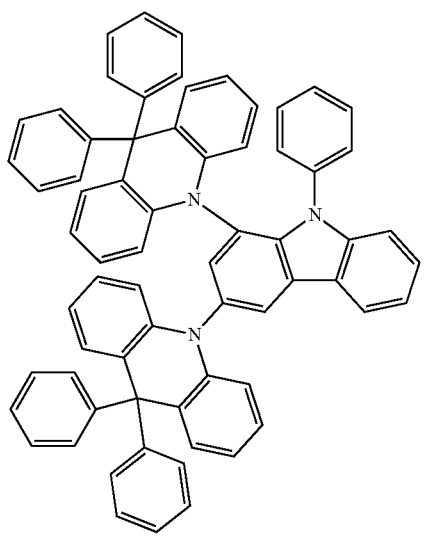
4
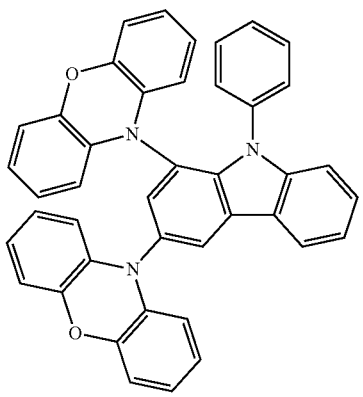
5
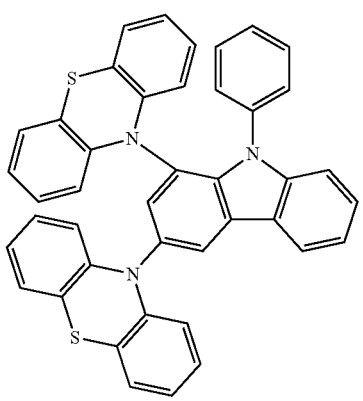
6
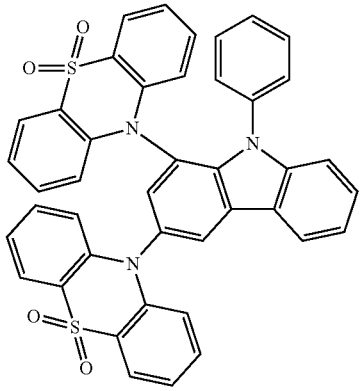

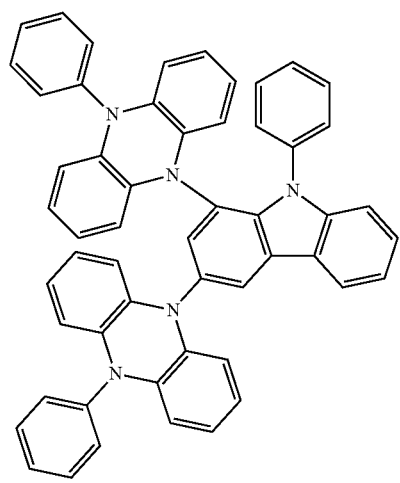
7
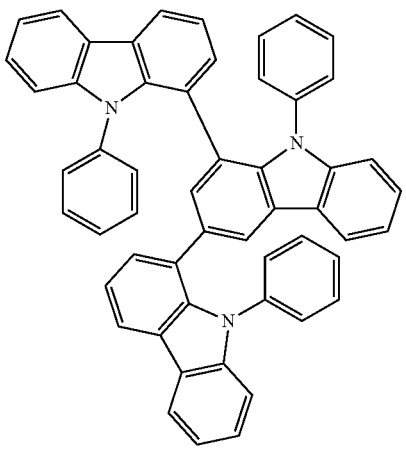
10
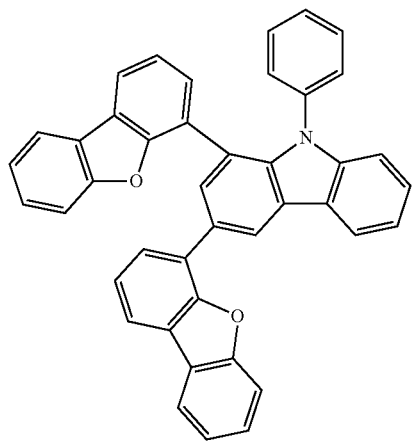
8
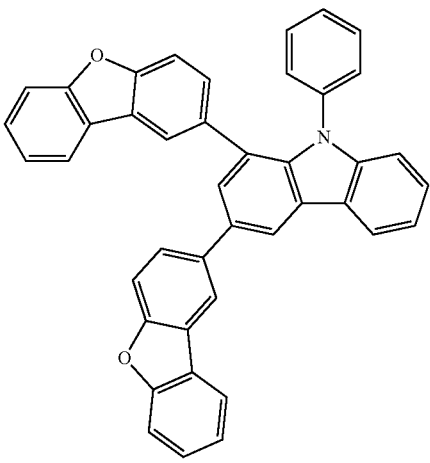
11
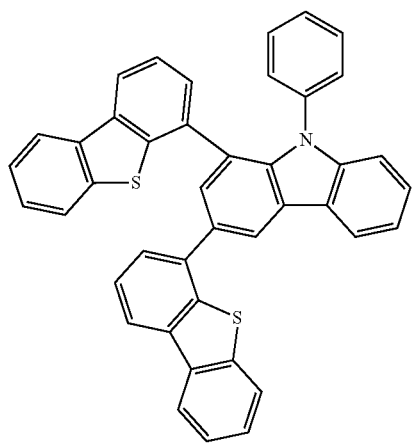
9
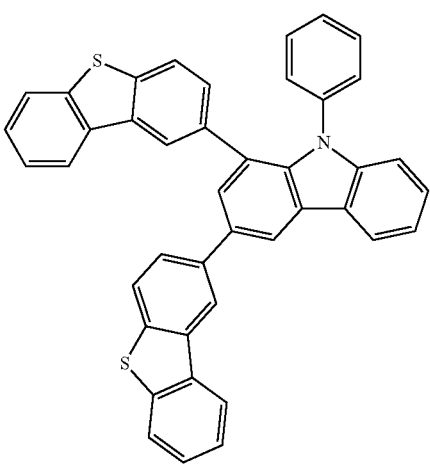
12

13
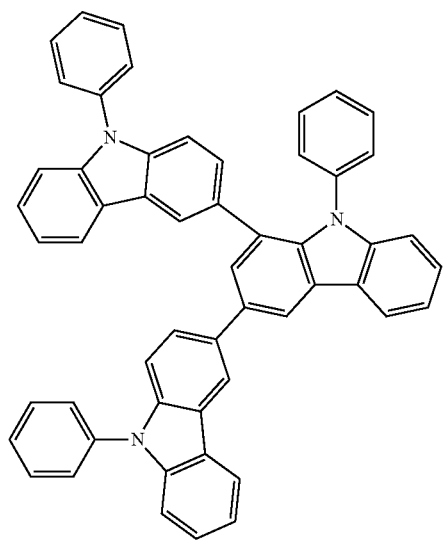
14
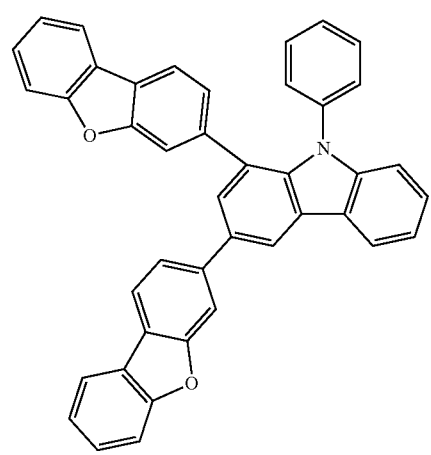
15
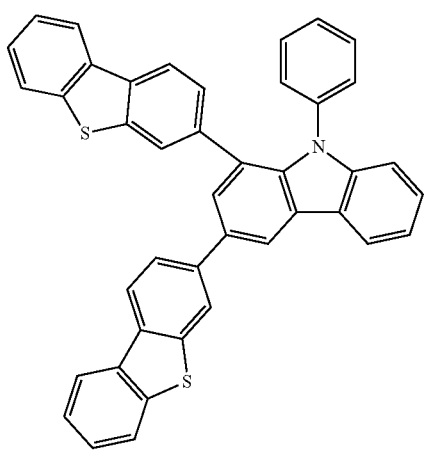
16
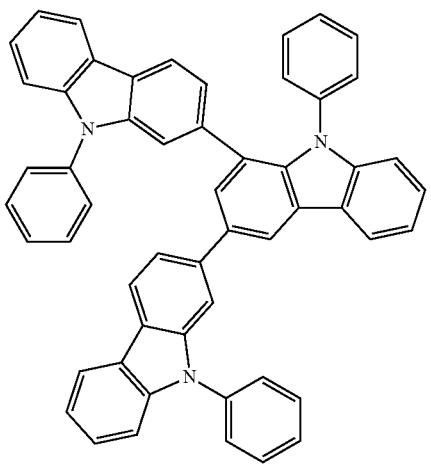
17
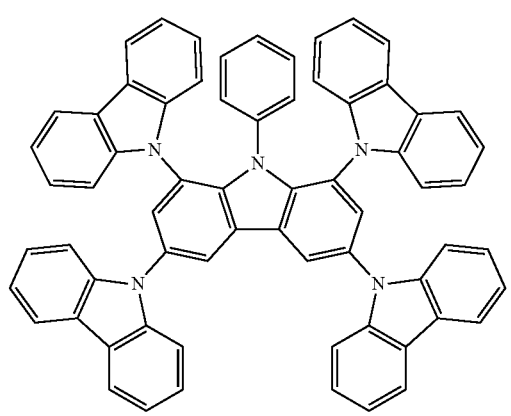
18
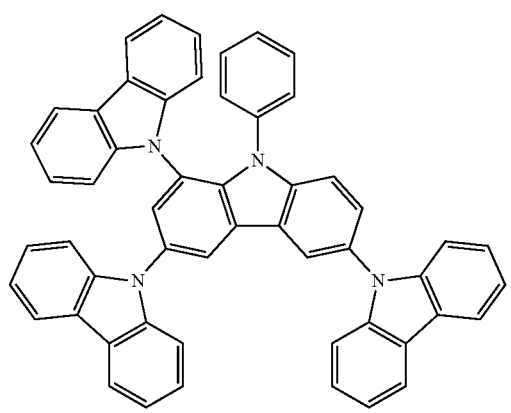

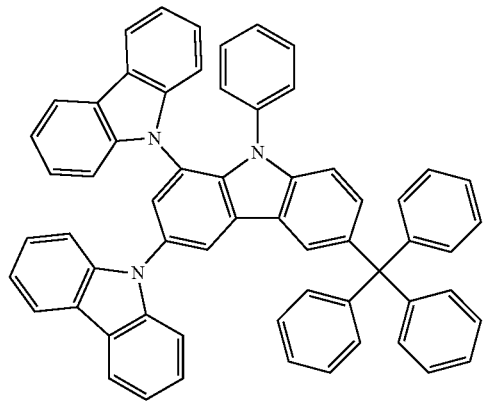
19
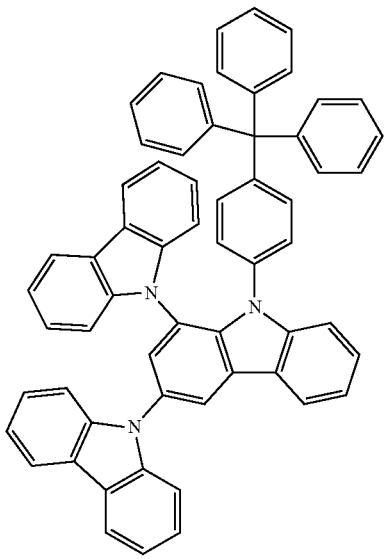
22
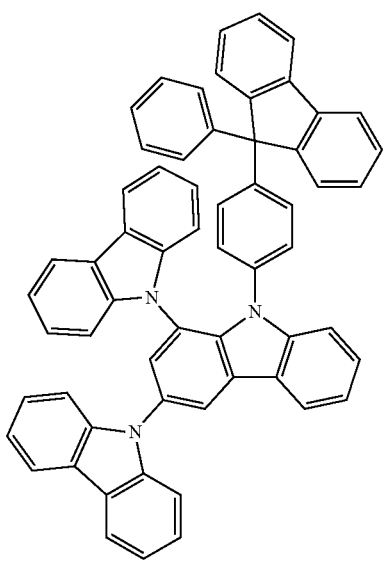
23
20
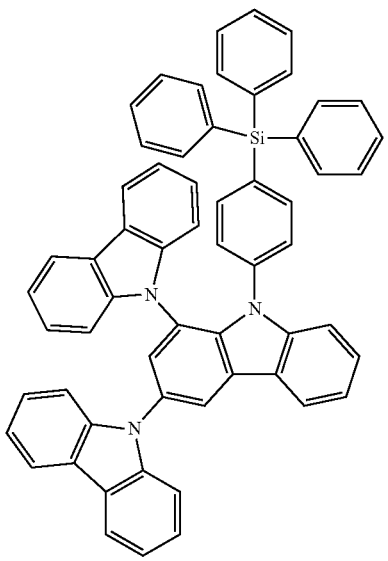
24
21

25
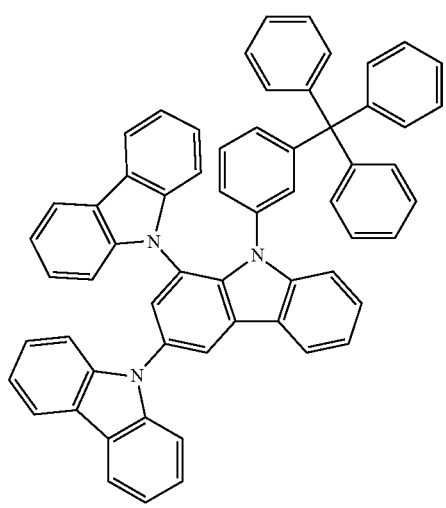
26
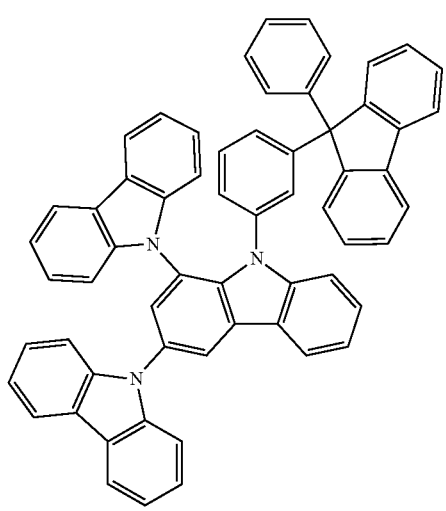
27
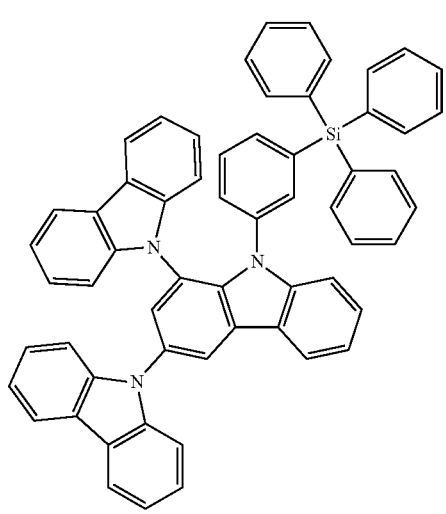
28
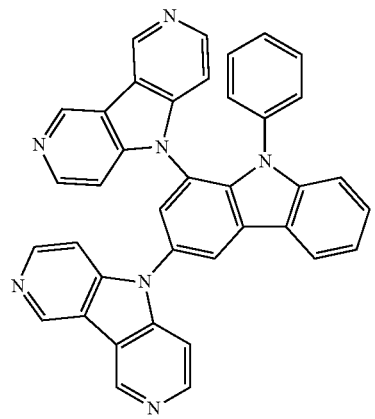
29
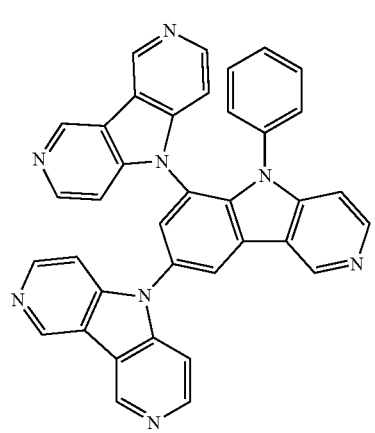
30
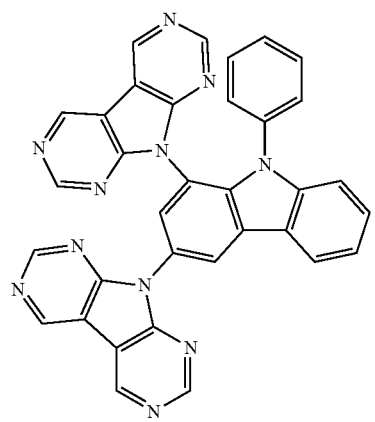

31
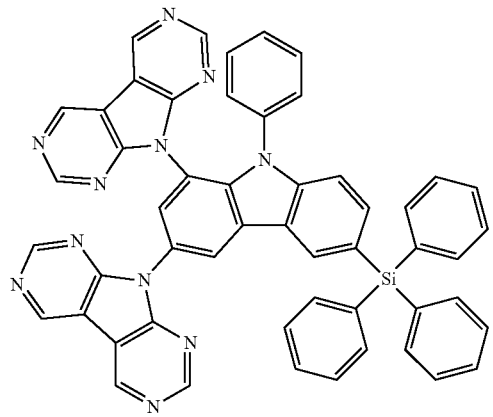
32
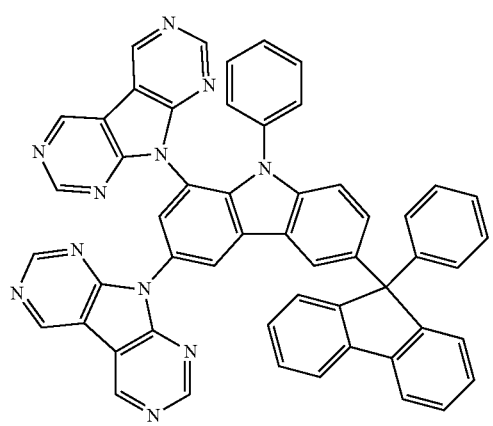
33
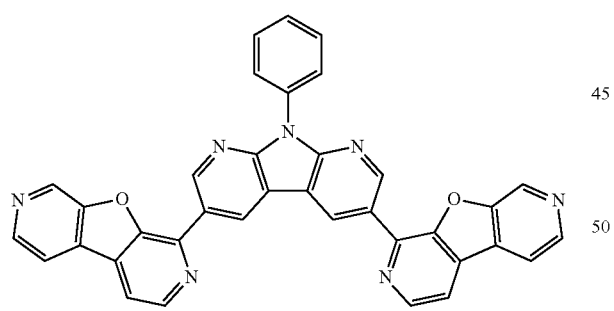
34
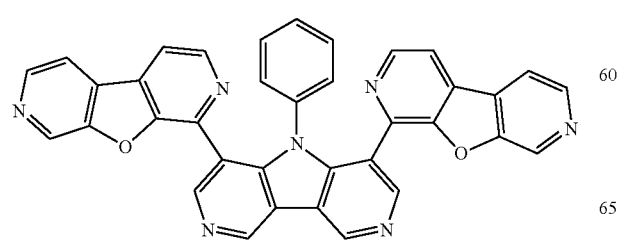
35
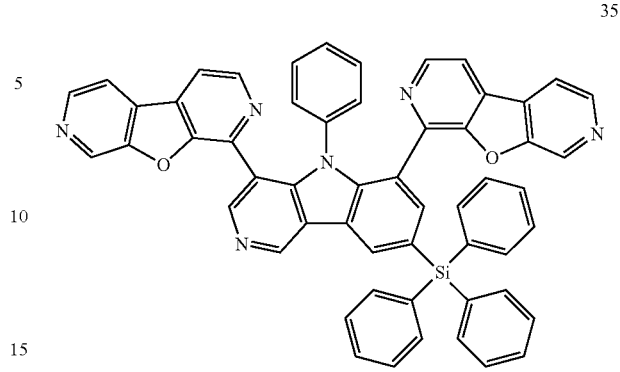
36
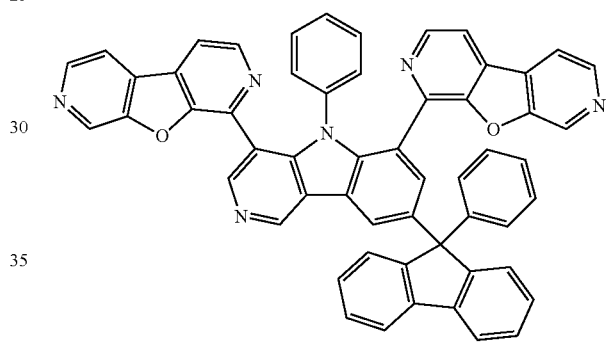
38
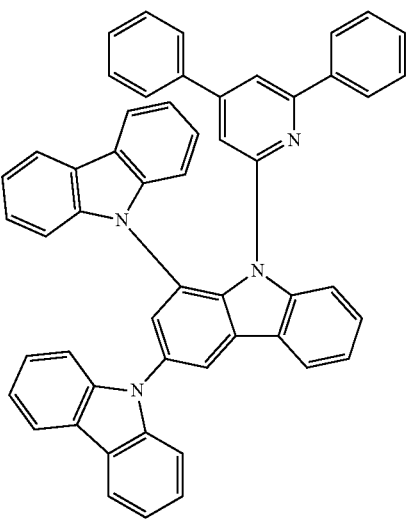

39
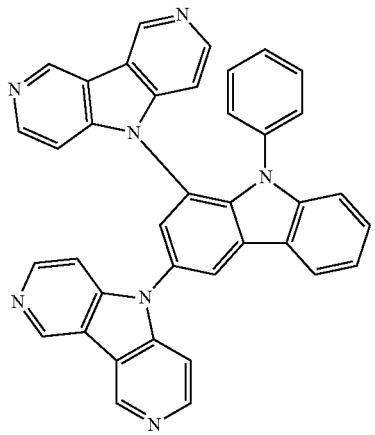
40
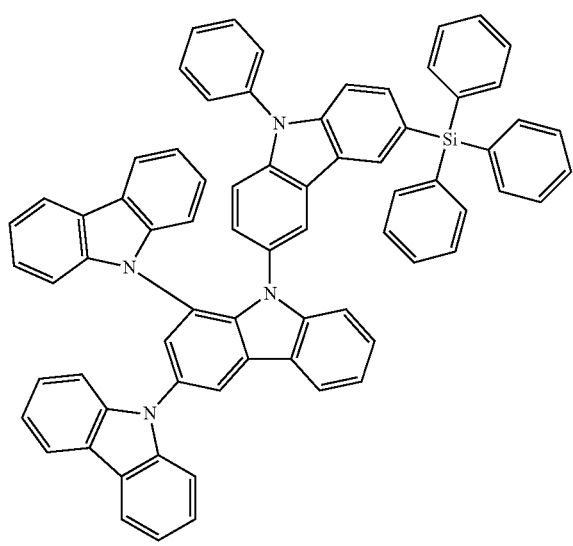
41
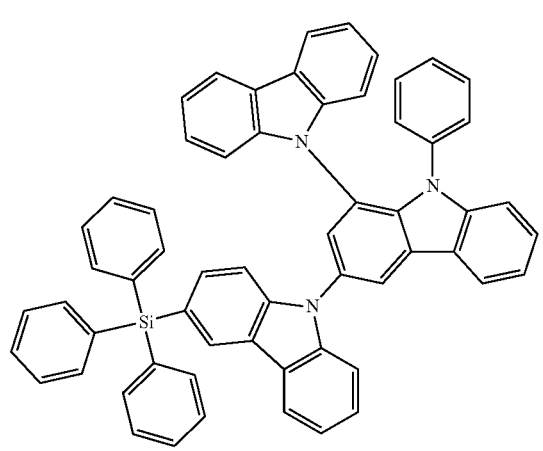
42
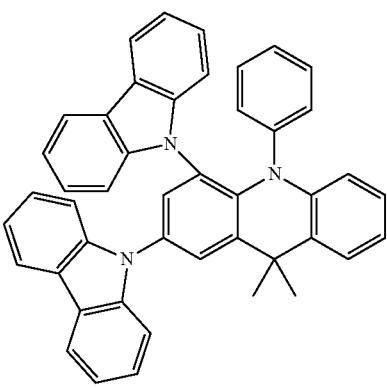
43
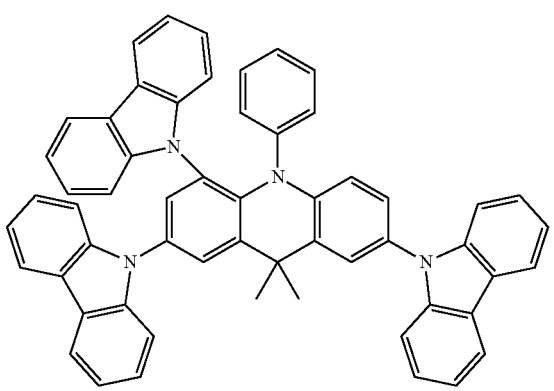
44
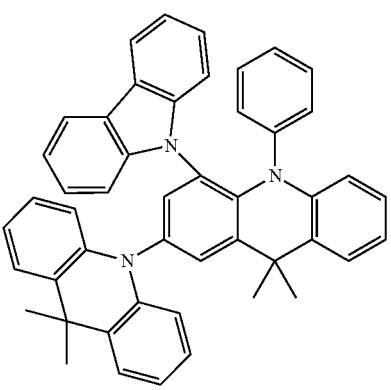
45
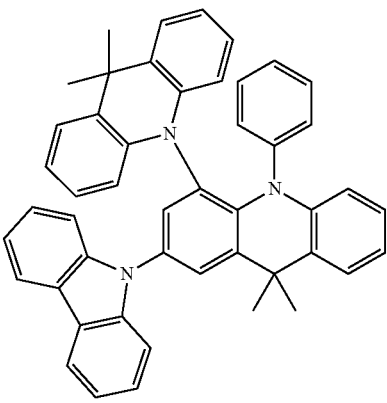

46
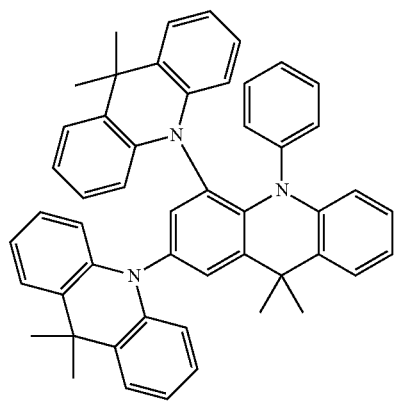
47
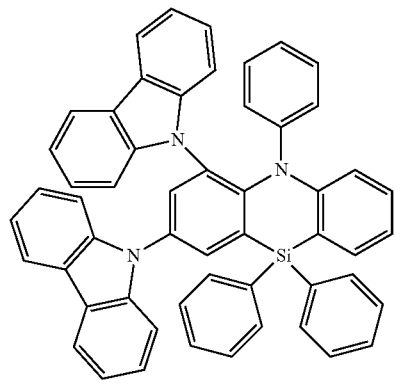
48
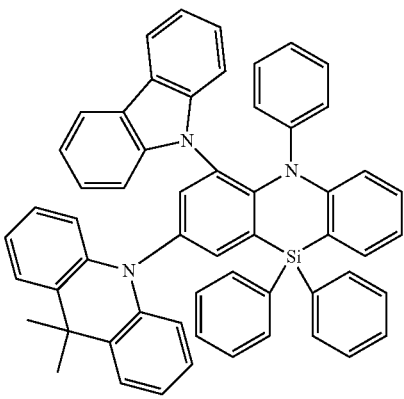
49
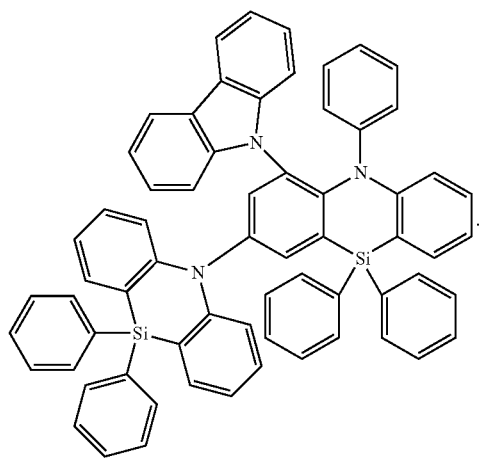
* * * * *